United States Patent
Brodney et al.

(10) Patent No.: US 9,233,981 B1
(45) Date of Patent: Jan. 12, 2016

(54) SUBSTITUTED PHENYL HEXAHYDROPYRANO[3,4-D][1,3]THIAZIN-2-AMINE COMPOUNDS

(71) Applicant: Pfizer Inc., New York, NY (US)

(72) Inventors: Michael Aaron Brodney, Newton, MA (US); Brian Thomas O'Neill, Haddam, CT (US); Christopher Ryan Butler, Canton, MA (US); Elizabeth Mary Beck, Edinburgh (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 14/767,414

(22) PCT Filed: Feb. 2, 2014

(86) PCT No.: PCT/IB2014/058777
§ 371 (c)(1),
(2) Date: Aug. 12, 2015

(87) PCT Pub. No.: WO2014/125397
PCT Pub. Date: Aug. 21, 2014

Related U.S. Application Data

(60) Provisional application No. 61/765,283, filed on Feb. 15, 2013.

(51) Int. Cl.
C07D 513/04 (2006.01)
(52) U.S. Cl.
CPC .................................. C07D 513/04 (2013.01)
(58) Field of Classification Search
CPC .................................................... C07D 513/04
USPC ........................................ 544/48; 514/224.2
See application file for complete search history.

(56) References Cited

U.S. PATENT DOCUMENTS

| | | | |
|---|---|---|---|
| 5,750,349 A | 5/1998 | Suzuki et al. |
| 7,115,600 B2 | 10/2006 | Wager et al. |
| 7,285,293 B2 | 10/2007 | Castillo et al. |
| 7,975,664 B2 | 7/2011 | Himsel et al. |
| 8,158,620 B2 | 4/2012 | Suzuki et al. |
| 8,198,269 B2 | 6/2012 | Motoki et al. |
| 8,278,441 B2 | 10/2012 | Mergott et al. |
| 8,822,456 B2 | 9/2014 | Brodney et al. |
| 8,865,706 B2 | 10/2014 | Brodney et al. |
| 8,933,221 B2 | 1/2015 | Brodney et al. |
| 8,962,616 B2 | 2/2015 | Brodney et al. |
| 9,045,498 B2 | 6/2015 | Brodney et al. |
| 9,045,499 B2 | 6/2015 | Brodney et al. |
| 2003/0073655 A1 | 4/2003 | Chain |
| 2003/0195205 A1 | 10/2003 | DeNinno et al. |
| 2004/0192898 A1 | 9/2004 | Jia et al. |
| 2004/0220186 A1 | 11/2004 | Bell et al. |
| 2005/0019328 A1 | 1/2005 | Schenk |
| 2005/0043354 A1 | 2/2005 | Wager et al. |
| 2005/0048049 A1 | 3/2005 | Schenk |
| 2005/0256135 A1 | 11/2005 | Lunn et al. |
| 2005/0267009 A1 | 12/2005 | Deagle |
| 2005/0267095 A1 | 12/2005 | Bernardelli et al. |
| 2005/0267100 A1 | 12/2005 | Elliott et al. |
| 2006/0057701 A1 | 3/2006 | Rosenthal et al. |
| 2006/0106035 A1 | 5/2006 | Hendrix et al. |
| 2006/0111372 A1 | 5/2006 | Hendrix et al. |
| 2006/0178501 A1 | 8/2006 | Summers et al. |
| 2007/0031416 A1 | 2/2007 | Shoji et al. |
| 2007/0160616 A1 | 7/2007 | Rosenthal et al. |
| 2007/0179175 A1 | 8/2007 | Lunn |
| 2008/0096955 A1 | 4/2008 | Wager et al. |
| 2008/0176925 A1 | 7/2008 | Butler et al. |
| 2009/0054482 A1 | 2/2009 | Chan et al. |

(Continued)

FOREIGN PATENT DOCUMENTS

| | | |
|---|---|---|
| EP | 0994728 | 10/1998 |
| EP | 1257584 | 10/2004 |

(Continued)

OTHER PUBLICATIONS

Alberti, K.G. et al., "The Metabolic Syndrome—A New Worldwide Definition," Lancet, Sep. 24-30, 2005, pp. 1059-1062, 366(9491).
Carpino, P.A., et al., "Diabetes Area Participation Analysis: A Review of Companies and Targets Described in the 2008-2010 Patent Literature", Expert Opinion on Therapeutic Patents, Dec. 2010, pp. 1627-1651, 20(12).
Chao, Edward, et al., "SGLT2 Inhibition—A Novel Strategy for Diabetes Treatment", Nature Reviews Drug Discovery, Jul. 2010, pp. 551-559, 9(7).

(Continued)

Primary Examiner — Kahsay Habte
(74) Attorney, Agent, or Firm — John A. Wichtowski

(57) ABSTRACT

The present invention is directed to compounds, tautomers and pharmaceutically acceptable salts of the compounds which are disclosed, wherein the compounds have the structure of Formula I,

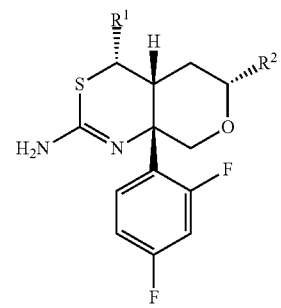

wherein the variables $R^1$ and $R^2$ are as defined in the specification. Corresponding pharmaceutical compositions, methods of treatment, methods of synthesis, and intermediates are also disclosed.

17 Claims, No Drawings

(56) References Cited

U.S. PATENT DOCUMENTS

| | | | |
|---|---|---|---|
| 2010/0056618 A1 | 3/2010 | Mascitti et al. |
| 2010/0093999 A1 | 4/2010 | Motoki et al. |
| 2010/0285145 A1 | 11/2010 | Darout et al. |
| 2011/0027279 A1 | 2/2011 | Chain |
| 2011/0038861 A1 | 2/2011 | Rosenthal et al. |
| 2011/0046122 A1 | 2/2011 | Andreini et al. |
| 2011/0207723 A1 | 8/2011 | Motoki et al. |
| 2012/0245155 A1 | 9/2012 | Yoshida et al. |
| 2013/0053373 A1 | 2/2013 | Brodney et al. |
| 2013/0296308 A1 | 11/2013 | Brodney et al. |
| 2015/0087637 A1 | 3/2015 | Brodney et al. |
| 2015/0133438 A1 | 5/2015 | Brodney et al. |

FOREIGN PATENT DOCUMENTS

| | | |
|---|---|---|
| EP | 2332943 | 6/2011 |
| EP | 2511269 | 10/2012 |
| WO | 9844955 | 10/1998 |
| WO | 0220521 | 3/2002 |
| WO | 03072197 | 9/2003 |
| WO | 2004032868 | 4/2004 |
| WO | 2005025616 | 3/2005 |
| WO | 2005049616 | 11/2005 |
| WO | 2005116014 | 12/2005 |
| WO | 2005116034 | 12/2005 |
| WO | 2006069081 | 6/2006 |
| WO | 2006118959 | 11/2006 |
| WO | 2006120552 | 11/2006 |
| WO | 2006126081 | 11/2006 |
| WO | 2006126082 | 11/2006 |
| WO | 2006126083 | 11/2006 |
| WO | 2006136924 | 12/2006 |
| WO | 2007063385 | 6/2007 |
| WO | 2007069053 | 6/2007 |
| WO | 2007088450 | 8/2007 |
| WO | 2007088462 | 9/2007 |
| WO | 2007099423 | 9/2007 |
| WO | 2007105053 | 9/2007 |
| WO | 2007138431 | 9/2007 |
| WO | 2007122466 | 11/2007 |
| WO | 2007122482 | 11/2007 |
| WO | 2008065508 | 6/2008 |
| WO | 2009016462 | 2/2009 |
| WO | 2009091016 | 7/2009 |
| WO | 2009144554 | 12/2009 |
| WO | 2009144555 | 12/2009 |
| WO | 2010013161 | 2/2010 |
| WO | 2010038686 | 4/2010 |
| WO | 2010086820 | 8/2010 |
| WO | 2010103437 | 9/2010 |
| WO | 2010103438 | 9/2010 |
| WO | 2010106457 | 9/2010 |
| WO | 2010140092 | 12/2010 |
| WO | 2011005611 | 1/2011 |
| WO | 2011071109 | 6/2011 |
| WO | 2012098461 | 7/2012 |
| WO | 2012162334 | 11/2012 |
| WO | 2013030713 | 3/2013 |
| WO | 2013164730 | 11/2013 |

OTHER PUBLICATIONS

Demong, D.E. et al., "Chapter 8, Glucagon Receptor Antagonists for Type II Diabetes", Annual Reports in Medicinal Chemistry 2008, pp. 119-137, vol. 43.

Denmark, S.E., et al., "Allylation of Carbonyls: Methodology and Stereochemistry", Modern Carbonyl Chemistry, 2000, Chapter 10, pp. 299-401.

England, et al., "An Improved Synthesis of a Novel α1A Partial Agonist Including A New Two-Step Synthesis of 4-Fluoropyrazole", Tetrahedron Letters, May 26, 2010, pp. 2849-2851, 51(21).

English equivalent U.S. Pat. No. 8158620; Suzuki, et al., filed Jan. 16, 2009 for WO 2009091016, published Jun. 23, 2007.

Esterhazy, Daria, et al., "BACE2 Is a β Cell-Enriched Protease that Regulates Pancreatic β Cell Function and Mass", Cell Metabolism, Sep. 2011, pp. 365-377, 14(3).

Farah, M., et al., "Reduced BACE1 Activity Enhances Clearance of Myelin Debris and Regeneration of Axons in the Injured Peripheral Nervous System", Journal of Neuroscience, Apr. 13, 2011, pp. 5744-5754, 31(15).

Finnin, Barrie, et al., "Transdermal Penetration Enhancers" Applications, Limitations, and Potential, Journal Pharmaceutical Sciences, Oct. 1999, pp. 955-958, 88(10).

Flack, H.D., ", On Enantiomorph-Polarity Estimation", Acta Cryst., 1983, pp. 876-881, vol. A39.

Glenner, G., et al., "Amyloidosis of the Nervous System", Journal of Neurological Science, 1989, pp. 1-28, vol. 94.

Guidance for Industry, Q3C—Tables and List, U.S. Department of Health and Human Services, Food and Drug Administration, Center for Drug Evaluation and Research (CDER), Center for Biologics Evaluation and Research (CBER), Nov. 2003, ICH, Revision I.

Haan, J., et al., "Amyloid in Central Nervous System Disease", Clinical Neurology and Neurosurgery, 1990, pp. 305-310, 92(4).

Haleblian, John K., "Characterization of Habits and Crystalline Modification of Solids and Their Pharmaceutical Applications", Journal Pharmaceutical Sciences, Aug. 1975, pp. 1269-1288, 64(8).

Hooft, Rob, et al., "Determination of Absolute Structure Using Bayesian Statistics on Bijvoet differences", Journal of Applied Crystallography, Feb. 2008, pp. 96-103, 41(1).

International Application No. PCT/IB2012/054198, filed Aug. 17, 2012, International Search Report and Written Opinion, mailed Jan. 23, 2013, 14 pages.

International Application No. PCT/IB2013/053178, filed Apr. 22, 2013, International Search Report, mailed Jul. 3, 2013, 5 pages.

International Application No. PCT/IB2013/058402, filed Sep. 9, 2013, International Search Report, mailed Dec. 16, 2013, 11 pages.

International Application No. PCT/IB2013/060456, filed Nov. 27, 2013, International Search Report, mailed Feb. 21, 2014, 8 pages.

Jones, R.M. et al., "Chapter 7, The Emergence of GPR119 Agonists as Anti-Diabetic Agents", Annual Reports in Medicinal Chemistry 2009, pp. 149-170, vol. 44.

Kharitonenkov, A. et al., "FGF21: A Novel Prospect for the Treatment of Metabolic Diseases", Current Opinion in Investigational Drugs, Apr. 2009, pp. 359-364, 10(4).

MacRae, Clare, et al., "Mercury: Visualization and Analysis of Crystal Structures", Journal of Applied Crystallography, Jun. 2006, pp. 453-457, 39(3).

Meakin, Paul, et al., "Reduction in BACE1 decreases body weight, protects against diet-induced obesity and enhances insulin sensitivity in mice", Biochemical Journal, Jan. 1, 2012, pp. 285-296, 441(1).

Medina, J.C., et al., "Chapter 5, GPR40 (FFAR1) Modulators", Annual Reports in Medicinal Chemistry 2008, pp. 75-85, vol. 43.

Miyaura, N., et al., "Palladium-Catalyzed Cross-Coupling Reactions of Organoborn Compounds", Chemical Review, Nov. 1995, pp. 2457-2483, 95(7).

Olsen, R., et al., "Secretase Inhibitors and Modulators for the Treatment of Alzheimer's Disease", Annual Reports in Medicinal Chemistry, 2007, pp. 27-47, vol. 42.

PCT/IB2013/058402 application filed Sep. 9, 2013.
PCT/IB2013/060456 application filed Nov. 27, 2013.
PCT/IB2013/060633 application filed Dec. 4, 2013.
PCT/IB2014/058760 application filed Feb. 3, 2014.
PCT/IB2014/058777 application filed Feb. 4, 2014.

International Patent Application No. PCT/IB2014/058777, filed Feb. 4, 2014, International Search Report and Written Opinion, mailed Mar. 25, 2014, 11 pages.

Sheppeck, J.E. II, et al., "A Convenient and Scaleable Procedure for Removing the Fmoc Group in Solution", Tetrahedron Letters, 2000, pp. 5329-5333, vol. 41(28).

Spek, A.L., "Single-Crystal Structure Validation with the Program Platon", Journal of Applied Crystallography, Feb. 2003, pp. 7-13, 36(1).

(56) References Cited

OTHER PUBLICATIONS

Suzuki, Akira, "Recent advances in the cross-coupling reactions of organoboron derivatives with organic electrophiles 1995-1998", Journal Organometallic Chemistry, 1999, pp. 147-168, vol. 576.

Zhang, S. et al., "PTP1B as a Drug Target: Recent Developments in PTP1B Inhibitor Discovery", Drug Discovery Today, May 2007, pp. 373-381, 12(9/10).

Zhong, M., "TGR5 as a Therapeutic Target for Treating Obesity", Current Topics in Medicinal Chemistry, 2010, pp. 386-396, 10(4).

Zimmet, P.Z. et al., "The Metabolic Syndrome: Perhaps an Etiologic Mystery but Far From a Myth—Where Does the International Diabetes Federation Stand?," Medscape Diabetes & Endocrinology, Oct. 11, 2005, 8 pages, www.medscape.com, 7(2).

International Application No. PCT/IB2013/060456, filed Nov. 27, 2013, International Preliminary Report on Patentability, mailed Jun. 16, 2015, 5 pages.

International Application No. PCT/IB2013/060633, filed Dec. 4, 2013, International Search Report and Written Opinion, mailed Mar. 24, 2014.

International Application No. PCT/IB2015/052279, filed Mar. 27, 2015, International Search Report and Written Opinion, mailed Jun. 24, 2015, 10 pages.

International Application No. PCT/IB2013/060633, filed Dec. 4, 2013, International Preliminary Report on Patentability, mailed Jun. 23, 2015.

International Application No. PCT/IB2014/0558760 filed Feb. 3, 2014, International Preliminary Report on Patentability, mailed Aug. 18, 2015, 7 pages.

International Application No. PCT/IB2014/0558777 filed Feb. 4, 2014, International Preliminary Report on Patentability, mailed Aug. 18, 2015, 7 pages.

International Application No. PCT/IB2014/0558760 filed Feb. 3, 2014, International Search Report and Written Opinion, mailed Mar. 13, 2014, 10 pages.

SUBSTITUTED PHENYL HEXAHYDROPYRANO[3,4-D][1,3]THIAZIN-2-AMINE COMPOUNDS

This application is a national stage application under 35 U.S.C. 371 of PCT/IB2014/058777, filed on Feb. 4, 2014, which claims the benefit of U.S. Provisional Patent Application No. 61/765,283, filed on Feb. 15, 2013, the disclosure of which is hereby incorporated by reference in its entirety.

FIELD OF THE INVENTION

The present invention relates to small molecule compounds and pharmaceutically acceptable salts thereof that are inhibitors of β-site amyloid precursor protein (APP) Cleaving Enzyme 1 (BACE1) and inhibitors of BACE2. This invention relates to inhibiting the production of A-beta peptides that can contribute to the formation of neurological deposits of amyloid protein. The present invention also relates to the treatment of Alzheimer's Disease (AD) and other neurodegenerative and/or neurological disorders, as well as the treatment of diabetes in mammals, including humans. More particularly, this invention relates to thioamidine compounds and pharmaceutically acceptable salts thereof useful for the treatment of neurodegenerative and/or neurological disorders, such as AD and Down's Syndrome, related to A-beta peptide production.

BACKGROUND OF THE INVENTION

Dementia results from a wide variety of distinctive pathological processes. The most common pathological processes causing dementia are Alzheimer's disease ("AD"), cerebral amyloid angiopathy ("CM") and prion-mediated diseases (see, e.g., Haan et al., Clin. Neurol. Neurosurg., 1990, 92(4): 305-310; Glenner et al., J. Neurol. Sci., 1989, 94:1-28). AD is a progressive, neurodegenerative disorder characterized by memory impairment and cognitive dysfunction. AD affects nearly half of all people past the age of 85, the most rapidly growing portion of the United States population. As such, the number of AD patients in the United States is expected to increase from about 4 million to about 14 million by 2050.

The accumulation of amyloid-β (Aβ peptides) is believed to be one of the underlying causes of Alzheimer's Disease (AD), which is the most common cause of cognitive decline in the elderly (Hardy & Allsop, Trends Pharmacol Sci., 1991; 12(10):383-8; Selkoe, Behav. Brain Res., 2008; 192(1):106-13). Aβ, the major protein constituent of amyloid plaques, is derived from sequential cleavage of the type I integral membrane protein, amyloid precursor protein (APP) by two proteases, β- and γ-secretase. Proteolytic cleavage of APP by the β-site APP cleaving enzymes (BACE1 and BACE2) generates a soluble N-terminal ectodomain of APP (sAPPβ) and the C-terminal fragment C99. Subsequent cleavage of the membrane-bound C99 fragment by the γ-secretase liberates the various Aβ peptide species, of which Aβ40 and Aβ42 are the most predominant forms (Vassar et al., J. Neurosci., 2009; 29(41):12787-94; Marks & Berg, Neurochem. Res., 2010; 35:181-210). Therefore, limiting the generation of Aβ directly through inhibition of BACE1 is one of the most attractive approaches for the treatment of AD, as BACE1 inhibitors could effectively inhibit the formation of all predominant Aβ peptides.

In addition, it has been determined that BACE1 knock-out mice had markedly enhanced clearance of axonal and myelin debris from degenerated fibers, accelerated axonal regeneration, and earlier reinnervation of neuromuscular junctions compared with littermate controls. These data suggest BACE1 inhibition as a therapeutic approach to accelerate regeneration and recovery after peripheral nerve damage. (See Farah et al., J. Neurosci., 2011, 31(15): 5744-5754).

Insulin resistance and impaired glucose homoeostasis are important indicators of Type 2 diabetes and are early risk factors of AD. In particular, there is a higher risk of sporadic AD in patients with Type 2 diabetes and AD patients are more prone to Type 2 diabetes (Butler, Diabetes, 53:474-481, 2004.). Recently, it has also been proposed that AD should be reconsidered as Type 3 diabetes (de la Monte, J. Diabetes Sci. Technol., 2008; 2(6):1101-1113). Of special interest is the fact that AD and Type 2 diabetes share common pathogenic mechanisms and possibly treatments (Park S. A., J. Clin. Neurol., 2011; 7:10-18; Raffa, Br. J. Clin. Pharmacol 2011, 71(3):365-376). Elevated plasma levels of Aβ, the product of BACE activities, were recently associated with hyperglycemia and obesity in humans (see Meakin et al., Biochem J., 2012, 441(1):285-96; Martins, Journal of Alzheimer's Disease, 8 (2005) 269-282). Moreover, increased Aβ production prompts the onset of glucose intolerance and insulin resistance in mice (Cózar-Castellano, Am. J. Physiol. Endocrinol. Metab., 302:E1373-E1380, 2012; Delibegovic, Diabetologia (2011) 54:2143-2151). Finally, it is also suggested that circulating Aβ could participate in the development of atherosclerosis in both humans and mice (De Meyer, Atherosclerosis 216 (2011) 54-58; Catapano, Atherosclerosis 210 (2010) 78-87; Roher, Biochimica et Biophysica Acta 1812 (2011) 1508-1514).

Therefore, it is believed that BACE1 levels may play a critical role in glucose and lipid homoeostasis in conditions of chronic nutrient excess. Specifically, BACE1 inhibitors may be potentially useful for increasing insulin sensitivity in skeletal muscle and liver as illustrated by the fact that reduction in BACE1 decreases body weight, protects against diet-induced obesity and enhances insulin sensitivity in mice (see Meakin et al., Biochem. J. 2012, 441(1):285-96). Of equal interest is the identification of LRP1 as a BACE1 substrate and the potential link to atherosclerosis (Strickland, Physiol. Rev., 88: 887-918, 2008; Hyman, J. Biol. Chem., Vol. 280, No. 18, 17777-17785, 2005).

Likewise, inhibition of BACE2 is proposed as a treatment of Type 2 diabetes with the potential to preserve and restore β-cell mass and stimulate insulin secretion in pre-diabetic and diabetic patients (WO2011/020806). BACE2 is a β-cell enriched protease that regulates pancreatic β cell function and mass and is a close homologue of BACE1. Pharmacological inhibition of BACE2 increases β-cell mass and function, leading to the stabilization of Tmem27. (See Esterhazy et al., Cell Metabolism 2011, 14(3): 365-377). It is suggested that BACE2 inhibitors are useful in the treatment and/or prevention of diseases associated with the inhibition of BACE2 (e.g., Type 2 diabetes, with the potential to preserve and restore β-cell mass and stimulate insulin secretion in pre-diabetic and diabetic patients) (WO2011/020806).

Aminodihydrothiazine or thioamidine compounds are described in US2009/0082560, WO 2009/091016 and WO 2010/038686 as useful inhibitors of the β-secretase enzyme. Co-pending PCT application, PCT/IB2012/054198, filed by Pfizer Inc on Aug. 17, 2012, also describes aminodihydrothiazine compounds that are useful inhibitors of the β-secretase enzyme. The present invention is directed to novel thioamidine compounds and their use in the treatment of neurodegenerative diseases, including AD, as well as the treatment of metabolic diseases and conditions such as diabetes and obesity.

SUMMARY OF THE INVENTION

A first embodiment of a first aspect of the present invention is a compound of Formula I:

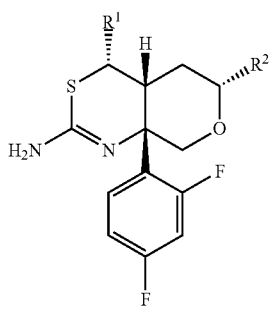

wherein

R¹ is hydrogen or methyl, wherein said methyl is optionally substituted with one to three fluoro;

R² is phenyl substituted with one to five R³;

R³ at each occurrence is independently selected from the group consisting of halogen, hydroxy, cyano, $C_{1-6}$alkyl, $C_{1-6}$alkoxy, $C_{1-6}$alkoxy-$C_{1-6}$alkyl, $C_{3-6}$cycloalkoxy, $C_{3-6}$cycloalkyl-$(CR^{4a}R^{4b})_m$—, $C_{3-6}$cycloalkoxy-$(CR^{4a}R^{4b})_m$—, $C_{3-6}$cycloalkyl-$(CR^{4a}R^{4b})_m$—O— or (4- to 6-membered heterocycloalkyl)-$(CR^{4a}R^{4b})_m$—; wherein said $C_{1-6}$alkyl, $C_{1-6}$alkoxy or $C_{1-6}$alkoxy-$C_{1-6}$alkyl are each optionally substituted with one to three fluoro and wherein said $C_{3-6}$cycloalkyl, $C_{3-6}$cycloalkoxy and (4- to 6-membered heterocycloalkyl) moieties are optionally substituted with one to three substituents independently selected from the group consisting of fluoro, methyl, fluoromethyl, difluoromethyl or trifluoromethyl; or two R³, when attached to adjacent carbons on the phenyl and taken together, can be —(CH$_2$)$_n$—O—, —O—(CH$_2$)$_o$—O— or —(CH$_2$)$_p$—;

$R^{4a}$ and $R^{4b}$ are independently hydrogen, methyl, fluoromethyl, difluoromethyl, trifluoromethyl or methoxy;

m at each occurrence is independently 0, 1 or 2;

n is 2 or 3;

o is 1 or 2; and p is 3 or 4;

or a tautomer thereof or a pharmaceutically acceptable salt of said compound or tautomer.

Another embodiment of the present invention is a pharmaceutical composition comprising compounds of Formula I, or a tautomer thereof or a pharmaceutically acceptable salt of said compound or tautomer, and a pharmaceutically acceptable vehicle, diluent or carrier. The pharmaceutical compositions described herein can be used for inhibiting production of amyloid-β protein and for inhibiting beta-site amyloid precursor protein cleaving enzyme 1 (BACE1); for treating a neurodegenerative disease and, in particular, Alzheimer's Disease; for inhibiting BACE1 and/or BACE2 activity for the therapeutic and/or prophylactic treatment of diseases and disorders characterized by elevated β-amyloid levels, including diabetes or Type 2 diabetes; for increasing insulin sensitivity in skeletal muscle and liver in a mammal, including humans; and for treating and/or preventing obesity.

The present invention is also directed to methods of treatment employing the compounds of Formula I such as:

(1) Methods of inhibiting BACE enzyme activity, by administering a therapeutically effective amount of a thioamidine compound of any of the embodiments of Formula I or a pharmaceutically acceptable salt thereof, and a pharmaceutically acceptable carrier, to a mammal or a patient in need thereof.

(2) Methods for treating conditions or diseases of the central nervous system and neurological disorders in which the β-secretase enzyme is involved (such as migraine; epilepsy; Alzheimer's disease; Parkinson's disease; brain injury; stroke; cerebrovascular diseases (including cerebral arteriosclerosis, cerebral amyloid angiopathy, hereditary cerebral hemorrhage, and brain hypoxia-ischemia); cognitive disorders (including amnesia, senile dementia, HIV-associated dementia, Alzheimer's disease, Huntington's disease, Lewy body dementia, vascular dementia, drug-related dementia, tardive dyskinesia, myoclonus, dystonia, delirium, Pick's disease, Creutzfeldt-Jacob disease, HIV disease, Gilles de la Tourette's syndrome, epilepsy, muscular spasms and disorders associated with muscular spasticity or weakness including tremors, and mild cognitive impairment ("MCI"); mental deficiency (including spasticity, Down syndrome and fragile X syndrome); sleep disorders (including hypersomnia, circadian rhythm sleep disorder, insomnia, parasomnia, and sleep deprivation) and psychiatric disorders such as anxiety (including acute stress disorder, generalized anxiety disorder, social anxiety disorder, panic disorder, post-traumatic stress disorder, agoraphobia, and obsessive-compulsive disorder); factitious disorder (including acute hallucinatory mania); impulse control disorders (including compulsive gambling and intermittent explosive disorder); mood disorders (including bipolar I disorder, bipolar II disorder, mania, mixed affective state, major depression, chronic depression, seasonal depression, psychotic depression, seasonal depression, premenstrual syndrome (PMS), premenstrual dysphoric disorder (PDD), and postpartum depression); psychomotor disorder; psychotic disorders (including schizophrenia, schizoaffective disorder, schizophreniform, and delusional disorder); drug dependence (including narcotic dependence, alcoholism, amphetamine dependence, cocaine addiction, nicotine dependence, and drug withdrawal syndrome); eating disorders (including anorexia, bulimia, binge eating disorder, hyperphagia, obesity, compulsive eating disorders and pagophagia); sexual dysfunction disorders; urinary incontinence; neuronal damage disorders (including ocular damage, retinopathy or macular degeneration of the eye, tinnitus, hearing impairment and loss, and brain edema), nerve injury treatment (including accelerating regeneration and recovery after peripheral nerve damage) and pediatric psychiatric disorders (including attention deficit disorder, attention deficit/hyperactive disorder, conduct disorder, and autism) in a mammal, preferably a human, comprising administering to said mammal a therapeutically effective amount of a compound of Formula I or pharmaceutically acceptable salt thereof. The compounds of Formula I may also be useful for improving memory (both short-term and long-term) and learning ability. The text revision of the fourth edition of the Diagnostic and Statistical Manual of Mental Disorders (DSM-IV-TR) (2000, American Psychiatric Association, Washington, D.C.) provides a diagnostic tool for identifying many of the disorders described herein. The skilled artisan will recognize that there are alternative nomenclatures, nosologies, and classification systems for disorders described herein, including those as described in the DMS-IV-TR, and that terminology and classification systems evolve with medical scientific progress;

(3) Methods for treating a neurological disorder (such as migraine; epilepsy; Alzheimer's disease; Parkinson's disease; Niemann-Pick type C; brain injury; stroke; cerebrovascular disease; cognitive disorder; sleep disorder) or a psychiatric disorder (such as anxiety; factitious disorder; impulse control disorder; mood disorder; psychomotor disorder; psychotic disorder; drug dependence; eating disorder; and pediatric psychiatric disorder) in a mammal, preferably a human, comprising administering to said mammal a therapeutically effective amount of a compound of Formula I or pharmaceutically acceptable salt thereof;

(4) Methods for the treatment (e.g., delaying the progression or onset) of diabetes or diabetes-related disorders including Type 1 and Type 2 diabetes, impaired glucose tolerance, insulin resistance, hyperglycemia, and diabetic complications such as atherosclerosis, coronary heart disease, stroke, peripheral vascular disease, nephropathy, hypertension, neuropathy, and retinopathy;

(5) Methods for the treatment of obesity co-morbidities, such as metabolic syndrome. Metabolic syndrome includes diseases, conditions or disorders such as dyslipidemia, hypertension, insulin resistance, diabetes (e.g., Type 2 diabetes), coronary artery disease and heart failure. For more detailed information on metabolic syndrome, see, e.g., Zimmet, P. Z. et al., "The Metabolic Syndrome: Perhaps an Etiologic Mystery but Far From a Myth—Where Does the International Diabetes Federation Stand?," Medscape Diabetes & Endocrinology, 7(2), (2005); and Alberti, K. G. et al., "The Metabolic Syndrome—A New Worldwide Definition," Lancet, 366, 1059-62 (2005); and (6) Methods for the treatment of nonalcoholic fatty liver disease (NAFLD) and hepatic insulin resistance;

The present invention is also directed to combination therapies wherein the compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided;

All patents, patent applications and references referred to herein are hereby incorporated by reference in their entirety.

Other features and advantages of this invention will be apparent from this specification and the appendent claims which describe the invention. It is to be understood that both the foregoing and the following detailed description are exemplary only and are not restrictive of the invention as claimed.

DETAILED DESCRIPTION OF THE INVENTION

The present invention may be understood more readily by reference to the following detailed description of exemplary embodiments of the invention and the examples included therein. It is to be understood that this invention is not limited to specific methods of synthesis, which may of course vary. It is also to be understood that the terminology used herein is for the purpose of describing particular embodiments only and is not intended to be limiting.

In this specification and in the claims that follow, reference will be made to a number of terms that shall be defined to have the following meanings:

As used herein, "eating disorders" refer to illnesses in which the patient suffers disturbances in his/her eating behaviors and related thoughts and emotions. Representative examples of obesity-related eating disorders include overeating, bulimia, binge-eating disorder, compulsive dieting, nocturnal sleep-related eating disorder, pica, Prader-Willi syndrome, and night-eating syndrome.

"Patient" refers to warm-blooded animals such as, for example, guinea pigs, mice, rats, gerbils, cats, rabbits, dogs, cattle, goats, sheep, horses, monkeys, chimpanzees, and humans.

The term "pharmaceutically acceptable" means the substance or composition must be compatible, chemically and/or toxicologically, with the other ingredients comprising a formulation, and/or the mammal being treated therewith.

The term "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "treating", as used herein, unless otherwise indicated, means reversing, alleviating, inhibiting the progress of, delaying the progression of, delaying the onset of, or preventing the disorder or condition to which such term applies, or one or more symptoms of such disorder or condition. The term "treatment", as used herein, unless otherwise indicated, refers to the act of treating as "treating" is defined immediately above. The term "treating" also includes adjuvant and neo-adjuvant treatment of a subject. For the avoidance of doubt, reference herein to "treatment" includes reference to curative, palliative and prophylactic treatment, and to the administration of a medicament for use in such treatment.

The term "alkyl" refers to a linear or branched-chain saturated hydrocarbyl substituent (i.e., a substituent obtained from a hydrocarbon by removal of a hydrogen); in one embodiment containing from one to six carbon atoms. Non-limiting examples of such substituents include methyl, ethyl, propyl (including n-propyl and isopropyl), butyl (including n-butyl, isobutyl, sec-butyl and tert-butyl), pentyl, isoamyl, hexyl and the like.

The term "alkoxy" refers to a linear or branched-chain saturated hydrocarbyl substituent attached to an oxygen radical (i.e., a substituent obtained from a hydrocarbon alcohol by removal of the hydrogen from the OH); in one embodiment containing from one to six carbon atoms. Non-limiting examples of such substituents include methoxy, ethoxy, propoxy (including n-propoxy and isopropoxy), butoxy (including n-butoxy, isobutoxy, sec-butoxy and tert-butoxy), pentoxy, hexoxy and the like.

In some instances, the number of carbon atoms in a hydrocarbyl substituent (i.e., alkyl, cycloalkyl, etc.) is indicated by the prefix "$C_x$-$C_y$-" or "$C_{x-y}$", wherein x is the minimum and y is the maximum number of carbon atoms in the substituent. Thus, for example, "$C_1$-$C_6$-alkyl" or "$C_{1-6}$ alkyl" refers to an alkyl substituent containing from 1 to 6 carbon atoms. Illustrating further, $C_3$-$C_6$cycloalkyl or $C_{3-6}$-cycloalkyl refers to saturated cycloalkyl group containing from 3 to 6 carbon ring atoms.

The term "cycloalkyl" refers to a carbocyclic substituent obtained by removing a hydrogen from a saturated carbocyclic molecule, for example one having three to six carbon atoms. The term "$C_{3-6}$cycloalkyl" means a radical of a three to six membered ring which includes the groups cyclopropyl, cyclobutyl, cyclopentyl and cyclohexyl. The term "$C_{3-6}$cycloalkoxy" refers to a three to six membered cycloalkyl group attached to an oxygen radical. Examples include cyclopropoxy, cyclobutoxy, cyclopentoxy and cyclohexoxy.

In some instances, the number of atoms in a cyclic substituent containing one or more heteroatoms (i.e., heteroaryl or heterocycloalkyl) is indicated by the prefix "x- to y-membered", wherein x is the minimum and y is the maximum number of atoms forming the cyclic moiety of the substituent.

Thus, for example, "4- to 6-membered heterocycloalkyl" refers to a heterocycloalkyl containing from 4 to 6 atoms, including one to three heteroatoms, in the cyclic moiety of the heterocycloalkyl. The heteroatoms present in these ring systems are selected from N, O and S.

The term "hydroxy" or "hydroxyl" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "halo" or "halogen" refers to fluorine (which may be depicted as —F), chlorine (which may be depicted as —Cl), bromine (which may be depicted as —Br), or iodine (which may be depicted as —I).

The term "heterocycloalkyl" refers to a substituent obtained by removing a hydrogen from a saturated or partially saturated ring structure containing a total of the specified number of atoms, such as 4 to 6 ring atoms, wherein at least one of the ring atoms is a heteroatom (i.e., oxygen, nitrogen, or sulfur), with the remaining ring atoms being independently selected from the group consisting of carbon, oxygen, nitrogen, and sulfur. In a group that has a heterocycloalkyl substituent, the ring atom of the heterocycloalkyl substituent that is bound to the group may be a nitrogen heteroatom, or it may be a ring carbon atom. Similarly, if the heterocycloalkyl substituent is in turn substituted with a group or substituent, the group or substituent may be bound to a nitrogen heteroatom, or it may be bound to a ring carbon atom. In a certain embodiment the heterocycloalkyl can be fused to the phenyl group in $R^2$.

The term "phenyl" refers to a substituent obtained by removing a hydrogen from a benzene ring. In the case of the present invention the phenyl is substituted with one to three $R^3$ groups which are as defined herein.

If substituents are described as "independently" having more than one variable, each instance of a substituent is selected independent of the other(s) from the list of variables available. Each substituent therefore may be identical to or different from the other substituent(s).

If substituents are described as being "independently selected" from a group, each instance of a substituent is selected independent of the other(s). Each substituent therefore may be identical to or different from the other substituent(s).

As used herein, the term "Formula I" may be hereinafter referred to as a "compound(s) of the invention," "the present invention," and "compound of Formula I." Such terms are also defined to include all forms of the compound of Formula I, including hydrates, solvates, isomers, crystalline and non-crystalline forms, isomorphs, polymorphs, and metabolites thereof. For example, the compounds of the invention, or pharmaceutically acceptable salts thereof, may exist in unsolvated and solvated forms. When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

The compounds of the invention may exist as clathrates or other complexes. Included within the scope of the invention are complexes such as clathrates, drug-host inclusion complexes wherein the drug and host are present in stoichiometric or non-stoichiometric amounts. Also included are complexes of the compounds of the invention containing two or more organic and/or inorganic components, which may be in stoichiometric or non-stoichiometric amounts. The resulting complexes may be ionized, partially ionized, or non-ionized. For a review of such complexes, see J. Pharm. Sci., 64 (8), 1269-1288 by Haleblian (August 1975).

The compounds of the invention have asymmetric carbon atoms. The carbon-carbon bonds of the compounds of the invention may be depicted herein using a solid line (———), a solid wedge (▬▬▬), or a dotted wedge (··⸱⸱⸱⸱⸱). The use of a solid line to depict bonds to asymmetric carbon atoms is meant to indicate that all possible stereoisomers (e.g., specific enantiomers, racemic mixtures, etc.) at that carbon atom are included. The use of either a solid or dotted wedge to depict bonds to asymmetric carbon atoms is meant to indicate that only the stereoisomer shown is meant to be included. It is possible that compounds of Formula I may contain more than one asymmetric carbon atom. In those compounds, the use of a solid line to depict bonds to asymmetric carbon atoms is meant to indicate that all possible stereoisomers are meant to be included. For example, unless stated otherwise, it is intended that the compounds of Formula I can exist as enantiomers and diastereomers or as racemates and mixtures thereof. The use of a solid line to depict bonds to one or more asymmetric carbon atoms in a compound of Formula I and the use of a solid or dotted wedge to depict bonds to other asymmetric carbon atoms in the same compound is meant to indicate that a mixture of diastereomers is present.

Stereoisomers of Formula I include cis and trans isomers, optical isomers such as R and S enantiomers, diastereomers, geometric isomers, rotational isomers, conformational isomers, and tautomers of the compounds of the invention, including compounds exhibiting more than one type of isomerism; and mixtures thereof (such as racemates and diastereomeric pairs). Also included are acid addition or base addition salts wherein the counterion is optically active, for example, D-lactate or L-lysine, or racemic, for example, DL-tartrate or DL-arginine.

When any racemate crystallizes, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

The compounds of Formula I may exhibit the phenomenon of tautomerism; such tautomers are also regarded as compounds of the invention. For example, the compounds of Formula I may exist in several tautomeric forms, including the 2-aminodihydrothiazine form, Ia, and the 2-imino-tetrahydrothiazine form, Ib. All such tautomeric forms, and mixtures thereof, are included within the scope of compounds of Formula I. Tautomers exist as mixtures of a tautomeric set in solution. In solid form, usually one tautomer predominates. Even though one tautomer may be described, the present invention includes all tautomers of the compounds of Formula I and salts thereof. Examples of tautomers are described by the compounds of Formula Ia and Ib and, collectively and generically, are referred to as compounds of Formula I.

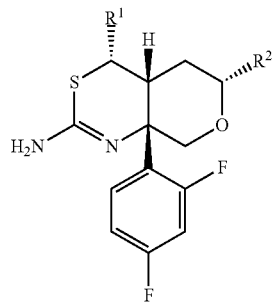

Ia

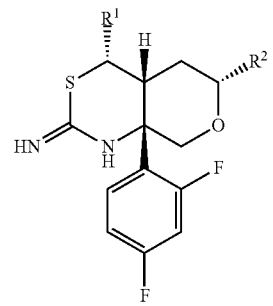

Ib

The compounds of this invention may be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound of Formula I with an acid whose anion, or a base whose cation, is generally considered suitable for human consumption. Pharmaceutically acceptable salts are particularly useful as products of the methods of the present invention because of their greater aqueous solubility relative to the parent compound. For use in medicine, the salts of the compounds of this invention are non-toxic "pharmaceutically acceptable salts." Salts encompassed within the term "pharmaceutically acceptable salts" refer to non-toxic salts of the compounds of this invention which are generally prepared by reacting the free base with a suitable organic or inorganic acid.

Suitable pharmaceutically acceptable acid addition salts of the compounds of the present invention, when possible, include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclic, carboxylic, and sulfonic classes of organic acids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, and undecanoate.

Furthermore, where the compounds of the invention carry an acidic moiety, suitable pharmaceutically acceptable salts thereof may include the lighter alkali metal salts, i.e., sodium or potassium salts; alkaline earth metal salts, e.g., calcium or magnesium salts; and salts formed with suitable organic ligands, e.g., quaternary ammonium salts. In another embodiment, base salts are formed from bases which form non-toxic salts, including aluminum, arginine, benzathine, choline, diethylamine, diolamine, glycine, lysine, meglumine, olamine, tromethamine and zinc salts.

Organic salts may be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups may be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In one embodiment, hemisalts of acids and bases may also be formed, for example, hemisulfate and hemicalcium salts.

Also within the scope of the present invention are so-called "prodrugs" of the compound of the invention. Thus, certain derivatives of the compound of the invention which may have little or no pharmacological activity themselves can, when administered into or onto the body, be converted into the compound of the invention having the desired activity, for example, by hydrolytic cleavage. Such derivatives are referred to as "prodrugs." Further information on the use of prodrugs may be found in "Pro-drugs as Novel Delivery Systems, Vol. 14, ACS Symposium Series (T. Higuchi and V. Stella) and "Bioreversible Carriers in Drug Design," Pergamon Press, 1987 (ed. E. B. Roche, American Pharmaceutical Association). Prodrugs in accordance with the invention can, for example, be produced by replacing appropriate functionalities present in the compounds of any of Formula I with certain moieties known to those skilled in the art as "promoieties" as described, for example, in "Design of Prodrugs" by H. Bundgaard (Elsevier, 1985).

The present invention also includes isotopically labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorus, sulfur, fluorine and chlorine, such as $^2H$, $^3H$, $^{13}C$, $^{11}C$, $^{14}C$, $^{15}N$, $^{18}O$, $^{17}O$, $^{32}P$, $^{35}S$, $^{18}F$, and $^{36}Cl$, respectively. Compounds of the present invention, prodrugs thereof, and pharmaceutically acceptable salts of said compounds or of said prodrugs that contain the aforementioned isotopes and/or other isotopes of other atoms are within the scope of this invention. Certain isotopically labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of Formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

A second embodiment of the first aspect of the present invention is the compound of the first embodiment of the first aspect wherein $R^2$ is

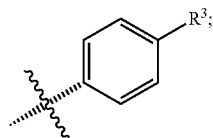

$R^3$ is selected from the group consisting of chloro, fluoro, cyano, methyl, difluoromethyl, trifluoromethyl, methoxy, ethoxy, methoxymethyl, and 1-methoxyethyl; or a tautomer thereof or a pharmaceutically acceptable salt of said compound or tautomer.

A third embodiment of the first aspect of the present invention is the compound of the second embodiment wherein $R^1$ is hydrogen; or a tautomer thereof or a pharmaceutically acceptable salt of said compound or tautomer.

A fourth embodiment of the first aspect of the present invention is the compound of the second embodiment wherein $R^1$ is methyl; or a tautomer thereof or a pharmaceutically acceptable salt of said compound or tautomer.

A fifth embodiment of the first aspect of the present invention is the compound of the third embodiment selected from the group consisting of: (4aR,6R,8aS)-8a-(2,4-difluorophenyl)-6-(4-fluorophenyl)-4,4a,5,6,8,8a-hexahydropyrano[3,4-d][1,3]thiazin-2-amine; (4aR,6R,8aS)-6-(4-chlorophenyl)-8a-(2,4-difluorophenyl)-4,4a,5,6,8,8a-hexahydropyrano[3,4-d][1,3]thiazin-2-amine; (4aR,6R,8aS)-8a-(2,4-difluorophenyl)-6-[4-(trifluoromethyl)phenyl]-4,4a,5,6,8,8a-hexahydropyrano[3,4-d][1,3]thiazin-2-amine; (4aR,6R,8aS)-8a-(2,4-difluorophenyl)-6-[4-(trifluoromethoxy)phenyl]-4,4a,5,6,8,8a-hexahydropyrano[3,4-d][1,3]thiazin-2-amine; (4aR,6R,8aS)-8a-(2,4-difluorophenyl)-6-(4-methoxyphenyl)-4,4a,5,6,8,8a-hexahydropyrano[3,4-d][1,3]thiazin-2-amine; (4aR,6R,8aS)-8a-(2,4-difluorophenyl)-6-(4-ethoxyphenyl)-4,4a,5,6,8,8a-hexahydropyrano[3,4-d][1,3]thiazin-2-amine; (4aR,6R,8aS)-8a-(2,4-difluorophenyl)-6-[4-(methoxymethyl)phenyl]-4,4a,5,6,8,8a-hexahydropyrano[3,4-d][1,3]thiazin-2-amine; (4aR,6R,8aS)-8a-(2,4-difluorophenyl)-6-[4-(1-methoxyethyl)phenyl]-4,4a,5,6,8,8a-hexahydropyrano[3,4-d][1,3]thiazin-2-amine; 4-[(4aR,6R,8aS)-2-amino-8a-(2,4-difluorophenyl)-4,4a,5,6,8,8a-hexahydropyrano[3,4-d][1,3]thiazin-6-yl]benzonitrile; and (4aR,6R,8aS)-8a-(2,4-difluorophenyl)-6-[4-(difluoromethyl)phenyl]-4,4a,5,6,8,8a-hexahydropyrano[3,4-d][1,3]thiazin-2-amine; or a tautomer thereof or a pharmaceutically acceptable salt of said compound or tautomer.

A sixth embodiment of the first aspect of the present invention is the compound of the fourth embodiment selected from the group consisting of: (4R,4aR,6R,8aS)-8a-(2,4-difluorophenyl)-6-(4-fluorophenyl)-4-methyl-4,4a,5,6,8,8a-hexahydropyrano[3,4-d][1,3]thiazin-2-amine; and (4R,4aR,6R,8aS)-8a-(2,4-difluorophenyl)-6-(4-cyanophenyl)-4-methyl-4,4a,5,6,8,8a-hexahydropyrano[3,4-d][1,3]thiazin-2-amine; or a tautomer thereof or a pharmaceutically acceptable salt of said compound or tautomer.

A seventh embodiment of the first aspect of the present invention is the compound of the first embodiment wherein $R^1$ is hydrogen or methyl;

$R^2$ is

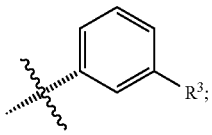

$R^3$ is selected from fluoro, cyano, trifluoromethyl or methoxymethyl; or a tautomer thereof or a pharmaceutically acceptable salt of said compound or tautomer.

An eighth embodiment of a first aspect of the present invention is the compound of the seventh embodiment selected from the group consisting of: (4aR,6R,8aS)-8a-(2,4-difluorophenyl)-6-(3-fluorophenyl)-4,4a,5,6,8,8a-hexahydropyrano[3,4-d][1,3]thiazin-2-amine; (4aR,6R,8aS)-8a-(2,4-difluorophenyl)-6-[3-(trifluoromethyl)phenyl]-4,4a,5,6,8,8a-hexahydropyrano[3,4-d][1,3]thiazin-2-amine; (4aR,6R,8aS)-8a-(2,4-difluorophenyl)-6-[3-(methoxymethyl)phenyl]-4,4a,5,6,8,8a-hexahydropyrano[3,4-d][1,3]thiazin-2-amine; 3-[(4aR,6R,8aS)-2-amino-8a-(2,4-difluorophenyl)-4,4a,5,6,8,8a-hexahydropyrano[3,4-d][1,3]thiazin-6-yl]benzonitrile; and (4R,4aR,6R,8aS)-8a-(2,4-difluorophenyl)-6-(3-cyanophenyl)-4-methyl-4,4a,5,6,8,8a-hexahydropyrano[3,4-d][1,3]thiazin-2-amine; or a tautomer thereof or a pharmaceutically acceptable salt of said compound or tautomer.

A ninth embodiment of a first aspect of the present invention is the compound of the first embodiment wherein $R^1$ is hydrogen; and $R^2$ is

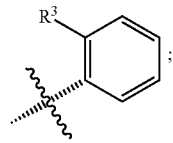

or a tautomer thereof or a pharmaceutically acceptable salt of said compound or tautomer.

A tenth embodiment of a first aspect of the present invention is the compound of the ninth embodiment selected from (4aR,6R,8aS)-8a-(2,4-difluorophenyl)-6-(2-fluorophenyl)-4,4a,5,6,8,8a-hexahydropyrano[3,4-d][1,3]thiazin-2-amine; and (4aR,6R,8aS)-8a-(2,4-difluorophenyl)-6-(2-methoxyphenyl)-4,4a,5,6,8,8a-hexahydropyrano[3,4-d][1,3]thiazin-2-amine;

or a tautomer thereof or pharmaceutically acceptable salt of said compound or tautomer.

An eleventh embodiment of a first aspect of the present invention is the compound of the first aspect wherein $R^1$ is hydrogen; and $R^2$ is

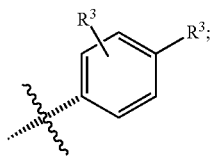

or a tautomer thereof or a pharmaceutically acceptable salt of said compound or tautomer.

A twelfth embodiment of a first aspect of the present invention is the compound of the eleventh embodiment wherein $R^3$ at each occurrence is independently selected from fluoro, methyl or methoxy; or the two $R^3$, when attached to adjacent carbons on the phenyl and taken together, can be —$(CH_2)_n$—O— or —O—$(CH_2)_o$—O—; n is 2; and o is 1; or a tautomer thereof or a pharmaceutically acceptable salt of said compound or tautomer.

A thirteenth embodiment of a first aspect of the present invention is the compound of the twelfth embodiment selected from the group consisting of: (4aR,6R,8aS)-6,8a-bis(2,4-difluorophenyl)-4,4a,5,6,8,8a-hexahydropyrano[3,4-d][1,3]thiazin-2-amine; (4aR,6R,8aS)-8a-(2,4-difluorophenyl)-6-(3,4-difluorophenyl)-4,4a,5,6,8,8a-hexahydropyrano[3,4-d][1,3]thiazin-2-amine; (4aR,6R,8aS)-8a-(2,4-difluorophenyl)-6-(4-fluoro-3-methylphenyl)-4,4a, 5,6,8,8a-hexahydropyrano[3,4-d][1,3]thiazin-2-amine; (4aR,6R,8aS)-8a-(2,4-difluorophenyl)-6-(3-fluoro-4-methylphenyl)-4,4a,5,6,8,8a-hexahydropyrano[3,4-d][1,3]thiazin-2-amine; (4aR,6R,8aS)-8a-(2,4-difluorophenyl)-6-(4-fluoro-3-methoxyphenyl)-4,4a,5,6,8,8a-hexahydropyrano[3,4-d][1,3]thiazin-2-amine; (4aR,6R,8aS)-8a-(2,4-difluorophenyl)-6-(3-fluoro-4-methoxyphenyl)-4,4a,5,6,8,8a-hexahydropyrano[3,4-d][1,3]thiazin-2-amine; (4aR,6R,8aS)-8a-(2,4-difluorophenyl)-6-(2-fluoro-4-methoxyphenyl)-4,4a,5,6,8,8a-hexahydropyrano[3,4-d][1,3]thiazin-2-amine; (4aR,6R,8aS)-8a-(2,4-difluorophenyl)-6-(2,3-dihydro-1-benzofuran-5-yl)-4,4a,5,6,8,8a-hexahydropyrano[3,4-d][1,3]thiazin-2-amine; and (4aR,6R,8aS)-6-(1,3-benzodioxol-5-yl)-8a-(2,4-difluorophenyl)-4,4a, 5,6,8,8a-hexahydropyrano[3,4-d][1,3]thiazin-2-amine; or a tautomer thereof or a pharmaceutically acceptable salt of said compound or tautomer.

A fourteenth embodiment of a first aspect of the present invention is the compound of the first embodiment wherein $R^1$ is hydrogen;

$R^2$ is

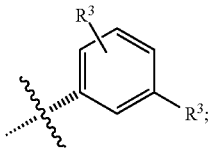

and
$R^3$ at each occurrence is independently selected from fluoro, methyl and methoxy; or a tautomer thereof or a pharmaceutically acceptable salt of said compound or tautomer.

A fifteenth embodiment of the first aspect of the present invention is the compound of the fourteenth embodiment selected from the group consisting of (4aR,6R,8aS)-8a-(2,4-difluorophenyl)-6-(3-fluoro-5-methylphenyl)-4,4a,5,6,8,8a-hexahydropyrano[3,4-d][1,3]thiazin-2-amine; (4aR,6R,8aS)-8a-(2,4-difluorophenyl)-6-(2-fluoro-5-methylphenyl)-4,4a,5,6,8,8a-hexahydropyrano[3,4-d][1,3]thiazin-2-amine; and (4aR,6R,8aS)-8a-(2,4-difluorophenyl)-6-(3-fluoro-5-methoxyphenyl)-4,4a,5,6,8,8a-hexahydropyrano[3,4-d][1,3]thiazin-2-amine; or a tautomer thereof or a pharmaceutically acceptable salt of said compound or tautomer.

Yet another embodiment of the present invention is a compound of Formula I wherein $R^1$ is hydrogen or methyl, wherein said methyl is optionally substituted with one to three fluoro; $R^2$ is phenyl which is fused to a 4- to 6-membered heterocycloalkyl group; wherein said 4- to 6-membered heterocycloalkyl group contains one to two heteroatoms selected from N, O and S; and wherein said phenyl can be further substituted with one to two $R^3$; and $R^3$, $R^{4a}$ and $R^{4b}$ are as described above for the first embodiment; or a tautomer thereof or a pharmaceutically acceptable salt of said compound or tautomer.

A first embodiment of a second aspect of the present invention is a pharmaceutical composition comprising a therapeutically effective amount of a compound of any one of the first to fifteenth embodiments of the first aspect of the present invention, or a tautomer thereof or a pharmaceutically acceptable salt of said compound or tautomer, and a pharmaceutically acceptable vehicle, diluent or carrier.

Further embodiments of the present invention include methods of treatment employing the compounds of the present invention.

A first embodiment of a third aspect of the present invention is a method of inhibiting production of amyloid-protein in a patient; the method comprising administering a therapeutically effective amount of a compound according to any one of the first through fifteenth embodiments of the first aspect of the present invention, or a tautomer thereof or a pharmaceutically acceptable salt of said compound or tautomer to a patient in need of inhibition of production of amyloid-protein.

A second embodiment of a third aspect of the present invention is a method of inhibiting beta-site amyloid precursor protein cleaving enzyme 1 (BACE1) in a patient, the method comprising administering a therapeutically effective amount of a compound according to any one of the first through fifteenth embodiments of the first aspect of the present invention, or a tautomer thereof or a pharmaceutically acceptable salt of said compound or tautomer to a patient in need of inhibition of beta-site amyloid precursor protein cleaving enzyme 1 (BACE1).

A third embodiment of a third aspect of the present invention is a method for treating a neurodegenerative disease in a patient, the method comprising administering a therapeutically effective amount of a compound according to any one of the first through fifteenth embodiments of the first aspect of the present invention, or a tautomer thereof or a pharmaceutically acceptable salt of said compound or tautomer to a patient in need of treatment thereof.

A fourth embodiment of a third aspect of the present invention is the method of the third embodiment of the third aspect wherein the neurodegenerative disease is Alzheimer's Disease.

A fifth embodiment of a third aspect of the present invention is a method of treating or preventing diabetes in a patient, the method comprising administering a therapeutically effective amount of a compound according to any one of first through fifteenth embodiments of the first aspect of the present invention, or a tautomer thereof or a pharmaceutically acceptable salt of said compound or tautomer to a patient in need of treatment or prevention thereof.

A sixth embodiment of a third aspect of the present invention is the method of the fifth embodiment of the third aspect wherein the diabetes is Type 2 diabetes.

Further embodiments of the present invention include the use of a compound according to any one of first through fifteenth embodiments of the first aspect of the present invention in the preparation of a medicament useful for treating the conditions, diseases and disorders as described herein.

Typically, a compound of the invention is administered in an amount effective to treat a condition as described herein. The compounds of the invention are administered by any suitable route in the form of a pharmaceutical composition adapted to such a route, and in a dose effective for the treatment intended. Therapeutically effective doses of the compounds required to treat the progress of the medical condition are readily ascertained by one of ordinary skill in the art using preclinical and clinical approaches familiar to the medicinal arts.

The compounds of the invention may be administered orally. Oral administration may involve swallowing, so that the compound enters the gastrointestinal tract, or buccal or sublingual administration may be employed, by which the compound enters the blood stream directly from the mouth.

In another embodiment, the compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

In another embodiment, the compounds of the invention may also be administered topically to the skin or mucosa, that is, dermally or transdermally. In another embodiment, the compounds of the invention can also be administered intranasally or by inhalation. In another embodiment, the compounds of the invention may be administered rectally or vaginally. In another embodiment, the compounds of the invention may also be administered directly to the eye or ear.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regimen may vary widely. Dosage levels of the order from about 0.01 mg to about 100 mg per kilogram of body weight per day are useful in the treatment of the above-indicated conditions. In one embodiment, the total daily dose of a compound of the invention (administered in single or divided doses) is typically from about 0.01 to about 100 mg/kg. In another embodiment, total daily dose of the compound of the invention is from about 0.1 to about 50 mg/kg, and in another embodiment, from about 0.5 to about 30 mg/kg (i.e., mg compound of the invention per kg body weight). In one embodiment, dosing is from 0.01 to 10 mg/kg/day. In another embodiment, dosing is from 0.1 to 1.0 mg/kg/day. Dosage unit compositions may contain such amounts or submultiples thereof to make up the daily dose. In many instances, the administration of the compound will be repeated a plurality of times in a day (typically no greater than 4 times). Multiple doses per day typically may be used to increase the total daily dose, if desired.

For oral administration, the compositions may be provided in the form of tablets containing from about 0.01 mg to about 500 mg of the active ingredient, or in another embodiment, from about 1 mg to about 100 mg of active ingredient. Intravenously, doses may range from about 0.1 to about 10 mg/kg/minute during a constant rate infusion.

Suitable subjects according to the present invention include mammalian subjects. Mammals according to the present invention include, but are not limited to, canine, feline, bovine, caprine, equine, ovine, porcine, rodents, lagomorphs, primates, and the like, and encompass mammals in utero. In one embodiment, humans are suitable subjects. Human subjects may be of either gender and at any stage of development.

In another embodiment, the invention comprises the use of one or more compounds of the invention for the preparation of a medicament for the treatment of the conditions recited herein.

For the treatment of the conditions referred to above, the compound of the invention can be administered as compound per se. Alternatively, pharmaceutically acceptable salts are suitable for medical applications because of their greater aqueous solubility relative to the parent compound.

In another embodiment, the present invention comprises pharmaceutical compositions. Such pharmaceutical compositions comprise a compound of the invention presented with a pharmaceutically acceptable carrier. The carrier can be a solid, a liquid, or both, and may be formulated with the compound as a unit-dose composition, for example, a tablet, which can contain from 0.05% to 95% by weight of the active compounds. A compound of the invention may be coupled with suitable polymers as targetable drug carriers. Other pharmacologically active substances can also be present.

The compounds of the present invention may be administered by any suitable route, preferably in the form of a pharmaceutical composition adapted to such a route, and in a dose effective for the treatment intended. The active compounds and compositions, for example, may be administered orally, rectally, parenterally, or topically.

Oral administration of a solid dose form may be, for example, presented in discrete units, such as hard or soft capsules, pills, cachets, lozenges, or tablets, each containing a predetermined amount of at least one compound of the present invention. In another embodiment, the oral administration may be in a powder or granule form. In another embodiment, the oral dose form is sub-lingual, such as, for example, a lozenge. In such solid dosage forms, the compounds of Formula I are ordinarily combined with one or more adjuvants. Such capsules or tablets may contain a controlled-release formulation. In the case of capsules, tablets, and pills, the dosage forms also may comprise buffering agents or may be prepared with enteric coatings.

In another embodiment, oral administration may be in a liquid dose form. Liquid dosage forms for oral administration include, for example, pharmaceutically acceptable emulsions, solutions, suspensions, syrups, and elixirs containing inert diluents commonly used in the art (e.g., water). Such compositions also may comprise adjuvants, such as wetting, emulsifying, suspending, flavoring (e.g., sweetening), and/or perfuming agents.

In another embodiment, the present invention comprises a parenteral dose form. "Parenteral administration" includes, for example, subcutaneous injections, intravenous injections, intraperitoneal injections, intramuscular injections, intrasternal injections, and infusion. Injectable preparations (e.g., sterile injectable aqueous or oleaginous suspensions) may be formulated according to the known art using suitable dispersing, wetting agents, and/or suspending agents.

In another embodiment, the present invention comprises a topical dose form. "Topical administration" includes, for example, transdermal administration, such as via transdermal patches or iontophoresis devices, intraocular administration, or intranasal or inhalation administration. Compositions for topical administration also include, for example, topical gels, sprays, ointments, and creams. A topical formulation may include a compound which enhances absorption or penetration of the active ingredient through the skin or other affected areas. When the compounds of this invention are administered by a transdermal device, administration will be accomplished using a patch either of the reservoir and porous membrane type or of a solid matrix variety. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated; see, for example, J. Pharm. Sci., 88 (10), 955-958, by Finnin and Morgan (October 1999).

Formulations suitable for topical administration to the eye include, for example, eye drops wherein the compound of this invention is dissolved or suspended in a suitable carrier. A typical formulation suitable for ocular or aural administration may be in the form of drops of a micronized suspension or solution in isotonic, pH-adjusted, sterile saline. Other formulations suitable for ocular and aural administration include ointments, biodegradable (e.g., absorbable gel sponges, collagen) and non-biodegradable (e.g., silicone) implants, wafers, lenses and particulate or vesicular systems, such as niosomes or liposomes. A polymer such as cross-linked polyacrylic acid, polyvinyl alcohol, hyaluronic acid, a cellulosic polymer, for example, hydroxypropylmethyl cellulose, hydroxyethyl cellulose, or methyl cellulose, or a heteropolysaccharide polymer, for example, gelan gum, may be incorporated together with a preservative, such as benzalkonium chloride. Such formulations may also be delivered by iontophoresis.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant. Formulations suitable for intranasal administration are typically administered in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurized container, pump, spray, atomizer (preferably an atomizer using electrohydrodynamics to produce a fine mist), or nebulizer, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

In another embodiment, the present invention comprises a rectal dose form. Such rectal dose form may be in the form of, for example, a suppository. Cocoa butter is a traditional suppository base, but various alternatives may be used as appropriate.

Other carrier materials and modes of administration known in the pharmaceutical art may also be used. Pharmaceutical compositions of the invention may be prepared by any of the well-known techniques of pharmacy, such as effective formulation and administration procedures. The above considerations in regard to effective formulations and administration procedures are well known in the art and are described in standard textbooks. Formulation of drugs is discussed in, for example, Hoover, John E., Remington's Pharmaceutical Sciences, Mack Publishing Co., Easton, Pa., 1975; Liberman et al., Eds., Pharmaceutical Dosage Forms, Marcel Decker, New York, N. Y., 1980; and Kibbe et al., Eds., Handbook of Pharmaceutical Excipients ($3^{rd}$ Ed.), American Pharmaceutical Association, Washington, 1999.

The compounds of the present invention can be used, alone or in combination with other therapeutic agents, in the treatment of various conditions or disease states. The compound(s) of the present invention and other therapeutic agent(s) may be may be administered simultaneously (either in the same dosage form or in separate dosage forms) or sequentially.

Two or more compounds may be administered simultaneously, concurrently or sequentially. Additionally, simultaneous administration may be carried out by mixing the compounds prior to administration or by administering the compounds at the same point in time but at different anatomic sites or using different routes of administration.

The phrases "concurrent administration," "co-administration," "simultaneous administration," and "administered simultaneously" mean that the compounds are administered in combination.

The present invention includes the use of a combination of a BACE inhibitor compound as provided in Formula I and one or more additional pharmaceutically active agent(s). If a combination of active agents is administered, then they may be administered sequentially or simultaneously, in separate dosage forms or combined in a single dosage form. Accordingly, the present invention also includes pharmaceutical compositions comprising an amount of: (a) a first agent comprising a compound of Formula I or a pharmaceutically acceptable salt of the compound; (b) a second pharmaceutically active agent; and (c) a pharmaceutically acceptable carrier, vehicle or diluent.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include, without limitation:

(i) anti-obesity agents (including appetite suppressants), include gut-selective MTP inhibitors (e.g., dirlotapide, mitratapide and implitapide, CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonists (e.g., compounds described in U.S. Pat. No. 6,818,658), lipase inhibitors (e.g., Cetilistat), $PYY_{3-36}$ (as used herein "$PYY_{3-36}$" includes analogs, such as peglated $PYY_{3-36}$, e.g., those described in US Publication 2006/0178501), opioid antagonists (e.g., naltrexone), oleoyl-estrone (CAS No. 180003-17-2), obinepitide (TM30338), pramlintide (Symlin®), tesofensine (NS2330), leptin, bromocriptine, orlistat, AOD-9604 (CAS No. 221231-10-3) and sibutramine.

(ii) anti-diabetic agents, such as an acetyl-CoA carboxylase (ACC) inhibitor as described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, a monoacylglycerol O-acyltransferase inhibitor, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an a-glucoside hydrolase inhibitor (e.g., acarbose), an a-glucosidase inhibitor (e.g., adiposine, camiglibose, emiglitate, miglitol, voglibose, pradimicin-Q, and salbostatin), a PPAR γ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) modulator such as an agonist (e.g., exendin-3 and exendin-4), liraglutide, albiglutide, exenatide (Byetta®), albiglutide, taspoglutide, lixisenatide, dulaglutide, semaglutide, NN-9924, TTP-054, a protein tyrosine phosphatase-1B (PTP-1B) inhibitor (e.g., trodusquemine, hyrtiosal extract, and compounds disclosed by Zhang, S. et al., Druq Discovery Today, 12(9/10), 373-381 (2007)), a SIRT-1 inhibitor (e.g., resveratrol, GSK2245840 or GSK184072), a dipeptidyl peptidase IV (DPP-IV) inhibitor (e.g., those in WO2005116014, sitagliptin, vildagliptin, alogliptin, dutogliptin, linagliptin and saxagliptin), an insulin secretagogue, a fatty acid oxidation inhibitor, an A2 antagonist, a c-jun amino-terminal kinase (JNK) inhibitor, a glucokinase activator (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g., GSK1362885), a VPAC2 receptor agonist, an SGLT2 inhibitor, such as those described in E. C. Chao et al., Nature Reviews Drug Discovery 9, 551-559 (July 2010) including dapagliflozin, canagliflozin, BI-10733, tofogliflozin (CSG452), ASP-1941, THR1474, TS-071, ISIS388626 and LX4211 as well as those in WO2010023594, a glucagon receptor modulator such as those described in Demong, D. E. et al., Annual Reports in Medicinal Chemistry 2008, 43, 119-137, a GPR119 modulator, particularly an agonist, such as those described in WO2010140092, WO2010128425, WO2010128414, WO2010106457, Jones, R. M. et al., in Medicinal Chemistry 2009, 44, 149-170 (e.g., MBX-2982, GSK1292263, APD597 and PSN821), an FGF21 derivative or an analog such as those described in Kharitonenkov, A. et al., Current Opinion in Investigational Drugs 2009, 10(4), 359-364, TGR5 (also termed GPBAR1) receptor modulators, particularly agonists, such as those described in Zhong, M., Current Topics in Medicinal Chemistry, 2010, 10(4), 386-396 and INT777, a GPR40 agonist, such as those described in Medina, J. C., Annual Reports in Medicinal Chemistry, 2008, 43, 75-85, including but not limited to TAK-875, a GPR120 modulator, particularly an agonist, a high-affinity nicotinic acid receptor (HM74A) activator, and an SGLT1 inhibitor, such as GSK1614235. A further representative listing of anti-diabetic agents that can be combined with the compounds of the present invention can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g., PKCa, PKCb, PKCg), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g., SSTR1, SSTR2, SSTR3 and SSTR5), inhibitors or modulators of PDHK2 or PDHK4, inhibitors of MAP4K4, modulators of IL1 family including ILlbeta, and modulators of RXRalpha. In addition, suitable anti-diabetic agents include mechanisms listed by Carpino, P. A., Goodwin, B. Expert Opin. Ther. Pat, 2010, 20(12), 1627-51;

(iii) anti-hyperglycemic agents, for example, those described at page 31, line 31 through page 32, line 18 of WO 2011005611;

(iv) lipid lowering agents (for example, those described at page 30, line 20 through page 31, line 30 of WO 2011005611), and anti-hypertensive agents (for example, those described at page 31, line 31 through page 32, line 18 of WO 2011005611);

(v) acetylcholinesterase inhibitors, such as donepezil hydrochloride (ARICEPT®, MEMAC), physostigmine salicylate (ANTILIRIUM®), physostigmine sulfate (ESERINE), ganstigmine, rivastigmine (EXELON®), ladostigil, NP-0361, galantamine hydrobromide (RAZADYNE®, REMINYL®, NIVALIN®), tacrine (COGNEX®), tolserine, memoquin, huperzine A (HUP-A; Neuro-Hitech), phenserine, bisnorcymserine (also known as BNC), and INM-176;

(vi) amyloid-β (or fragments thereof), such as $Aβ_{1-15}$ conjugated to pan HLA DR-binding epitope (PADRE®), ACC-001 (Elan/Wyeth), and Affitope;

(vii) antibodies to amyloid-β (or fragments thereof), such as ponezumab, solanezumab, bapineuzumab (also known as AAB-001), AAB-002 (Wyeth/Elan), Gantenerumab, intravenous Ig (GAMMAGARD®), LY2062430 (humanized m266; Lilly), and those disclosed in International Patent Publication Nos WO04/032868, WO05/025616, WO06/036291, WO06/069081, WO06/118959, in US Patent Publication Nos US2003/0073655, US2004/0192898, US2005/0048049, US2005/0019328, in European Patent Publication Nos EP0994728 and 1257584, and in U.S. Pat. No. 5,750,349;

(viii) amyloid-lowering or -inhibiting agents (including those that reduce amyloid production, accumulation and fibrillization) such as eprodisate (KIACTA®), celecoxib, lovastatin, anapsos, colostrinin, pioglitazone, clioquinol (also known as PBT1), PBT2 (Prana Biotechnology), flurbiprofen (ANSAID®, FROBEN®) and its R-enantiomer tarenflurbil (FLURIZAN®), nitroflurbiprofen, fenoprofen (FENOPRON, NALFON®), ibuprofen (ADVIL®, MOTRIN®, NUROFEN®), ibuprofen lysinate, meclofenamic acid, meclofenamate sodium (MECLOMEN®), indomethacin (INDOCIN®), diclofenac sodium (VOLTAREN®), diclofenac potassium, sulindac (CLINORIL®), sulindac sulfide, diflunisal (DOLOBID®), naproxen (NAPROSYN®), naproxen sodium (ANAPROX®, ALEVE®), insulin-degrading enzyme (also known as insulysin), the gingko biloba extract EGb-761 (ROKAN®, TEBONIN®), tramiprosate (CEREBRIL®, ALZHEMED®), neprilysin (also known as neutral endopeptidase (NEP)), scyllo-inositol (also known as scyllitol), atorvastatin (LIPITOR®), simvastatin (ZOCOR®), ibutamoren mesylate, BACE inhibitors such as LY450139 (Lilly), BMS-782450, and GSK-188909; gamma secretase modulators and inhibitors such as ELND-007, BMS-708163 (Avagacestat), and DSP8658 (Dainippon); and RAGE (receptor for advanced glycation end-products) inhibitors, such as TTP488 (Transtech) and TTP4000 (Transtech), and those disclosed in U.S. Pat. No. 7,285,293, including PTI-777;

(ix) alpha-adrenergic receptor agonists, and beta-adrenergic receptor blocking agents (beta blockers); anticholinergics; anticonvulsants; antipsychotics; calcium channel blockers; catechol O-methyltransferase (COMT) inhibitors; central nervous system stimulants; corticosteroids; dopamine receptor agonists and antagonists; dopamine reuptake inhibitors; gamma-aminobutyric acid (GABA) receptor agonists; immunosuppressants; interferons; muscarinic receptor agonists; neuroprotective drugs; nicotinic receptor agonists; norepinephrine (noradrenaline) reuptake inhibitors; quinolines; and trophic factors;

(x) histamine 3 (H3) antagonists, such as PF-3654746 and those disclosed in US Patent Publication Nos US2005-0043354, US2005-0267095, US2005-0256135, US2008-0096955, US2007-1079175, and US2008-0176925; International Patent Publication Nos WO2006/136924, WO2007/063385, WO2007/069053, WO2007/088450, WO2007/099423, WO2007/105053, WO2007/138431, and WO2007/088462; and U.S. Pat. No. 7,115,600);

(xi) N-methyl-D-aspartate (NMDA) receptor antagonists, such as memantine (NAMENDA, AXURA, EBIXA), amantadine (SYMMETREL), acamprosate (CAMPRAL), besonprodil, ketamine (KETALAR), delucemine, dexanabinol, dexefaroxan, dextromethorphan, dextrorphan, traxoprodil, CP-283097, himantane, idantadol, ipenoxazone, L-701252 (Merck), lancicemine, levorphanol (DROMORAN), methadone, (DOLOPHINE), neramexane, perzinfotel, phencyclidine, tianeptine (STABLON), dizocilpine (also known as MK-801), ibogaine, voacangine, tiletamine, riluzole (RILUTEK), aptiganel (CERESTAT), gavestinel, and remacimide;

(xii) monoamine oxidase (MAO) inhibitors, such as selegiline (EMSAM), selegiline hydrochloride (1-deprenyl, ELDEPRYL, ZELAPAR), dimethylselegiline, brofaromine, phenelzine (NARDIL), tranylcypromine (PARNATE), moclobemide (AURORIX, MANERIX), befloxatone, safinamide, isocarboxazid (MARPLAN), nialamide (NIAMID), rasagiline (AZILECT), iproniazide (MARSILID, IPROZID, IPRONID), iproclozide, toloxatone (HUMORYL, PERENUM), bifemelane, desoxypeganine, harmine (also known as telepathine or banasterine), harmaline, linezolid (ZYVOX, ZYVOXID), and pargyline (EUDATIN, SUPIRDYL);

(xiii) phosphodiesterase (PDE) inhibitors, including (a) PDE1 inhibitors (b) PDE2 inhibitors (c) PDE3 inhibitors (d) PDE4 inhibitors (e) PDE5 inhibitors (f) PDE9 inhibitors (e.g., PF-04447943, BAY 73-6691 (Bayer AG) and those disclosed in US Patent Publication Nos US2003/0195205, US2004/0220186, US2006/0111372, US2006/0106035, and U.S. Ser. No. 12/118,062 (filed May 9, 2008)), and (g) PDE10 inhibitors such as 2-({4-[1-methyl-4-(pyridin-4-yl)-1H-pyrazol-3-yl]phenoxy}methyl) quinoline (PF-2545920);

(xiv) serotonin (5-hydroxytryptamine) 1A ($5\text{-HT}_{1A}$) receptor antagonists, such as spiperone, levo-pindolol, lecozotan;

(xv) serotonin (5-hydroxytryptamine) 2C ($5\text{-HT}_{2C}$) receptor agonists, such as vabicaserin, and zicronapine; serotonin (5-hydroxytryptamine) 4 ($5\text{-HT}_4$) receptor agonists/antagonists, such as PRX-03140 (Epix) and PF-04995274;

(xvi) serotonin (5-hydroxytryptamine) 3C ($5\text{-HT}_{3c}$) receptor antagonists, such as Ondansetron (Zofran);

(xvii) serotonin (5-hydroxytryptamine) 6 ($5\text{-HT}_6$) receptor antagonists, such as mianserin (TOLVON, BOLVIDON, NORVAL), methiothepin (also known as metitepine), ritanserin, SB-271046, SB-742457 (GlaxoSmithKline), Lu AE58054 (Lundbeck A/S), SAM-760, and PRX-07034 (Epix);

(xviii) serotonin (5-HT) reuptake inhibitors such as alaproclate, citalopram (CELEXA, CIPRAMIL), escitalopram (LEXAPRO, CIPRALEX), clomipramine (ANAFRANIL), duloxetine (CYMBALTA), femoxetine (MALEXIL), fenfluramine (PONDIMIN), norfenfluramine, fluoxetine (PROZAC), fluvoxamine (LUVOX), indalpine, milnacipran (IXEL), paroxetine (PAXIL, SEROXAT), sertraline (ZOLOFT, LUSTRAL), trazodone (DESYREL, MOLIPAXIN), venlafaxine (EFFEXOR), zimelidine (NORMUD, ZELMID), bicifadine, desvenlafaxine (PRISTIQ), brasofensine, vilazodone, cariprazine and tesofensine;

(xix) Glycine transporter-1 inhibitors such as paliflutine, ORG-25935, and ORG-26041; and mGluR modulators such as AFQ-059 and amantidine;

(xx) AMPA-type glutamate receptor modulators such as perampanel, mibampator, selurampanel, GSK-729327, and N-{(3S,4S)-4-[4-(5-cyanothiophen-2-yl)phenoxy]tetrahydrofuran-3-yl}propane-2-sulfonamide;

(xxi) P450 inhibitors, such as ritonavir;

(xxii) tau therapy targets, such as davunetide;

and the like.

The present invention further comprises kits that are suitable for use in performing the methods of treatment described above. In one embodiment, the kit contains a first dosage form comprising one or more of the compounds of the present invention and a container for the dosage, in quantities sufficient to carry out the methods of the present invention.

In another embodiment, the kit of the present invention comprises one or more compounds of the invention.

General Synthetic Schemes

The compounds of Formula I may be prepared by the methods described below, together with synthetic methods known in the art of organic chemistry, or modifications and transformations that are familiar to those of ordinary skill in the art. The starting materials used herein are commercially available or may be prepared by routine methods known in the art [such as those methods disclosed in standard reference books such as the *Compendium of Organic Synthetic Methods*, Vol. I-XII (published by Wiley-Interscience)]. Preferred methods include, but are not limited to, those described below.

During any of the following synthetic sequences it may be necessary and/or desirable to protect sensitive or reactive groups on any of the molecules concerned.

This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991; and T. W. Greene and P. G. M. Wuts, Protective Groups in Organic Chemistry, John Wiley & Sons, 1999, which are hereby incorporated by reference.

Compounds of Formula I, or their pharmaceutically acceptable salts, can be prepared according to the reaction Schemes discussed herein below. Unless otherwise indicated, the substituents in the Schemes are defined as above. Isolation and purification of the products is accomplished by standard procedures, which are known to a chemist of ordinary skill.

One skilled in the art will recognize that in many cases, the compounds in Schemes 1 through 6 will be generated as a mixture of diastereomers and/or enantiomers; these may be separated at various stages of the synthetic schemes using conventional techniques or a combination of such techniques, such as, but not limited to, crystallization, normal-phase chromatography, reversed phase chromatography and chiral chromatography, to afford the single enantiomers of the invention.

It will be understood by one skilled in the art that the various symbols, superscripts and subscripts used in the schemes, methods and examples are used for convenience of representation and/or to reflect the order in which they are introduced in the schemes, and are not intended to necessarily correspond to the symbols, superscripts or subscripts in the appended claims. The schemes are representative of methods useful in synthesizing the compounds of the present invention. They are not to constrain the scope of the invention in any way.

Scheme 1 refers to the preparation of compounds of Formula I. Referring to Scheme 1, the compound of Formula I can be prepared from the compound of Formula II through a removal of protecting group $P^1$. $P^1$ in this case refers to groups well known to those skilled in the art for amine protection. For example, $P^1$ may be a benzoyl group (Bz), which can be cleaved via acidic conditions, or through treatment with 1,8-diazabicyclo[5.4.0]undec-7-ene (DBU) in methanol. Alternatively $P^1$ may be one of many protecting group suitable for amines, including 9-fluorenylmethoxycarbonyl (Fmoc) or tert-butoxycarbonyl (BOC) and can be cleaved under standard conditions known to one skilled in the art.

Scheme 1

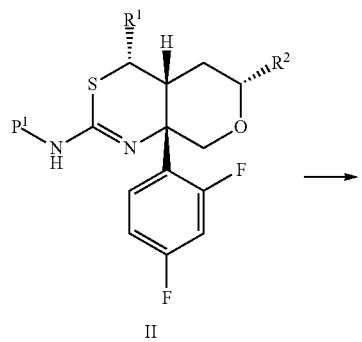

II

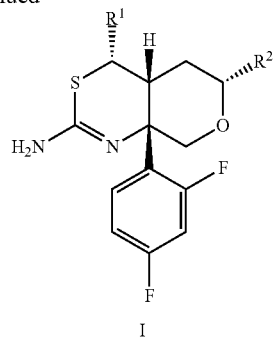

I

Scheme 2 refers to the preparation of compounds II wherein $P^1$ is Bz or Fmoc. The treatment of lactones of Formula III with base, for instance potassium bis(trimethylsilyl)amide (KHMDS), and N-(5-chloropyridin-2-yl)-1,1,1-trifluoro-N-[(trifluoromethyl)sulfonyl]-methanesulfonamide (Comins' Reagent) provides compounds of Formula IV. The reaction of enol triflate IV with the corresponding $R^2$-containing boronic acid using standard Suzuki reaction conditions (A. Suzuki, *Journal of Organometallic Chemistry* 1999, 576, 147-168; N. Miyaura and A. Suzuki, *Chemical Reviews* 1995, 95, 2457-2483; A. F. Littke et al., *J. Am. Chem. Soc.* 2000, 122, 4020-4028) replaces the triflate with $R^2$; subsequent reduction of the resultant enol ether using standard reduction conditions, for instance trimethylsilyl trifluoromethanesulfonate (TMSOTf) and triethylsilane, provides compounds of Formula II. Alternatively, the corresponding $R^2$-containing heteroaryl iodide can be coupled with the compound of Formula IV under palladium-mediated conditions with hexabutyldistannane. Compound II can be converted into a compound of Formula I according to the methods of Scheme 1.

Scheme 2

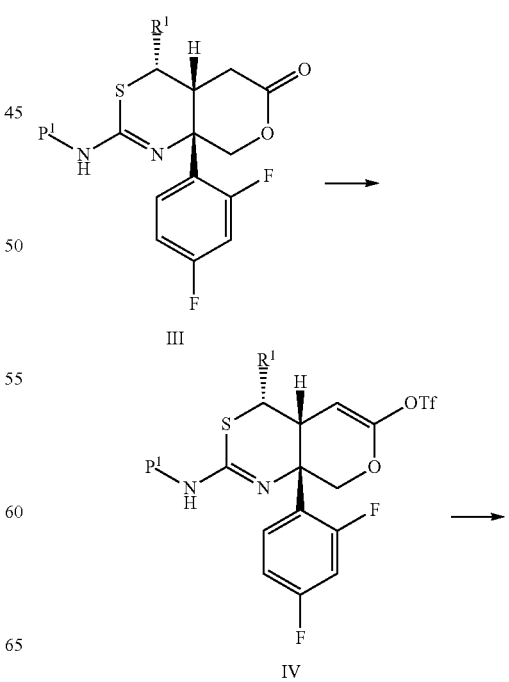

III

IV

-continued

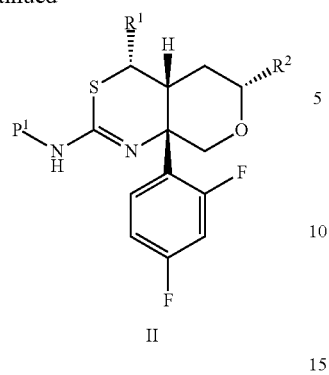

II

Scheme 3 refers to the preparation of compounds II wherein P¹ is Bz or Boc. The addition of an organometallic derivative (magnesiate or lithiate) of R² to compounds of Formula III under standard anionic conditions, for instance in tetrahydrofuran (THF) at −78° C., provides compounds of Formula V. Subsequent reduction of the resultant lactol using standard reduction conditions, for instance trimethylsilyl trifluoromethanesulfonate (TMSOTf) and triethylsilane, provides compounds of Formula II. Compound II can be converted into a compound of Formula I according to the methods of Scheme 1.

Scheme 3

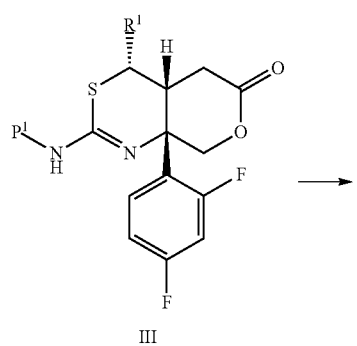

III

-continued

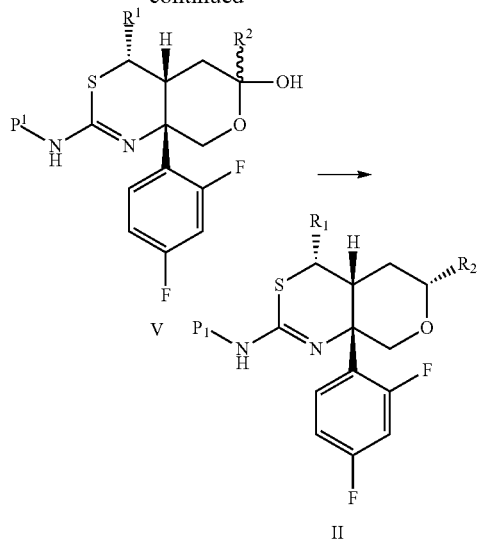

Scheme 4 refers to the preparation of compounds of Formula III wherein P¹ is Bz or Fmoc. Isoxazolidines of Formula VI (which may be obtained via the chemistry depicted in Scheme 6, utilizing a benzyloxymethyl group in place of R²) are subjected to reducing conditions, for instance zinc in acetic acid, affording compounds of Formula VII. The amino alcohols VII are treated with an isothiocyanate, for instance benzoyl isothiocyanate, to provide thioureas of Formula VIII. Cyclization is induced using strong acid, including for instance sulfuric acid, or alternatively, standard Mitsunobu conditions, to give compounds of Formula IX. Cleavage of the benzyl ether under standard conditions, for instance using boron trichloride, provides alcohols of Formula X. The oxidation of compounds of Formula X can be affected by a number of standard oxidation protocols, for instance using Dess-Martin periodinane or sulfur trioxide-pyridine with dimethyl sulfoxide (Parikh-Doering conditions). Aldehydes of Formula XI are subjected to basic conditions, for instance potassium carbonate in acetonitrile, and trapped using an appropriate anhydride, for instance acetic anhydride, to afford protected enol ethers of Formula XII, wherein P² is an acyl group. Oxidative cleavage of the resulting enol moiety using standard conditions, including for instance ruthenium chloride and sodium periodate, affords lactones of Formula III. Compound III can be converted into a compound of Formula I according to the methods of Schemes 2 or 3, and 1.

Scheme 4

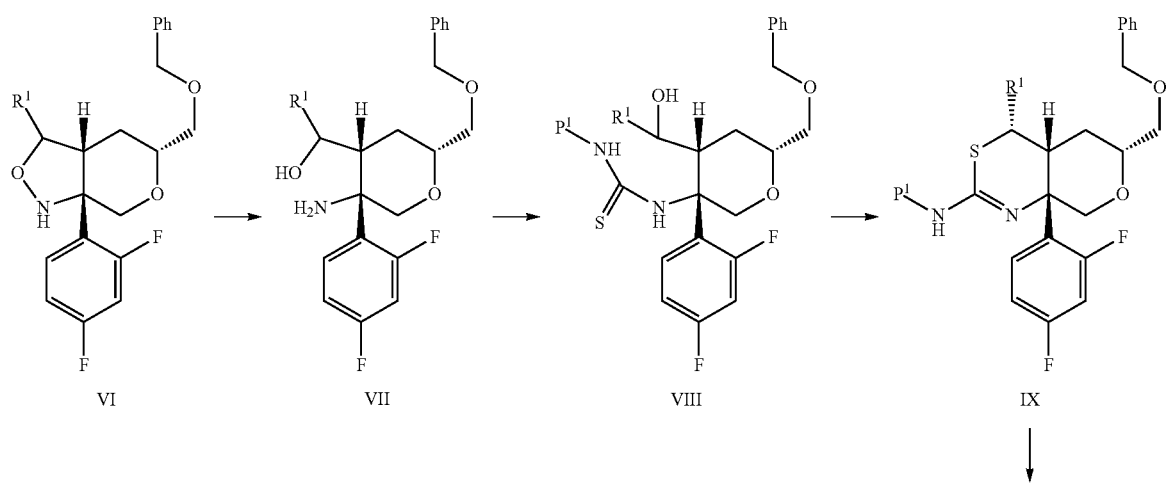

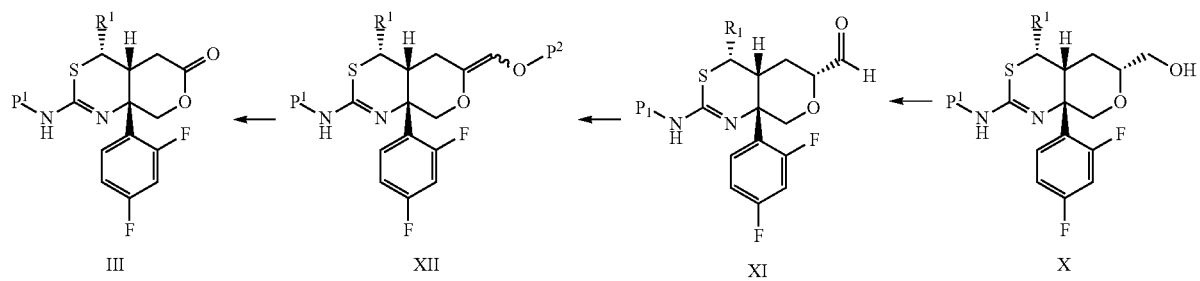

Scheme 5 refers to the preparation of compounds II wherein P¹ is Bz or Fmoc. Isoxazolidines of Formula XIII are subjected to reducing conditions, for instance zinc in acetic acid, affording compounds of Formula XIV. The resulting amino alcohols are treated with an isothiocyanate, for instance benzoyl isothiocyanate, to provide thioureas of Formula XV. Cyclization is induced using strong acid, including for instance sulfuric acid, or alternatively, standard Mitsunobu conditions, to give compounds of Formula II. Compound II can be directly converted into a compound of Formula I according to the methods of Scheme 1.

Scheme 5

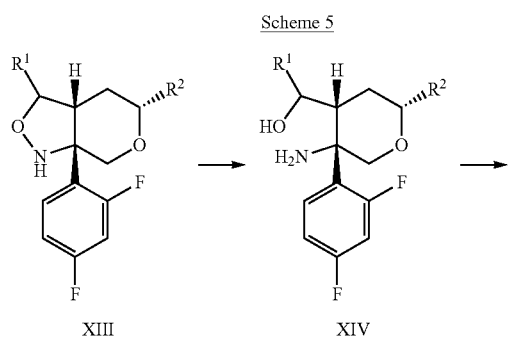

-continued

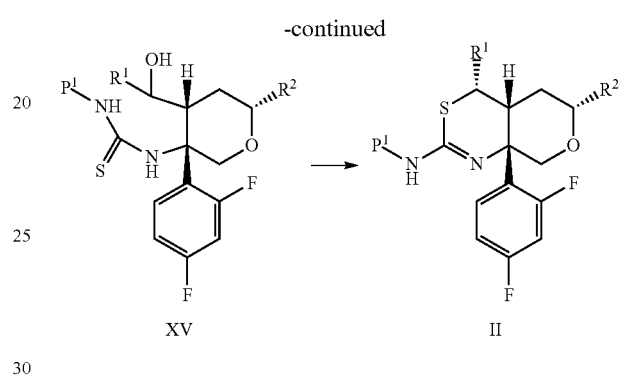

Scheme 6 refers to the preparation of compounds XIII. Homoallylic alcohol XVI is alkylated with 2-bromo-1,1-dimethoxyethane under basic conditions, such as treatment with potassium hydride, to provide the corresponding ether XVII. The acetal is cleaved under acidic conditions, aqueous HCl as an example, to give aldehyde XVIII. Condensation with a hydroxylamine salt, such as hydroxylamine sulfate, provides a geometric mixture of the corresponding oxime XIX. Cycloaddition to form isoxazoline XX may be carried out by treatment of oxime XIX with an oxidizing agent, such as sodium hypochlorite or N-chlorosuccinimide. Reaction of isoxazoline XX with an appropriate arylmetallic reagent (for instance, an aryllithium such as 2,4-difluorophenyllithium, or the corresponding aryl Grignard reagent) at low temperature, e.g., −78° C., yields compounds of Formula XIII. One of ordinary skill in the art will recognize that the stereochemistry of addition of the arylmetallic reagent is determined by the stereochemistry of the adjacent methine center, yielding a racemic mixture of cis-fused diastereomers, which can be converted into compounds of Formula I according to the methods of Schemes 5 and 1.

Scheme 6

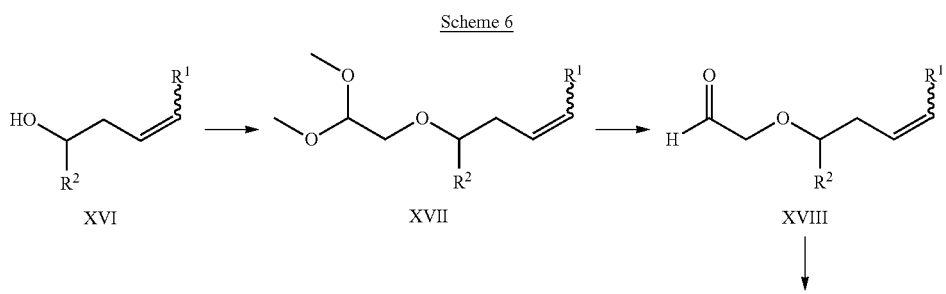

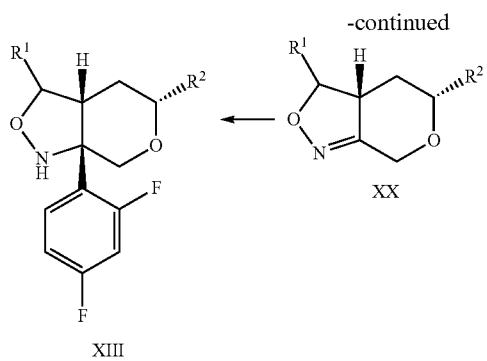
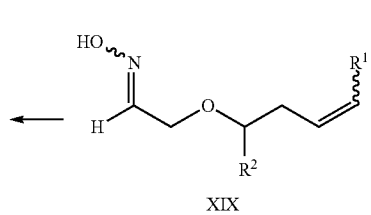

Experimental Procedures and Working Examples

The following illustrate the synthesis of various compounds of the present invention. Additional compounds within the scope of this invention may be prepared using the methods illustrated in these Examples, either alone or in combination with techniques generally known in the art.

Experiments were generally carried out under inert atmosphere (nitrogen or argon), particularly in cases where oxygen- or moisture-sensitive reagents or intermediates were employed. Commercial solvents and reagents were generally used without further purification, including anhydrous solvents where appropriate (generally AcroSeal® products from Acros Organics or DriSolv® products from EMD Chemicals.). Products were generally dried under vacuum before being carried on to further reactions or submitted for biological testing. Mass spectrometry data is reported from either liquid chromatography-mass spectrometry (LCMS), atmospheric pressure chemical ionization (APCI) or gas chromatography-mass spectrometry (GCMS) instrumentation. Chemical shifts for nuclear magnetic resonance (NMR) data are expressed in parts per million (ppm, δ) referenced to residual peaks from the deuterated solvents employed.

For syntheses referencing procedures in other Examples or Methods, reaction conditions (length of reaction and temperature) may vary. In general, reactions were followed by thin layer chromatography or mass spectrometry, and subjected to work-up when appropriate. Purifications may vary between experiments: in general, solvents and the solvent ratios used for eluents/gradients were chosen to provide appropriate $R_f$s or retention times.

Preparation P1

N-[(4aR,6R,8aS)-8a-(2,4-Difluorophenyl)-6-(hydroxymethyl)-4,4a,5,6,8,8a-hexahydropyrano[3,4-d][1,3]thiazin-2-yl]benzamide (P1)

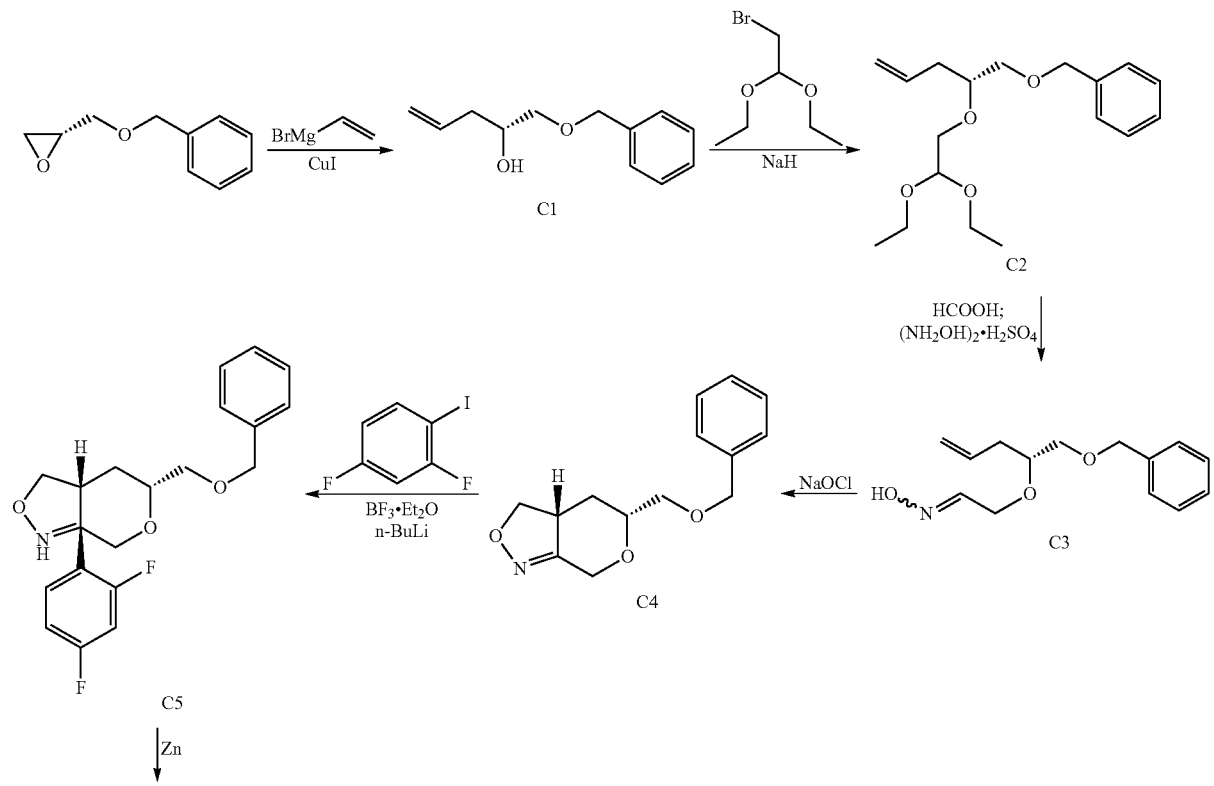

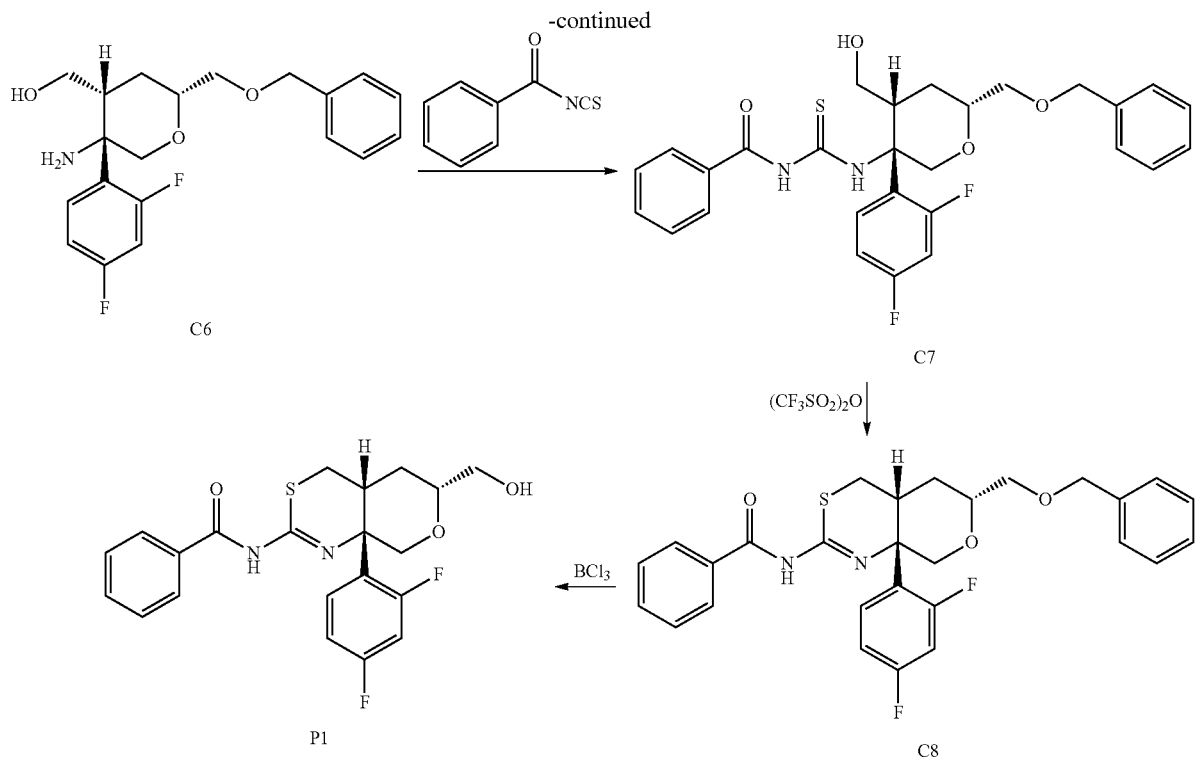

Step 1. Synthesis of (2R)-1-(benzyloxy)pent-4-en-2-ol (C1)

To a solution of (2R)-2-[(benzyloxy)methyl]oxirane (167 g, 1.02 mol) in tetrahydrofuran (2 L) was added copper(I) iodide (11.62 g, 61.02 mmol) at room temperature. The mixture was stirred for 5 minutes, then cooled to −78° C. A solution of vinylmagnesium bromide (1 M in tetrahydrofuran, 1.12 L, 1.12 mol) was added drop-wise over 1 hour while the reaction temperature was maintained below −70° C. Upon completion of the addition, the cooling bath was removed and the reaction mixture was left to stir at room temperature for 1 hour, then quenched by slow addition of aqueous ammonium chloride solution (200 mL). After dilution with aqueous ammonium chloride solution (1.5 L) and ethyl acetate (1.5 L), the aqueous layer was extracted with ethyl acetate (1 L) and the combined organic layers were washed with aqueous ammonium chloride solution (1.5 L), dried over magnesium sulfate, filtered, and concentrated in vacuo. Three batches of this reaction were carried out and combined to give the product as an orange oil. Yield: 600 g, 3.1 mol, quantitative. $^1$H NMR (400 MHz, CDCl$_3$) δ 7.28-7.40 (m, 5H), 5.78-5.90 (m, 1H), 5.08-5.17 (m, 2H), 4.57 (s, 2H), 3.86-3.94 (m, 1H), 3.53 (dd, J=9.6, 3.3 Hz, 1H), 3.39 (dd, J=9.6, 7.4 Hz, 1H), 2.26-2.34 (m, 3H).

Step 2. Synthesis of ({[(2R)-2-(2,2-diethoxyethoxy)pent-4-en-1-yl]oxy}methyl)benzene (C2)

This reaction was carried out in two identical experiments. To a 0° C. suspension of sodium hydride (60% in mineral oil, 124.8 g, 3.12 mol) in tetrahydrofuran (1 L) was added a solution of (2R)-1-(benzyloxy)pent-4-en-2-ol (C1) (200 g, 1.04 mol) in tetrahydrofuran (500 mL). The reaction was stirred for 30 minutes at room temperature, whereupon 2-bromo-1,1-diethoxyethane (528 g, 2.68 mol) was added, and the reaction mixture was heated at reflux for 18 hours. The mixture was carefully quenched with water (2×300 mL) and the combined experiments were concentrated in vacuo. The aqueous residue was partitioned between ethyl acetate (5 L) and water (5 L). The organic layer was washed with saturated aqueous sodium chloride solution (5 L), dried, and concentrated. Purification via silica gel chromatography (Eluent: 20:1 petroleum ether/ethyl acetate) provided the product as a yellow oil. Yield: 300 g, 0.97 mol, 47%. $^1$H NMR (400 MHz, CDCl$_3$) δ 7.26-7.37 (m, 5H), 5.78-5.90 (m, 1H), 5.01-5.13 (m, 2H), 4.61 (t, J=5.3 Hz, 1H), 4.55 (s, 2H), 3.48-3.74 (m, 9H), 2.30-2.36 (m, 2H), 1.22 (t, J=7.1 Hz, 3H), 1.21 (t, J=7.0 Hz, 3H).

Step 3. Synthesis of 2-{[(2R)-1-(benzyloxy)pent-4-en-2-yl]oxy}-N-hydroxyethanimine (C3)

A solution of ({[(2R)-2-(2,2-diethoxyethoxy)pent-4-en-1-yl]oxy}methyl)benzene (C2) (234 g, 0.759 mol) in formic acid (400 mL) and water (100 mL) was stirred at room temperature for 2 hours. As LCMS analysis revealed a small amount of remaining starting material, formic acid (50 mL) was added and the reaction mixture was stirred for a further 30 minutes. The reaction mixture was diluted with ethanol (1 L) and water (400 mL). Hydroxylamine sulfate (435 g, 2.65 mol) and sodium acetate (217 g, 2.64 mol) were added and the reaction was stirred at room temperature for 18 hours. The reaction mixture was then filtered and concentrated in vacuo. The residue was partitioned between ethyl acetate (500 mL) and water (1 L), and the aqueous layer was extracted with ethyl acetate (3×500 mL). The combined organic layers were washed with saturated aqueous sodium chloride solution (2×500 mL), dried over magnesium sulfate, filtered, and concentrated under reduced pressure to provide the product as an orange oil. By $^1$H NMR, this material consisted of a roughly 1:1 mixture of oxime isomers. Yield: 234 g, which was taken directly to the following step. LCMS m/z 250.1 [M+H$^+$]. $^1$H NMR (400 MHz, CDCl$_3$), characteristic peaks: δ [7.52 (t, J=5.5 Hz) and 6.96 (t, J=3.6 Hz), total 1H], 7.28-7.39 (m, 5H), 5.74-5.87 (m, 1H), 5.04-5.14 (m, 2H), 4.55 and 4.56 (2 s, total 2H), {4.45-4.55 (m) and [4.27 (dd, half of ABX pattern, J=13.2, 5.4 Hz) and 4.21 (dd, half of ABX pattern, J=13.2, 5.6 Hz)], total 2H}, 2.30-2.37 (m, 2H).

Step 4. Synthesis of (3aR,5R)-5-[(benzyloxy)methyl]-3,3a,4,5-tetrahydro-7H-pyrano[3,4-c][1,2]oxazole (C4)

An aqueous solution of sodium hypochlorite (14.5% solution, 600 mL) was added drop-wise to a 0° C. solution of 2-{[(2R)-1-(benzyloxy)pent-4-en-2-yl]oxy}-N-hydroxyethanimine (C3) (224 g from the previous step, ≤0.759 mol) in dichloromethane (1 L), while the internal temperature was maintained below 15° C. After completion of the addition, the reaction mixture was left to stir at 0° C. for 1.5 hours, then diluted with water (1 L) and dichloromethane (500 mL). The aqueous layer was extracted with dichloromethane (2×500 mL), and the combined organic layers were washed with saturated aqueous sodium chloride solution (500 mL), water (500 mL) and again with saturated aqueous sodium chloride solution (500 mL). They were subsequently dried over magnesium sulfate, filtered, and concentrated in vacuo. Purification via silica gel chromatography (Gradient: 0% to 25% ethyl acetate in heptane) afforded the product as a colorless oil. The indicated relative stereochemistry of compound C4 was assigned based on nuclear Overhauser enhancement studies, which revealed an interaction between the methine protons on carbons 3a and 5. Yield: 85.3 g, 345 mmol, 45% over 2 steps. LCMS m/z 248.1 [M+H$^+$]. $^1$H NMR (400 MHz, CDCl$_3$) δ 7.27-7.40 (m, 5H), 4.77 (d, J=13.5 Hz, 1H), 4.54-4.65 (m, 3H), 4.22 (dd, J=13.5, 1 Hz, 1H), 3.79 (dd, J=11.7, 8.0 Hz, 1H), 3.69-3.76 (m, 1H), 3.57 (dd, half of ABX pattern, J=10.1, 5.9 Hz, 1H), 3.49 (dd, half of ABX pattern, J=10.1, 4.3 Hz, 1H), 3.39-3.5 (m, 1H), 2.20 (ddd, J=12.9, 6.5, 1.6 Hz, 1H), 1.51-1.62 (m, 1H).

Step 5. Synthesis of (3aR,5R,7aS)-5-[(benzyloxy)methyl]-7a-(2,4-difluorophenyl)hexahydro-1H-pyrano[3,4-c][1,2]oxazole (C5)

Boron trifluoride diethyl etherate (60.1 mL, 474 mmol) was added to a solution of (3aR,5R)-5-[(benzyloxy)methyl]-3,3a,4,5-tetrahydro-7H-pyrano[3,4-c][1,2]oxazole (C4) (50.0 g, 202 mmol) in a 1:1 mixture of toluene and diisopropyl ether (2 L) at an internal temperature of −76° C. The reaction was stirred at this temperature for 30 minutes, then treated with 2,4-difluoro-1-iodobenzene (27.1 mL, 226 mmol). While the reaction temperature was maintained at −76 to −71° C., n-butyllithium (2.5 M in hexanes, 85.7 mL, 214 mmol) was slowly added. The reaction mixture was stirred at −76° C. for 1.5 hours, then was quenched with saturated aqueous ammonium chloride solution (1 L) and partitioned between water (1 L) and ethyl acetate (750 mL). After the heterogeneous mixture warmed to room temperature, the aqueous layer was extracted with ethyl acetate (3×250 mL), and the combined organic layers were washed with saturated aqueous sodium chloride solution (550 mL), dried over sodium sulfate, filtered, and concentrated in vacuo. Chromatography on silica gel (Gradient: 0% to 70% ethyl acetate in heptane) afforded the product as a yellow oil. Yield: 48.14 g, 133.2 mmol, 66%. $^1$H NMR (400 MHz, CDCl$_3$) δ 7.94 (ddd, J=9, 9, 7 Hz, 1H), 7.28-7.40 (m, 5H), 6.87-6.93 (m, 1H), 6.80 (ddd, J=12.0, 8.6, 2.4 Hz, 1H), 4.60 (AB quartet, J$_{AB}$=12.1 Hz, Δv$_{AB}$=21.4 Hz, 2H), 4.14 (br dd, J=12.8, 1.3 Hz, 1H), 3.82-3.90 (m, 2H), 3.72 (d, J=7.2 Hz, 1H), 3.54-3.60 (m, 2H), 3.50 (dd, half of ABX pattern, J=10.3, 4.1 Hz, 1H), 3.04-3.13 (m, 1H), 1.86 (ddd, J=14.0, 7.0, 2.0 Hz, 1H), 1.49-1.61 (m, 1H).

Step 6. Synthesis of [(2R,4R,5S)-5-amino-2-[(benzyloxy)methyl]-5-(2,4-difluorophenyl)tetrahydro-2H-pyran-4-yl]methanol (C6)

(3aR,5R,7aS)-5-[(Benzyloxy)methyl]-7a-(2,4-difluorophenyl) hexahydro-1H-pyrano[3,4-c][1,2]oxazole (C5) (48.1 g, 133 mmol) was dissolved in acetic acid (444 mL) and treated with zinc powder (113 g, 1.73 mol). The reaction mixture, which had warmed to 40° C., was allowed to cool to room temperature and stir for 16 hours. Insoluble material was removed via filtration through a diatomaceous earth pad, and the pad was washed with ethyl acetate (3×500 mL). The combined filtrates were neutralized with saturated aqueous sodium bicarbonate solution (2.5 L), and the aqueous layer was extracted with ethyl acetate (3×500 mL). The combined organic layers were washed with saturated aqueous sodium chloride solution (1 L), dried over sodium sulfate, filtered, and concentrated under reduced pressure to provide the product as a thick yellow oil, which was used in the following reaction without additional purification. Yield: 48.7 g, assumed quantitative. $^1$H NMR (400 MHz, CDCl$_3$), characteristic peaks: δ 7.62-7.80 (br m, 1H), 7.28-7.39 (m, 5H), 6.94-7.06 (m, 1H), 6.83 (ddd, J=12.7, 8.5, 2.6 Hz, 1H), 4.61 (AB quartet, upfield doublet is broadened, J$_{AB}$=12.2 Hz, Δv$_{AB}$=30.5 Hz, 2H), 4.22 (dd, J=11.6, 2.2 Hz, 1H), 3.83-3.92 (br m, 1H), 3.62-3.73 (br m, 1H), 3.56 (dd, J=10.2, 3.5 Hz, 1H), 3.34-3.41 (m, 1H), 2.26-2.43 (br m, 1H), 2.00-2.17 (br m, 1H), 1.65 (ddd, J=14.1, 4.5, 2.5 Hz, 1H).

Step 7. Synthesis of N-{[(3S,4R,6R)-6-[(benzyloxy)methyl]-3-(2,4-difluorophenyl)-4-(hydroxymethyl)tetrahydro-2H-pyran-3-yl]carbamothioyl}benzamide (C7)

Benzoyl isothiocyanate (17.8 mL, 132 mmol) was added to a solution of [(2R,4R,5S)-5-amino-2-[(benzyloxy)methyl]-5-(2,4-difluorophenyl)tetrahydro-2H-pyran-4-yl]methanol (C6) (48.7 g, 134 mmol) in dichloromethane (1.34 L), and the reaction mixture was allowed to stir at room temperature for 18 hours. Removal of solvent in vacuo afforded the product as a white solid, which was used without additional purification. Yield: 72.2 g, assumed quantitative. LCMS m/z 527.2 [M+H$^+$]. $^1$H NMR (400 MHz, CD$_3$OD), characteristic peaks: δ 7.89-7.93 (m, 2H), 7.62-7.67 (m, 1H), 7.50-7.56 (m, 2H), 7.42-7.54 (br m, 1H), 7.31-7.36 (m, 2H), 7.17-7.28 (m, 3H), 6.86-6.98 (m, 2H), 4.57 (AB quartet, J$_{AB}$=11.9 Hz, Δv$_{AB}$=11.8 Hz, 2H), 3.84-3.91 (m, 1H), 3.64 (br dd, half of ABX pattern, J=10.6, 6.0 Hz, 1H), 3.58 (dd, half of ABX pattern, J=10.6, 3.8 Hz, 1H), 3.44-3.54 (br m, 1H), 2.32-2.59 (br m, 1H), 1.82-2.06 (m, 2H).

Step 8. Synthesis of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8)

Pyridine (11.0 mL, 137 mmol) was added to a solution of N-{[(3S,4R,6R)-6-[(benzyloxy)methyl]-3-(2,4-difluorophenyl)-4-(hydroxymethyl)tetrahydro-2H-pyran-3-yl]carbamothioyl}benzamide (C7) (19.00 g, 36.08 mmol) in dichloromethane (150 mL), and the resulting solution was cooled to −50 to −60° C. Trifluoromethanesulfonic anhydride (12.1 mL, 71.9 mmol) in dichloromethane (50 mL) was added drop-wise, and the reaction mixture was gradually warmed to −5° C. over 3 hours. Water was added, and the aqueous layer was extracted with dichloromethane. The combined organic layers were washed with saturated aqueous sodium chloride solution, dried over magnesium sulfate, filtered, and concentrated in vacuo. Purification via silica gel chromatography (Gradient: 20% to 40% ethyl acetate in heptane) provided the product as a yellow foam. Yield: 15.51 g, 30.50 mmol, 85%. LCMS m/z 509.2 [M+H$^+$]. $^1$H NMR (400 MHz, CDCl$_3$) δ 8.23 (br d, J=7 Hz, 2H), 7.37-7.57 (br m, 4H), 7.24-7.36 (m, 5H), 6.85-6.97 (m, 2H), 4.58 (AB quartet, upfield signals are slightly broadened, J$_{AB}$=11.9 Hz, Δv$_{AB}$=23.5 Hz, 2H), 4.17 (br d, J=12 Hz, 1H), 3.90-3.97 (m, 1H), 3.83 (br d, J=12 Hz, 1H), 3.64 (dd, half of ABX pattern, J=10.1, 6.4 Hz, 1H), 3.50 (dd, half of ABX pattern, J=10.2, 4.4 Hz, 1H), 3.11-3.21 (br m, 1H), 3.02 (dd, J=12.9, 4.1 Hz, 1H), 2.64 (br d, J=13 Hz, 1H), 1.92-2.05 (br m, 1H), 1.71 (br d, J=13 Hz, 1H).

Step 9. Synthesis of N-[(4aR,6R,8aS)-8a-(2,4-difluorophenyl)-6-(hydroxymethyl)-4,4a,5,6,8,8a-hexahydropyrano[3,4-d][1,3]thiazin-2-yl]benzamide (P1)

Boron trichloride (1 M solution in heptane, 89.7 mL, 89.7 mmol) was added to a 0° C. solution of N-[(4aR,6R,8aS)-6-[(benzyloxy)methyl]-8a-(2,4-difluorophenyl)-4,4a,5,6,8,8a-hexahydropyrano[3,4-d][1,3]thiazin-2-yl]benzamide (C8) (15.20 g, 29.89 mmol) in dichloromethane (150 mL). After 15 minutes, the reaction mixture was allowed to warm to room temperature and stirred for 4 hours. Methanol (50 mL) was then added, first drop-wise {Caution: violent reaction} and then at a steady rate, while the interior of the flask was flushed with nitrogen gas. The mixture was heated at reflux for 30 minutes, cooled to room temperature and concentrated in vacuo. The residue was again dissolved in methanol, stirred, and concentrated in vacuo. The resulting material was taken up in dichloromethane and washed sequentially with 1 M aqueous sodium hydroxide solution, water, and saturated aqueous sodium chloride solution. The organic layer was dried over magnesium sulfate, filtered, and concentrated under reduced pressure. Chromatographic purification on silica gel (Gradient: 0% to 3% methanol in ethyl acetate) provided the product as a yellow foam. Yield: 11.97 g, 28.60 mmol, 96%. LCMS m/z 419.2 [M+H$^+$]. $^1$H NMR (400 MHz, CD$_3$OD) δ 8.13 (d, J=7.4 Hz, 2H), 7.50-7.56 (m, 1H), 7.41-7.49 (m, 3H), 7.02-7.11 (m, 2H), 4.13 (dd, J=11.9, 1.8 Hz, 1H), 3.90 (d, J=12.1 Hz, 1H), 3.72-3.80 (m, 1H), 3.59 (d, J=5.1 Hz, 2H), 3.14-3.24 (br m, 1H), 2.96 (dd, half of ABX pattern, J=13.1, 4.1 Hz, 1H), 2.75 (dd, half of ABX pattern, J=13.1, 2.7 Hz, 1H), 1.80-1.92 (m, 1H), 1.70 (ddd, J=13.4, 4.2, 2.4 Hz, 1H).

Preparation P2

(4aR,6R,8aS)-2-(Benzoylamino)-8a-(2,4-difluorophenyl)-4,4a,5,6,8,8a-hexahydropyrano[3,4-d][1,3]thiazine-6-carboxylic acid (P2)

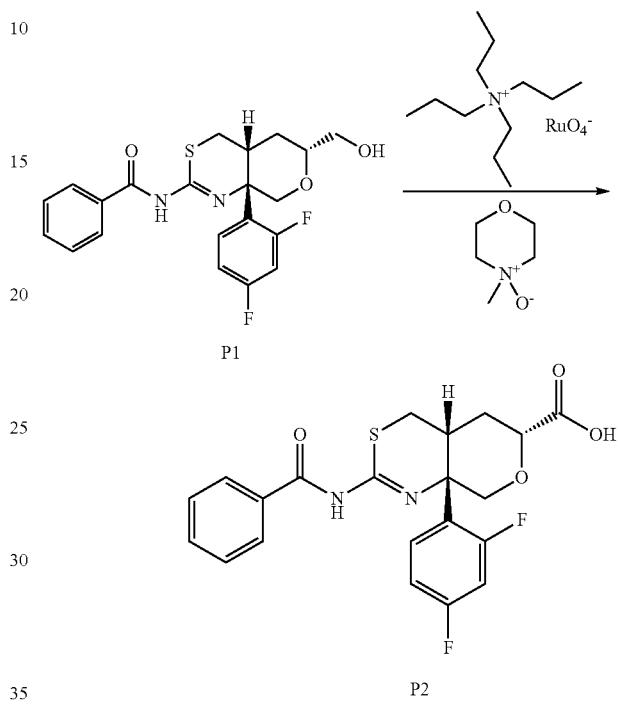

Tetrapropylammonium perruthenate (1.09 g, 3.10 mmol) was added to a mixture of N-[(4aR,6R,8aS)-8a-(2,4-difluorophenyl)-6-(hydroxymethyl)-4,4a,5,6,8,8a-hexahydropyrano[3,4-d][1,3]thiazin-2-yl]benzamide (P1) (13.0 g, 31.1 mmol) and 4-methylmorpholine N-oxide monohydrate (25.2 g, 186 mmol) in acetonitrile (207 mL), and the reaction mixture was stirred for 90 minutes at room temperature. After addition of 2-propanol (100 mL), it was stirred for an additional 2 hours and then concentrated in vacuo. The residue was partitioned between ethyl acetate and 0.5 M aqueous sodium hydroxide solution. The organic layer was extracted twice with 0.5 M aqueous sodium hydroxide solution, and the combined aqueous layers were acidified to a pH of approximately 1 with 2 M aqueous hydrochloric acid, then extracted three times with ethyl acetate. The combined ethyl acetate layers were dried over sodium sulfate, filtered, and concentrated under reduced pressure; the residue was dissolved in dichloromethane, washed with water and with saturated aqueous sodium chloride solution, dried over sodium sulfate, filtered, and concentrated in vacuo. Purification via chromatography on silica gel (Gradient: 0% to 20% methanol in dichloromethane) provided the product as a reddish solid. Yield: 12.36 g, 28.58 mmol, 92%. LCMS m/z 433.2 [M+H$^+$]. $^1$H NMR (400 MHz, CD$_3$OD) δ 8.09-8.13 (m, 2H), 7.52-7.57 (m, 1H), 7.43-7.51 (m, 3H), 7.03-7.11 (m, 2H), 4.35 (dd, J=11.2, 3.4 Hz, 1H), 4.19 (dd, J=12.0, 1.4 Hz, 1H), 3.97 (d, J=12.1 Hz, 1H), 3.20-3.27 (m, 1H), 2.96 (dd, half of ABX pattern, J=13.1, 4.0 Hz, 1H), 2.78 (dd, half of ABX pattern, J=13.2, 2.8 Hz, 1H), 2.03-2.15 (m, 2H).

Preparation P3

N-[(4aR,6R,8aS)-8a-(2,4-Difluorophenyl)-6-formyl-4,4a,5,6,8,8a-hexahydropyrano[3,4-d][1,3]thiazin-2-yl]benzamide (P3)

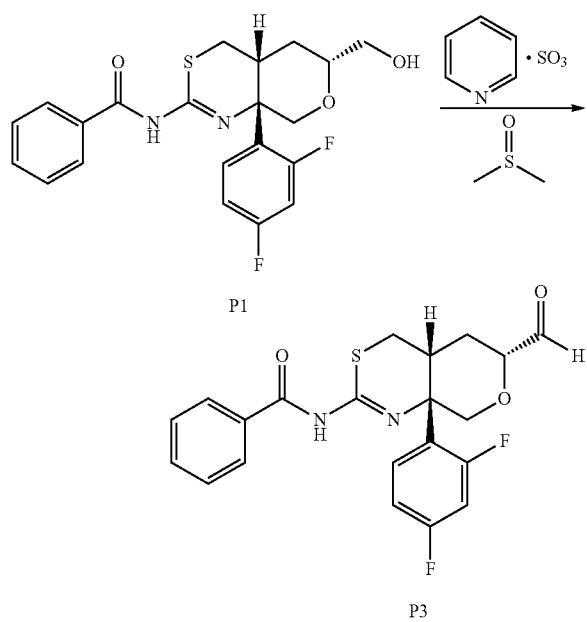

Triethylamine (16.7 mL, 120 mmol) was added in one rapid portion to a solution of N-[(4aR,6R,8aS)-8a-(2,4-difluorophenyl)-6-(hydroxymethyl)-4,4a,5,6,8,8a-hexahydropyrano[3,4-d][1,3]thiazin-2-yl]benzamide (P1) (4.18 g, 10.0 mmol) in dichloromethane (200 mL) that was immersed in a room temperature water bath. After 5 minutes, anhydrous dimethyl sulfoxide (9.94 mL, 140 mmol) was rapidly added, followed immediately by solid sulfur trioxide pyridine complex (98%, 13.0 g, 80.0 mmol) in a single portion. The resulting solution was stirred at ambient temperature for 6.5 hours, then diluted with a 1:1 mixture of water and saturated aqueous sodium chloride solution (200 mL) and stirred for 10 minutes. The aqueous layer was extracted with dichloromethane (2×200 mL), and the combined organic layers were washed with water (100 mL), washed with saturated aqueous sodium chloride solution (100 mL), dried over sodium sulfate, filtered, and concentrated in vacuo. Purification via silica gel chromatography (Gradient: 0% to 100% ethyl acetate in heptane) gave the product as a white solid. Yield: 2.81 g, 6.75 mmol, 67%. LCMS m/z 414.9 [M−H⁺]. $^1$H NMR (400 MHz, CDCl$_3$) δ 9.71 (s, 1H), 8.20 (br d, J=7 Hz, 2H), 7.50-7.56 (m, 1H), 7.36-7.49 (m, 3H), 6.86-6.99 (m, 2H), 4.23 (br d, J=12.1 Hz, 1H), 4.12 (dd, J=12.1, 2.9 Hz, 1H), 3.94 (d, J=12.5 Hz, 1H), 3.13-3.22 (m, 1H), 3.04 (dd, J=13.1, 4.1 Hz, 1H), 2.69 (dd, J=13.1, 2.9 Hz, 1H), 2.02-2.14 (m, 1H), 1.92-1.99 (m, 1H).

Preparation P4 (4aR,8aS)-2-(Benzoylamino)-8a-(2,4-difluorophenyl)-4,4a,8,8a-tetrahydropyrano[3,4-d][1,3]thiazin-6-yl trifluoromethanesulfonate (P4)

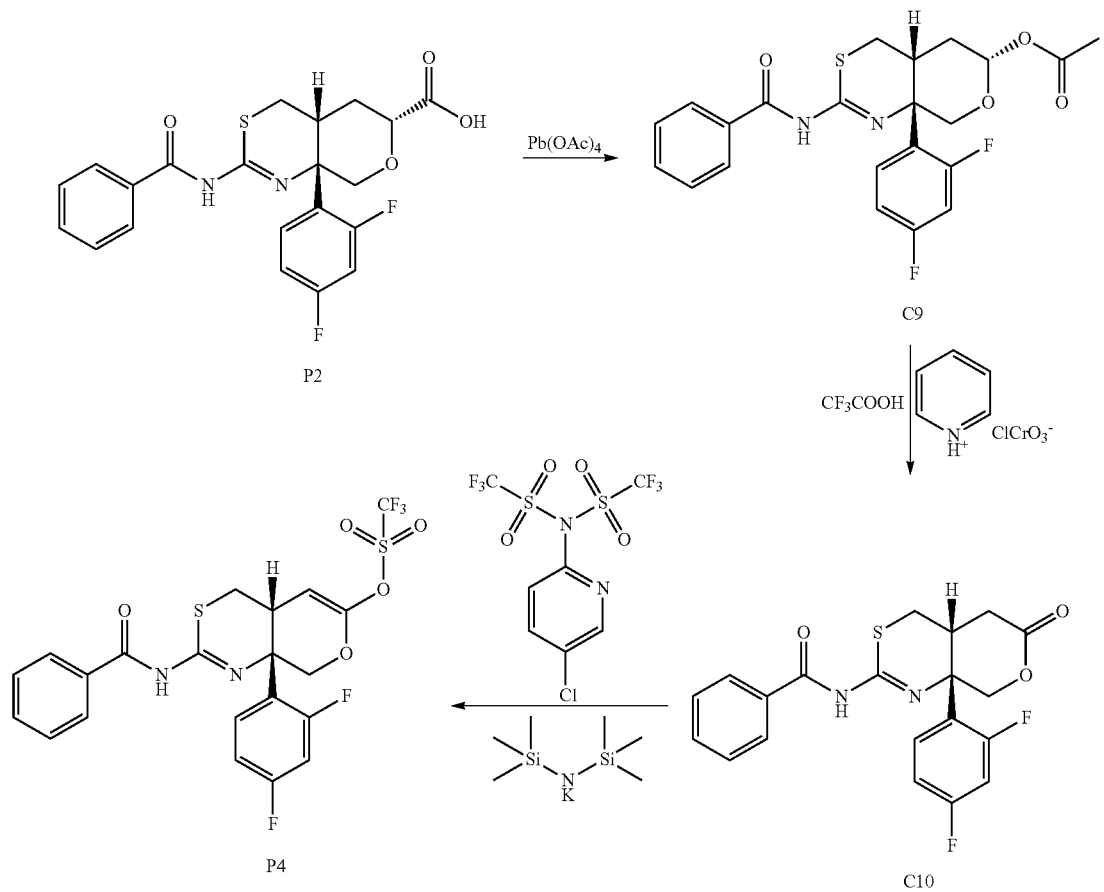

Step 1. Synthesis of (4aR,6S,8aS)-2-(benzoylamino)-8a-(2,4-difluorophenyl)-4,4a,5,6,8,8a-hexahydropyrano[3,4-d][1,3]thiazin-6-yl acetate (C9)

To a solution of (4aR,6R,8aS)-2-(benzoylamino)-8a-(2,4-difluorophenyl)-4,4a,5,6,8,8a-hexahydropyrano[3,4-d][1,3]thiazine-6-carboxylic acid (P2) (3.0 g, 6.9 mmol) in tetrahydrofuran (80 mL) and acetic acid (15 mL) was added lead(IV) acetate (19.3 g, 43.5 mmol). After stirring at room temperature for 18 hours, the reaction mixture was diluted with ethyl acetate and filtered through diatomaceous earth. The filtrate was concentrated in vacuo and the residue was purified via chromatography on silica gel (Gradient: 0% to 100% ethyl acetate in heptane), affording the product as a white solid. Yield: 1.38 g, 3.09 mmol, 45%. LCMS m/z 445.1 [M–H+]. $^1$H NMR (400 MHz, CDCl$_3$) δ 8.21 (br d, J=7 Hz, 2H), 7.50-7.56 (m, 1H), 7.36-7.49 (m, 3H), 6.87-6.98 (m, 2H), 6.31 (br d, J=3 Hz, 1H), 4.55 (d, J=12.2 Hz, 1H), 3.59 (br d, J=12 Hz, 1H), 3.44-3.52 (m, 1H), 3.05 (dd, J=13.0, 4.2 Hz, 1H), 2.63 (dd, J=13.0, 2.8 Hz, 1H), 2.38-2.48 (m, 1H), 2.19 (s, 3H), 1.80 (br dd, J=14, 4 Hz, 1H).

Step 2. Synthesis of N-[(4aR,8aS)-8a-(2,4-difluorophenyl)-6-oxo-4,4a,5,6,8,8a-hexahydropyrano[3,4-d][1,3]thiazin-2-yl]benzamide (C10)

The reaction was carried out in two batches. To a solution of (4aR,6S,8aS)-2-(benzoylamino)-8a-(2,4-difluorophenyl)-4,4a,5,6,8,8a-hexahydropyrano[3,4-d][1,3]thiazin-6-yl acetate (C9) (2.5 g, 5.6 mmol/1.66 g, 3.72 mmol) in acetonitrile (25 mL/15 mL) was added trifluoroacetic acid (6 mL/4 mL) at room temperature, followed by pyridinium chlorochromate (6.02 g, 28 mmol/3.98 g, 18.5 mmol) in one portion. The resulting reaction mixtures were stirred at room temperature for 3.5 hours, then combined and poured slowly into saturated aqueous sodium bicarbonate solution (350 mL). The aqueous layer was extracted with ethyl acetate (2×400 mL), and the combined organic layers were washed with saturated aqueous sodium bicarbonate solution (100 mL) and saturated aqueous sodium chloride solution (100 mL), dried over sodium sulfate, filtered, and concentrated in vacuo. Purification via silica gel chromatography (Gradient: 0% to 50% ethyl acetate in petroleum ether) afforded the product as a white foam containing residual dichloromethane. Corrected yield: 2.51 g, 6.24 mmol, 67%. LCMS m/z 403.0 [M+H]+. $^1$H NMR (400 MHz, CDCl$_3$) δ 8.03 (br d, J=7 Hz, 2H), 7.56-7.62 (m, 1H), 7.47-7.54 (m, 2H), 7.31-7.39 (m, 1H), 6.88-6.99 (m, 2H), 4.90 (d, J=11.5 Hz, 1H), 4.29 (d, J=11.7 Hz, 1H), 3.39-3.48 (m, 1H), 2.94-3.05 (m, 2H), 2.84 (dd, half of ABX pattern, J=18.5, 7.6 Hz, 1H), 2.68 (dd, J=13.2, 3.1 Hz, 1H).

Step 3. Synthesis of (4aR,8aS)-2-(benzoylamino)-8a-(2,4-difluorophenyl)-4,4a,8,8a-tetrahydropyrano[3,4-d][1,3]thiazin-6-yl trifluoromethanesulfonate (P4)

A mixture of N-[(4aR,8aS)-8a-(2,4-difluorophenyl)-6-oxo-4,4a,5,6,8,8a-hexahydropyrano[3,4-d][1,3]thiazin-2-yl]benzamide (C10) [2.51 g, 6.24 mmol; azeotroped with toluene (2×10 mL)] and N-(5-chloropyridin-2-yl)-1,1,1-trifluoro-N-[(trifluoromethyl)sulfonyl)sulfonyl]methanesulfonamide (Comins' reagent, 96%, 10.2 g, 24.9 mmol) in tetrahydrofuran (100 mL) was cooled to −78° C. Potassium bis(trimethylsilyl)amide (0.5 M solution in toluene, 62.4 mL, 31.2 mmol) was added drop-wise over 20 minutes, and the reaction mixture was stirred at −78° C. for 1.1 hours; after addition of aqueous sodium bicarbonate solution (50 mL), it was allowed to warm to room temperature and extracted with ethyl acetate (2×75 mL). The combined organic layers were dried over sodium sulfate, filtered, and concentrated in vacuo. Silica gel chromatography (Gradient: 0% to 60% ethyl acetate in heptane) afforded the product as a pale yellow solid. Yield: 2.43 g, 4.55 mmol, 73%. $^1$H NMR (400 MHz, CDCl$_3$) δ 7.99 (br d, J=8 Hz, 2H), 7.55-7.60 (m, 1H), 7.49 (br dd, J=8, 7 Hz, 2H), 7.39 (ddd, J=9, 9, 6.4 Hz, 1H), 6.94-7.00 (m, 1H), 6.90 (ddd, J=12.4, 8.4, 2.6 Hz, 1H), 4.82 (d, J=10.7 Hz, 1H), 4.77 (d, J=2.0 Hz, 1H), 4.17 (d, J=10.7 Hz, 1H), 3.63-3.69 (m, 1H), 2.97 (dd, J=13.3, 3.1 Hz, 1H), 2.68 (dd, J=13.3, 4.3 Hz, 1H).

Alternate synthesis of N-[(4aR,8aS)-8a-(2,4-difluorophenyl)-6-oxo-4,4a,5,6,8,8a-hexahydropyrano[3,4-d][1,3]thiazin-2-yl]benzamide (C10), from N-[(4aR,6R,8aS)-8a-(2,4-difluorophenyl)-6-formyl-4,4a,5,6,8,8a-hexahydropyrano[3,4-d][1,3]thiazin-2-yl]benzamide (P3)

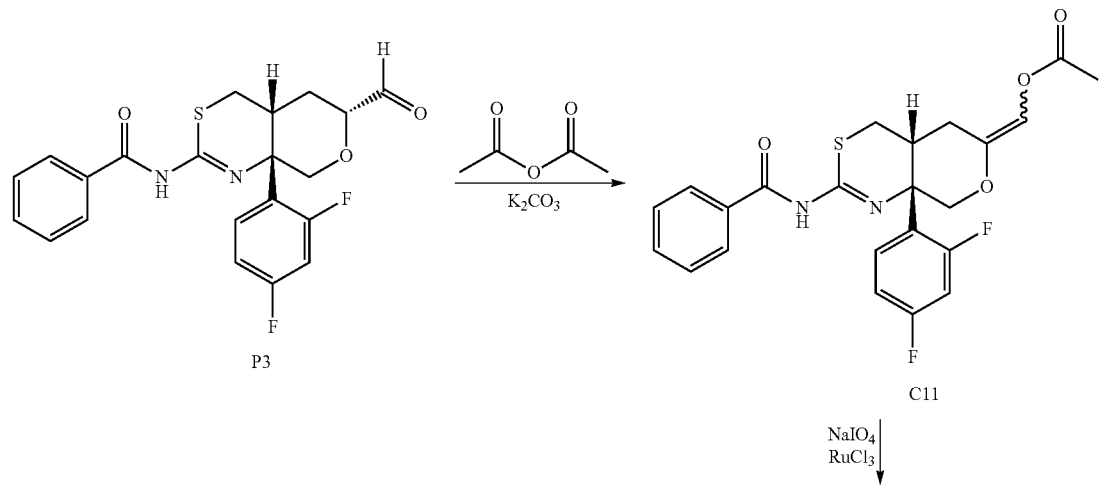

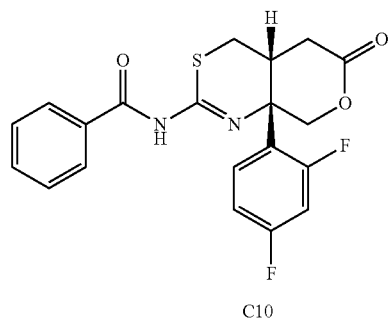

C10

Step 1. Synthesis of [(4aR,8aS)-2-(benzoylamino)-8a-(2,4-difluorophenyl)-4a,5,8,8a-tetrahydropyrano[3,4-d][1,3]thiazin-6(4H)-ylidene]methyl acetate (C11)

Acetic anhydride (1.5 mL, 16 mmol) was added to a slurry of N-[(4aR,6R,8aS)-8a-(2,4-difluorophenyl)-6-formyl-4,4a,5,6,8,8a-hexahydropyrano[3,4-d][1,3]thiazin-2-yl]benzamide (P3) (661 mg, 1.59 mmol) and potassium carbonate (1.34 g, 9.70 mmol) in acetonitrile (16 mL). After the flask had been flushed with nitrogen, the reaction mixture was heated at reflux for 2.5 hours, then allowed to cool to room temperature and stir for 18 hours. The slurry was diluted with ethyl acetate and filtered; the solids were washed with ethyl acetate, and the combined filtrates were concentrated in vacuo. Purification using silica gel chromatography (Gradient: 0% to 100% ethyl acetate in heptane) afforded the product as a white solid, which was assigned as a roughly 4:1 mixture of geometric isomers from the $^1$H NMR. Yield: 437 mg, 0.953 mmol, 60%. LCMS m/z 459.1 [M+H$^+$]. $^1$H NMR (400 MHz, CDCl$_3$), major isomer only: δ 8.09-8.32 (br s, 2H), 7.50-7.56 (m, 1H), 7.39-7.45 (m, 3H), 6.85-6.99 (m, 2H), 6.75 (d, J=1.9 Hz, 1H), 4.31 (dd, J=11.7, 1.2 Hz, 1H), 4.02 (d, J=11.8 Hz, 1H), 3.13-3.26 (m, 1H), 2.97-3.07 (m, 1H), 2.70-2.87 (m, 2H), 2.19 (s, 3H), 2.17-2.25 (m, 1H).

Step 2. Synthesis of N-[(4aR,8aS)-8a-(2,4-difluorophenyl)-6-oxo-4,4a,5,6,8,8a-hexahydropyrano[3,4-d][1,3]thiazin-2-yl]benzamide (C10)

A solution of [(4aR,8aS)-2-(benzoylamino)-8a-(2,4-difluorophenyl)-4a,5,8,8a-tetrahydropyrano[3,4-d][1,3]thiazin-6(4H)-ylidene]methyl acetate (C11) (430 mg, 0.938 mmol), ruthenium(III) chloride (5.8 mg, 28 μmol) and sodium periodate (98.5%, 407 mg, 1.87 mmol) in acetonitrile (0.5 mL) and a 1:1 mixture of 1,2-dichloroethane and water (5 mL) was stirred for 3 hours at room temperature, then allowed to stand for 18 hours without stirring. After dilution with saturated aqueous sodium thiosulfate solution (25 mL), the mixture was extracted with ethyl acetate (3×50 mL), and the combined organic layers were dried over sodium sulfate, filtered, and concentrated in vacuo. Silica gel chromatography (Gradient: 0% to 80% ethyl acetate in heptane) provided the product as a white solid. Yield: 237 mg, 0.589 mmol, 63%. LCMS m/z 403.1 [M+H$^+$]. $^1$H NMR (400 MHz, CDCl$_3$) δ 7.99 (br d, J=8 Hz, 2H), 7.49-7.54 (m, 1H), 7.43 (br dd, J=8, 7 Hz, 2H), 7.32 (ddd, J=9.0, 9.0, 6.3 Hz, 1H), 6.81-6.93 (m, 2H), 4.85 (d, J=11.7 Hz, 1H), 4.24 (d, J=11.5 Hz, 1H), 3.35-3.44 (m, 1H), 2.87-2.97 (m, 2H), 2.80 (dd, half of ABX pattern, J=18.7, 7.5 Hz, 1H), 2.63 (dd, J=13.1, 3.1 Hz, 1H).

Preparation P5

N-[(4R,4aR,6R,8aS)-8a-(2,4-Difluorophenyl)-6-(hydroxymethyl)-4-methyl-4,4a,5,6,8,8a-hexahydropyrano[3,4-d][1,3]thiazin-2-yl]benzamide (P5)

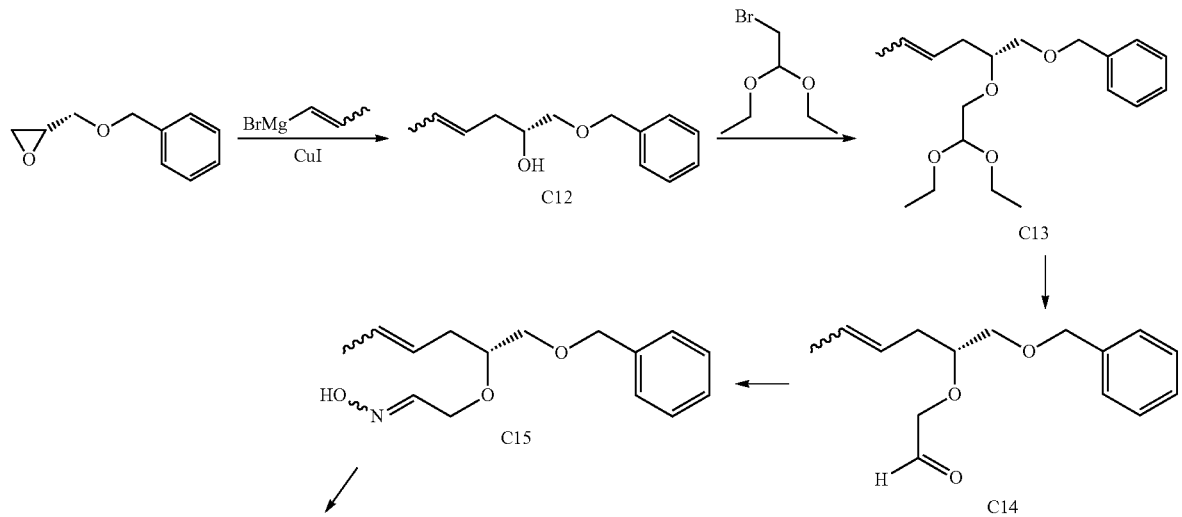

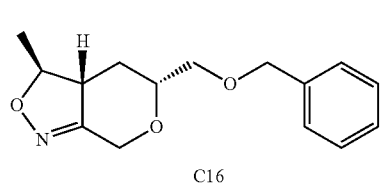 + 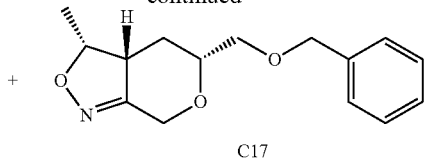

C16    C17

Step 1. Synthesis of (2R)-1-(benzyloxy)hex-4-en-2-ol (C12)

The product was obtained according to the method used for synthesis of (2R)-1-(benzyloxy)pent-4-en-2-ol (C1) in Preparation P1, except that 1-propenylmagnesium bromide was used in place of vinylmagnesium bromide. The product was obtained as a brown oil, which was used without further purification; by $^1$H NMR, this material consisted of a 1:1 mixture of geometric isomers. Yield: 140 g, 0.679 mol, 100%. $^1$H NMR (400 MHz, CDCl$_3$) δ 7.28-7.42 (m, 5H), 5.39-5.67 (m, 2H), 4.57 (s, 2H), 3.80-3.92 (m, 1H), 3.48-3.57 (m, 1H), 3.35-3.43 (m, 1H), 2.36-2.50 (br m, 1H), 2.24-2.33 (m, 1H), 2.17-2.24 (m, 1H), [1.68 (br d, J=6 Hz) and 1.64 (br d, J=7 Hz), total 3H].

Step 2. Synthesis of ({[(2R)-2-(2,2-diethoxyethoxy)hex-4-en-1-yl]oxy}methyl)benzene (C13)

(2R)-1-(Benzyloxy)hex-4-en-2-ol (C12) (150 g, 0.73 mol) was converted to the product according to the method used for synthesis of ({[(2R)-2-(2,2-diethoxyethoxy)pent-4-en-1-yl]oxy}methyl)benzene (C2) in Preparation P1, except that the initial combination of reagents was carried out at 0° C. The product was obtained as a brown oil (400 g, ≤0.73 mol), which was used for the next step without further purification. By $^1$H NMR analysis, this material contained a roughly 1:1 mixture of geometric isomers. $^1$H NMR (400 MHz, CDCl$_3$), characteristic peaks for product: δ 7.25-7.38 (m, 5H), 5.38-5.60 (m, 2H), 4.55 and 4.55 (2 s, total 2H), 2.22-2.37 (m, 2H), 1.60-1.68 (m, 3H).

Step 3. Synthesis of {[(2R)-1-(benzyloxy) hex-4-en-2-yl]oxy}acetaldehyde (C14)

To a solution of ({[(2R)-2-(2,2-diethoxyethoxy)hex-4-en-1-yl]oxy}methyl)benzene (C13) (350 g from the previous step, ≤0.64 mol) in tetrahydrofuran (1.4 L) was added aqueous hydrochloric acid (2 M, 700 mL), and the reaction mixture was stirred at 75° C. for 1 hour. Solvent was removed in vacuo and the aqueous residue was extracted with ethyl acetate (2.0 L). The combined organic layers were washed with saturated aqueous sodium chloride solution (3×500 mL), dried over sodium sulfate, filtered, and concentrated under reduced pressure. The product was obtained as a pale brown oil (210 g, ≤0.64 mol), which was taken directly to the following step.

Step 4. Synthesis of 2-{[(2R)-1-(benzyloxy)hex-4-en-2-yl]oxy}-N-hydroxyethanimine (C15)

To a mixture of {[(2R)-1-(benzyloxy)hex-4-en-2-yl]oxy}acetaldehyde (C14) (207 g, ≤0.63 mol) and sodium acetate (342 g, 4.17 mol) in aqueous ethanol (2:1 ethanol/water, 2.1 L) was added hydroxylamine hydrochloride (207 g, 2.98 mol). The reaction mixture was stirred at 60° C. for 18 hours, then concentrated in vacuo and extracted with ethyl acetate (2.0 L). The combined organic layers were dried over sodium sulfate, filtered, concentrated under reduced pressure and purified by chromatography on silica gel (Eluent: ethyl acetate in petroleum ether) to afford the product as a brown oil. By $^1$H NMR, this was assigned as a mixture of geometric isomers at both the oxime and olefin functional groups. Yield: 117 g, 0.444 mol, 70% over three steps. $^1$H NMR (400 MHz, CDCl$_3$), characteristic peaks: δ [7.42-7.48 (m) and 6.88-6.92 (m), total 1H], 7.20-7.36 (m, 5H), 5.29-5.61 (m, 2H), [4.48-4.54 (m) and 4.41-4.45 (m), total 3H], 2.13-2.32 (m, 2H), 1.54-1.65 (m, 3H).

Step 5. Synthesis of (3S,3aR,5R)-5-[(benzyloxy)methyl]-3-methyl-3,3a,4,5-tetrahydro-7H-pyrano[3,4-c][1,2]oxazole (C16) and (3R,3aR,5R)-5-[(benzyloxy)methyl]-3-methyl-3,3a,4,5-tetrahydro-7H-pyrano[3,4-c][1,2]oxazole (C17)

An aqueous solution of sodium hypochlorite (6.15% solution, 6.6 L) was slowly added to a solution of 2-{[(2R)-1-(benzyloxy)hex-4-en-2-yl]oxy}-N-hydroxyethanimine (C15) (660 g, 2.51 mol) and triethylamine (19 g, 0.19 mol) in dichloromethane (6.6 L) at 25° C. After completion of the addition, the reaction mixture was stirred at 25° C. for 30 minutes. The organic layer was washed with water (3×3 L), dried over sodium sulfate, filtered, and concentrated in vacuo. Purification via chromatography on silica gel (Eluent: ethyl acetate in petroleum ether) provided (3S,3aR,5R)-5-[(benzyloxy)methyl]-3-methyl-3,3a,4,5-tetrahydro-7H-pyrano[3,4-c][1,2]oxazole (C16) as a white solid. Yield: 90 g, 0.34 mol, 14%. The indicated relative stereochemistry of compound C16 was assigned based on nuclear Overhauser enhancement studies, which revealed interactions of the methine proton on carbon 3a with both the protons of the methyl group on carbon 3 and the methine proton on carbon 5. LCMS m/z 261.9 [M+H$^+$]. $^1$H NMR (400 MHz, CDCl$_3$) δ 7.24-7.39 (m, 5H), 4.69 (d, J=13.7 Hz, 1H), 4.57 (AB quartet, J$_{AB}$=12.2 Hz, Δv$_{AB}$=13.8 Hz, 2H), 4.13-4.25 (m, 2H), 3.62-3.70 (m, 1H), 3.55 (dd, half of ABX pattern, J=10, 6 Hz, 1H), 3.47 (dd, half of ABX pattern, J=10, 4 Hz, 1H), 2.93 (br ddd, J=11, 11, 7 Hz, 1H), 2.11 (br dd, J=12.6, 6.8 Hz, 1H), 1.45-1.56 (m, 1H), 1.45 (d, J=6.2 Hz, 3H).

Also obtained from the chromatographic separation was (3R,3aR,5R)-5-[(benzyloxy)methyl]-3-methyl-3,3a,4,5-tetrahydro-7H-pyrano[3,4-c][1,2]oxazole (C17), as a brown oil. Yield: 126 g, 0.482 mol, 19%. The indicated relative stereochemistry of compound C17 was assigned based on nuclear Overhauser enhancement studies, which revealed interactions of the methine proton on carbon 3a with both the methine proton on carbon 3 and the methine proton on carbon 5. LCMS m/z 261.9 [M+H⁺]. ¹H NMR (400 MHz, CDCl₃) δ 7.26-7.39 (m, 5H), 4.76-4.86 (m, 1H), 4.75 (d, J=13.5 Hz, 1H), 4.58 (AB quartet, $J_{AB}$=12.2 Hz, $v_{AB}$=12.4 Hz, 2H), 4.19 (dd, J=13.5, 1.2 Hz, 1H), 3.63-3.70 (m, 1H), 3.57 (dd, half of ABX pattern, J=10.2, 6.0 Hz, 1H), 3.49 (dd, half of ABX pattern, J=10.1, 4.2 Hz, 1H), 3.36 (br ddd, J=11.4, 11.4, 6.3 Hz, 1H), 1.86 (ddd, J=12.8, 6.4, 1.2 Hz, 1H), 1.55-1.66 (m, 1H), 1.16 (d, J=6.6 Hz, 3H).

Step 6. Synthesis of (3S,3aR,5R,7aS)-5-[(benzyloxy)methyl]-7a-(2,4-difluorophenyl)-3-methylhexahydro-1H-pyrano[3,4-c][1,2]oxazole (C18)

The product, obtained as a yellow oil, was prepared from (3S,3aR,5R)-5-[(benzyloxy)methyl]-3-methyl-3,3a,4,5-tetrahydro-7H-pyrano[3,4-c][1,2]oxazole (C16) according to the general procedure for the synthesis of (3aR,5R,7aS)-5-[(benzyloxy)methyl]-7a-(2,4-difluorophenyl)hexahydro-1H-pyrano[3,4-c][1,2]oxazole (C5) in Preparation P1. Yield: 21.5 g, 57.2 mmol, 48%. LCMS m/z 376.2 [M+H⁺]. ¹H NMR (400 MHz, CDCl₃) δ 7.98 (ddd, J=9.1, 9.1, 6.8 Hz, 1H), 7.28-7.40 (m, 5H), 6.87-6.93 (m, 1H), 6.80 (ddd, J=11.9, 8.6, 2.6 Hz, 1H), 4.60 (AB quartet, $J_{AB}$=12.1 Hz, $\Delta v_{AB}$=19.9 Hz, 2H), 3.99-4.06 (m, 1H), 3.97 (dd, half of ABX pattern, J=12.9, 2.0 Hz, 1H), 3.80-3.88 (m, 2H), 3.56 (dd, half of ABX pattern, J=10.2, 6.3 Hz, 1H), 3.49 (dd, half of ABX pattern, J=10.2, 4.1 Hz, 1H), 2.81-2.87 (m, 1H), 2.04 (ddd, J=14.2, 7.6, 2.8 Hz, 1H), 1.48-1.59 (m, 1H), 0.79 (d, J=6.4 Hz, 3H).

Step 7. Synthesis of (1 S)-1-[(2R,4R,5S)-5-amino-2-[(benzyloxy)methyl]-5-(2,4-difluorophenyl)tetrahydro-2H-pyran-4-yl]ethanol (C19)

The product, obtained as a yellow oil, was prepared from (3S,3aR,5R,7aS)-5-[(benzyloxy)methyl]-7a-(2,4-difluorophenyl)-3-methyl hexahydro-1H-pyrano[3,4-c][1,2]oxazole (C18) according to the general procedure for the synthesis of [(2R,4R,5S)-5-amino-2-[(benzyloxy)methyl]-5-(2,4-difluorophenyl)tetrahydro-2H-pyran-4-yl]methanol (C6) in Preparation P1. Yield: 13.96 g, 37.00 mmol, 98%. LCMS m/z 378.2 [M+H⁺]. ¹H NMR (400 MHz, CDCl₃), characteristic peaks: δ 7.65-7.78 (br m, 1H), 7.27-7.40 (m, 5H), 6.93-7.02 (br m, 1H), 6.80 (ddd, J=12.6, 8.5, 2.6 Hz, 1H), 4.06 (dd, J=11.7, 2.2 Hz, 1H), 3.53 (dd, J=10.2, 3.7 Hz, 1H), 2.50-2.61 (br m, 1H), 1.62 (ddd, J=14, 4, 2.5 Hz, 1H), 0.89 (d, J=6.6 Hz, 3H).

Step 8. Synthesis of N-{[(3S,4R,6R)-6-[(benzyloxy)methyl]-3-(2,4-difluorophenyl)-4-[(1S)-1-hydroxyethyl]tetrahydro-2H-pyran-3-yl]carbamothioyl}benzamide (C20)

The product was prepared from (1 S)-1-[(2R,4R,5S)-5-amino-2-[(benzyloxy)methyl]-5-(2,4-difluorophenyl)tetrahydro-2H-pyran-4-yl]ethanol (C19) according to the general procedure for the synthesis of N-{[(3S,4R,6R)-6-[(benzyloxy)methyl]-3-(2,4-difluorophenyl)-4-(hydroxymethyl)tetrahydro-2H-pyran-3-yl]carbamothioyl}benzamide (C7) in Preparation P1. In this case, after concentration of the reaction mixture in vacuo, the residue was chromatographed on silica gel (Gradient: 0% to 50% ethyl acetate in heptane) to afford the product as a yellow foam. Yield: 13.36 g, 24.71 mmol, 67%. LCMS m/z 539.2 [M−H⁺].

Step 9. Synthesis of N-[(4R,4aR,6R,8aS)-6-[(benzyloxy)methyl]-8a-(2,4-difluorophenyl)-4-methyl-4,4a,5,6,8,8a-hexahydropyrano[3,4-d][1,3]thiazin-2-yl]benzamide (C21)

Diethyl azodicarboxylate (21.3 mL, 136 mmol) was added drop-wise to a solution of triphenylphosphine (35.7 g, 136 mmol) in tetrahydrofuran (850 mL), and the mixture was stirred for 30 minutes before being cooled in an ice bath. A solution of N-{[(3S,4R,6R)-6-[(benzyloxy)methyl]-3-(2,4-difluorophenyl)-4-[(1S)-1-hydroxyethyl]tetrahydro-2H-pyran-3-yl]carbamothioyl}benzamide (C20) (24.5 g, 45.3 mmol) in tetrahydrofuran (115 mL) was added drop-wise to the reaction mixture, which was then stirred for 1 hour under ice cooling. After concentration in vacuo, the residue was loaded onto a silica gel column that had been equilibrated with dichloromethane, and the column was eluted with 1:1 ethyl acetate/heptane. Fractions containing product were combined and concentrated under reduced pressure; the resulting material was triturated with 15% ethyl acetate in heptane, and the solid was removed via filtration. The filtrate was concentrated in vacuo and chromatographed on silica gel (Gradient: 20% to 40% ethyl acetate in heptane), affording the product as a white solid. Yield: 17.23 g, 32.97 mmol, 73%. LCMS m/z 523.2 [M+H⁺]. ¹H NMR (400 MHz, CDCl₃) δ 8.23 (br d, J=6.5 Hz, 2H), 7.49-7.55 (m, 1H), 7.36-7.48 (m, 3H), 7.24-7.36 (m, 5H), 6.84-6.96 (m, 2H), 4.58 (AB quartet, $J_{AB}$=12.0 Hz, $\Delta v_{AB}$=25.0 Hz, 2H), 4.18 (dd, J=12.2, 1.7 Hz, 1H), 3.87-3.94 (m, 1H), 3.84 (d, J=12.2 Hz, 1H), 3.63 (dd, half of ABX pattern, J=10.2, 6.4 Hz, 1H), 3.50 (dd, half of ABX pattern, J=10.2, 4.4 Hz, 1H), 3.23-3.31 (m, 1H), 2.88-2.96 (m, 1H), 1.61-1.79 (m, 2H), 1.25 (d, J=6.9 Hz, 3H).

Step 10. Synthesis of N-[(4R,4aR,6R,8aS)-8a-(2,4-difluorophenyl)-6-(hydroxymethyl)-4-methyl-4,4a,5,6,8,8a-hexahydropyrano[3,4-d][1,3]thiazin-2-yl]benzamide (P5)

The product was prepared from N-[(4R,4aR,6R,8aS)-6-[(benzyloxy)methyl]-8a-(2,4-difluorophenyl)-4-methyl-4,4a,5,6,8,8a-hexahydropyrano[3,4-d][1,3]thiazin-2-yl]benzamide (C21) according to the general procedure for the synthesis of N-[(4aR,6R,8aS)-8a-(2,4-difluorophenyl)-6-(hydroxymethyl)-4,4a,5,6,8,8a-hexahydropyrano[3,4-d][1,3]thiazin-2-yl]benzamide (P1) in Preparation P1. In this case, the combined crude product from two similar reactions was triturated with dichloromethane rather than being purified by chromatography. The filtrate from the trituration was concentrated in vacuo, and a second crop of material was obtained via a second trituration with dichloromethane, affording the product in both cases as a white solid. Total yield: 23.12 g, 53.46 mmol, 79%. LCMS m/z 433.2 [M+H⁺]. ¹H NMR (400 MHz, CD₃OD) δ 8.12 (br d, J=7 Hz, 2H), 7.51-7.57 (m, 1H), 7.40-7.49 (m, 3H), 7.02-7.11 (m, 2H), 4.15 (br d, J=12 Hz, 1H), 3.91 (d, J=11.9 Hz, 1H), 3.71-3.78 (m, 1H), 3.60 (d, J=5.2 Hz, 2H), 3.19-3.28 (br m, 1H), 2.97-3.06 (br m, 1H), 1.74-1.82 (m, 1H), 1.49-1.62 (m, 1H), 1.26 (d, J=7.0 Hz, 3H).

Preparation P6

(4R,4aR,8aS)-2-(Benzoylamino)-8a-(2,4-difluorophenyl)-4-methyl-4,4a,8,8a-tetrahydropyrano[3,4-d][1,3]thiazin-6-yl trifluoromethanesulfonate (P6)

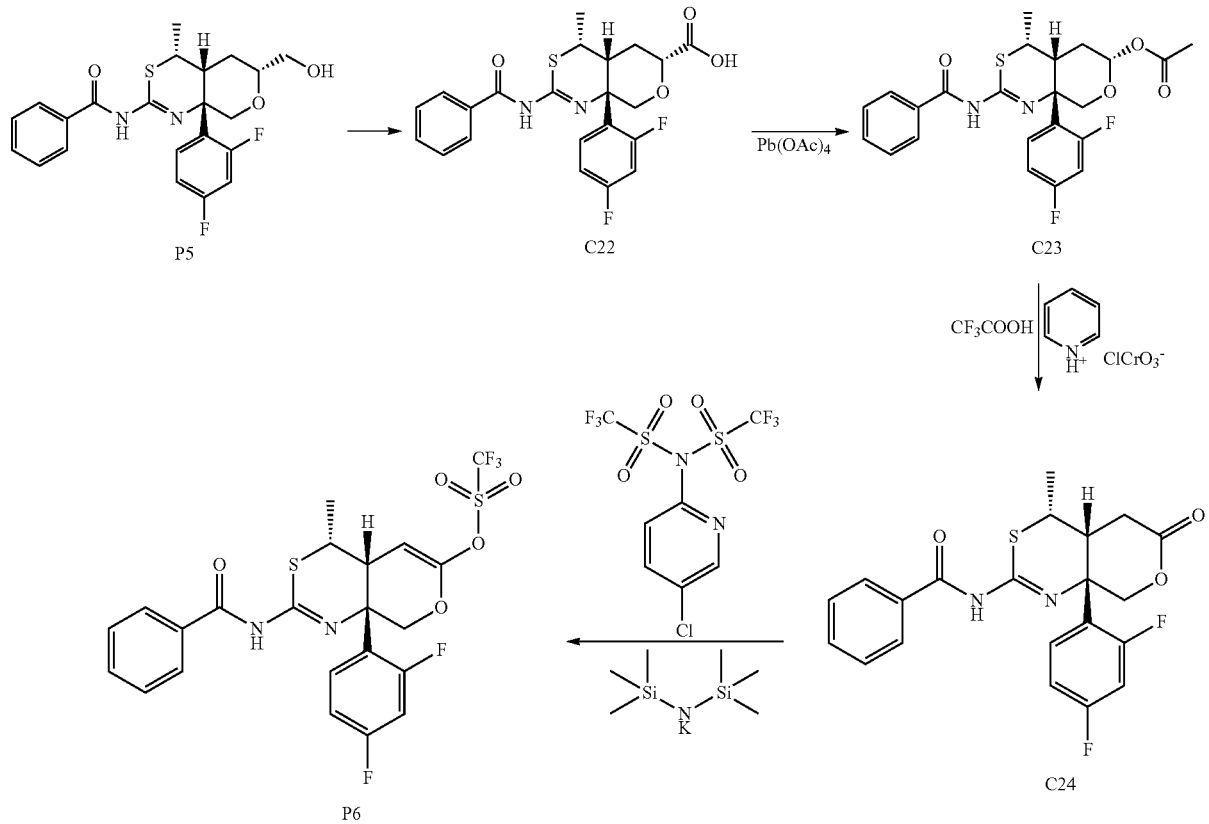

Step 1. Synthesis of (4R,4aR,6R,8aS)-2-(benzoylamino)-8a-(2,4-difluorophenyl)-4-methyl-4,4a,5,6,8,8a-hexahydropyrano[3,4-d][1,3]thiazine-6-carboxylic acid (C22)

The product, obtained as a pink/white solid, was prepared from N-[(4R,4aR,6R,8aS)-8a-(2,4-difluorophenyl)-6-(hydroxymethyl)-4-methyl-4,4a,5,6,8,8a-hexahydropyrano[3,4-d][1,3]thiazin-2-yl]benzamide (P5) according to the procedure for the synthesis of (4aR,6R,8aS)-2-(benzoylamino)-8a-(2,4-difluorophenyl)-4,4a,5,6,8,8a-hexahydropyrano[3,4-d][1,3]thiazine-6-carboxylic acid (P2) in Preparation 2. Yield: 2.92 g, 6.54 mmol, 95%. LCMS m/z 447.2 [M+H$^+$]. $^1$H NMR (400 MHz, CD$_3$OD) δ 8.08-8.12 (m, 2H), 7.52-7.58 (m, 1H), 7.41-7.49 (m, 3H), 7.02-7.11 (m, 2H), 4.34 (dd, J=12.1, 2.7 Hz, 1H), 4.20 (br d, J=11.9 Hz, 1H), 3.98 (d, J=11.9 Hz, 1H), 3.18-3.26 (m, 1H), 3.06 (ddd, J=12.1, 3.9, 3.9 Hz, 1H), 2.15 (ddd, J=13.6, 4.0, 2.9 Hz, 1H), 1.71-1.83 (m, 1H), 1.27 (d, J=6.8 Hz, 3H).

Step 2. Synthesis of (4R,4aR,6S,8aS)-2-(benzoylamino)-8a-(2,4-difluorophenyl)-4-methyl-4,4a,5,6,8,8a-hexahydropyrano[3,4-d][1,3]thiazin-6-yl acetate (C23)

To a solution of (4R,4aR,6R,8aS)-2-(benzoylamino)-8a-(2,4-difluorophenyl)-4-methyl-4,4a,5,6,8,8a-hexahydropyrano[3,4-d][1,3]thiazine-6-carboxylic acid (C22) (5.0 g, 10.0 mmol) in tetrahydrofuran (130 mL) and acetic acid (25 mL) was added lead(IV) acetate (31.2 g, 70.4 mmol). After stirring at room temperature for 18 hours, the reaction mixture was diluted with ethyl acetate and filtered through diatomaceous earth. The filtrate was concentrated in vacuo and the residue was purified via chromatography on silica gel (Gradient: 0% to 100% ethyl acetate in heptane), affording the product as a white solid. Yield: 2.75 g, 5.98 mmol, 50%. $^1$H NMR (400 MHz, CDCl$_3$) characteristic peaks δ 8.20 (br d, J=7.0 Hz, 2H), 7.35-7.55 (m, 4H), 6.87-7.01 (m, 2H), 6.34 (br d, J=2.5 Hz, 1H), 4.55 (d, J=12.1 Hz, 1H), 3.59 (d, J=12.3 Hz, 1H), 3.21-3.31 (m, 2H), 1.84 (dd, J=14.6, 3.4 Hz, 1H), 1.26 (d, J=6.8 Hz, 3H).

Step 3. Synthesis of N-[(4R,4aR,8aS)-8a-(2,4-difluorophenyl)-4-methyl-6-oxo-4,4a,5,6,8,8a-hexahydropyrano[3,4-d][1,3]thiazin-2-yl]benzamide (C24)

The reaction was carried out in two batches. To a solution of (4R,4aR,6S,8aS)-2-(benzoylamino)-8a-(2,4-difluorophenyl)-4-methyl-4,4a,5,6,8,8a-hexahydropyrano[3,4-d][1,3]thiazin-6-yl acetate (C23) (2.75 g, 6.0 mmol) in acetonitrile (30 mL) was added trifluoroacetic acid (11.5 mL) at room temperature, followed by pyridinium chlorochromate (6.57 g, 29.9 mmol) in one portion. The resulting reaction mixtures were stirred at room temperature for 16 hours, then combined and poured slowly into saturated aqueous sodium bicarbonate solution (350 mL). The aqueous layer was extracted with ethyl acetate (2×400 mL), and the combined organic layers were washed with saturated aqueous sodium bicarbonate solution (100 mL) and saturated aqueous sodium chloride solution (100 mL), dried over sodium sulfate, filtered, and concentrated in vacuo. Purification via silica gel chromatography (Gradient: 0% to 100% ethyl acetate in petroleum ether) afforded the product as a white foam containing residual dichloromethane. Yield: 1.36 g, 3.27 mmol, 55%. LCMS m/z 417.2 [M+H]$^+$. $^1$H NMR (400 MHz, CDCl$_3$) δ 8.01 (br s, 2H), 7.58-7.62 (m, 1H), 7.49-7.53 (m, 2H), 7.32 (m, 1H), 6.88-7.01 (m, 2H), 4.92 (d, J=11.5 Hz, 1H), 4.30 (d, J=11.5 Hz, 1H), 3.20-3.26 (m, 2H), 2.78-2.81 (m, 2H), 1.24 (d, J=6.9 Hz, 3H).

Step 4. Synthesis of (4R,4aR,8aS)-2-(benzoylamino)-8a-(2,4-difluorophenyl)-4-methyl-4,4a,8,8a-tetrahydropyrano[3,4-d][1,3]thiazin-6-yl trifluoromethanesulfonate (P6)

A mixture of N-[(4R,4aR,8aS)-8a-(2,4-difluorophenyl)-4-methyl-6-oxo-4,4a,5,6,8,8a-hexahydropyrano[3,4-d][1,3]thiazin-2-yl]benzamide (C24) [1.36 g, 3.27 mmol; azeotroped with toluene (2×10 mL)] and N-(5-chloropyridin-2-yl)-1,1,1-trifluoro-N-[(trifluoromethyl)sulfonyl]methanesulfonamide (Comins' reagent, 96%, 5.34 g, 13.1 mmol) in tetrahydrofuran (53 mL) was cooled to −78° C. Potassium bis(trimethylsilyl)amide (0.5 M solution in toluene, 32.7 mL, 16.3 mmol) was added drop-wise over 20 minutes, and the reaction mixture was stirred at −78° C. for 1.1 hours; after addition of aqueous sodium bicarbonate solution (30 mL), it was allowed to warm to room temperature and extracted with ethyl acetate (2×50 mL). The combined organic layers were dried over sodium sulfate, filtered, and concentrated in vacuo. Silica gel chromatography (Gradient: 0% to 50% ethyl acetate in heptane) afforded the product as a pale yellow solid. Yield: 1.55 g, 2.83 mmol, 87%. LCMS m/z 549.2 [M+H]$^+$. $^1$H NMR (400 MHz, CDCl$_3$) δ 7.97-7.99 (m, 2H), 7.56-7.60 (m, 1H), 7.47-7.52 (m, 2H), 7.35 (td, J=9.0, 6.5 Hz, 1H), 6.87-6.97 (m, 2H), 4.83 (d, J=10.6 Hz, 1H), 4.77 (d, J=1.8 Hz, 1H), 4.18 (d, J=10.6 Hz, 1H), 3.43 (br d, J=2.0 Hz, 1H), 3.12 (qd, J=7.0, 2.4 Hz, 1H), 1.28 (d, J=7.0 Hz, 3H).

Examples 1-30

(4aR,6R,8aS)-8a-(2,4-Difluorophenyl)-6-phenyl-4,4a,5,6,8,8a-hexahydropyrano[3,4-d][1,3]thiazin-2-amines (1-30)

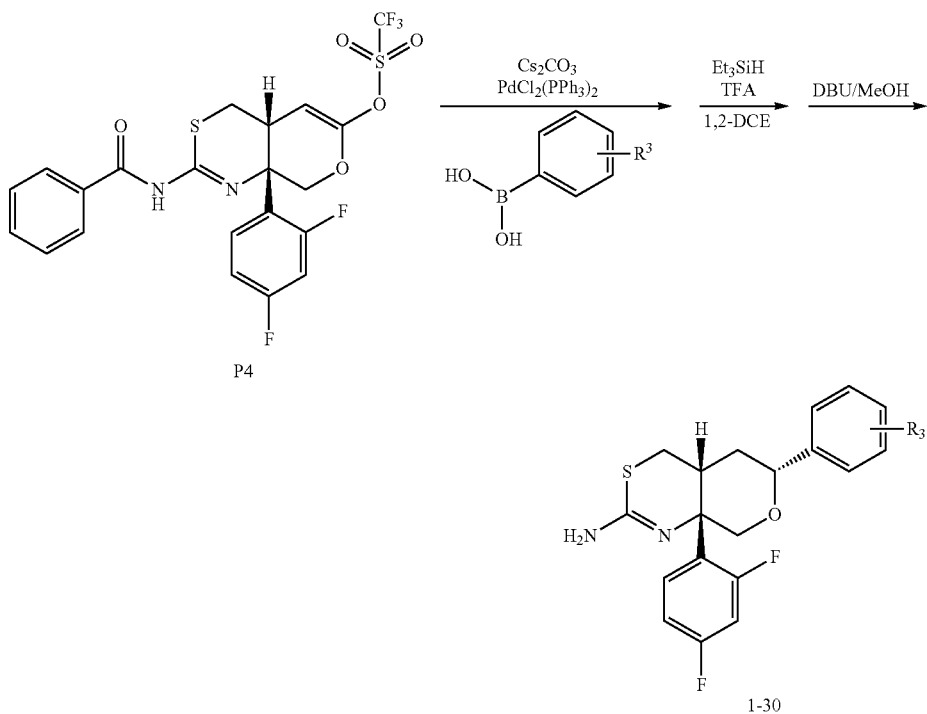

In the scheme above it is to be understood that the appropriately substituted boronic acid can have one R$^3$ group as depicted or up to three independently selected R$^3$ groups. The final compounds can then correspondingly have between one and three R$^3$ groups on the phenyl.

Step 1. Synthesis of (4aR,6R,8aS)-8a-(2,4-difluorophenyl)-6-phenyl-4,4a,5,6,8,8a-hexahydropyrano[3,4-d][1,3]thiazin-2-amines (1-30)

To the requisite aryl boronic acids (0.15 mmol, 2.0 equiv) in 2-dram vials was added a solution of (4aR,8aS)-2-(benzoylamino)-8a-(2,4-difluorophenyl)-4,4a,8,8a-tetrahydropyrano[3,4-d][1,3]thiazin-6-yl trifluoromethanesulfonate (P4) (40 mg, 75 μmol, 1.0 equiv) in tetrahydrofuran (1 mL). An aqueous 2 M solution of cesium carbonate (0.19 mL, 0.38 mmol, 5.0 equiv) and dichlorobis(triphenylphosphine)palladium(II) (~3 mg, 4 μmol, 0.05 equiv) were added to each vial. The reactions were de-gassed and shaken at 65° C. for 17 hours. The reaction mixtures were each partitioned between water (1.5 mL) and ethyl acetate (2.4 mL) and the organic layer was separated. The extraction was repeated twice and the organics from each individual reaction were combined and passed through solid phase extraction cartridges containing sodium sulfate (6 mL cartridge, approximately 1 g bed weight). The filtrates were concentrated in vacuo. The crude residues (~0.1 mmol, 1 equiv) were dissolved in 1,2-dichloroethane (0.25 mL) and cooled in a dry ice box for ~2 minutes. Triethylsilane (0.25 mL, 1.5 mmol, 15 equiv) and trifluoroacetic acid (0.25 mL) were added and the vials were shaken at room temperature for 2 hours. The reaction mixtures were concentrated and each residue partitioned between a half saturated solution of sodium bicarbonate (1.5 mL) and ethyl acetate (2.5 mL). The extraction was repeated twice and the organics from each individual reaction were combined and passed through solid phase extraction cartridges containing sodium sulfate (6 mL cartridge, approximately 1 g bed weight). The filtrates were concentrated in vacuo. The crude residues (~75 μmol) were dissolved in methanol (0.5 mL) and 1,8-diazabicyclo[5.4.0]undec-7-ene (13 μL, 85 μmol, 1 equiv) was added. The reaction vials were shaken at 65° C. for 16 hours and then concentrated in vacuo. The organics from each individual reaction were combined and passed through solid phase extraction cartridges containing sodium sulfate (6 mL cartridge, approximately 1 g bed weight). After concentration in vacuo, dissolution in dimethyl sulfoxide (1 mL) and filtration through a Waters Oasis® filter plate to remove particulates, purification was carried out via reversed-phase HPLC (Column: Waters XBridge C18, 5 μm; Mobile phase A: 0.03% ammonium hydroxide in water (v/v); Mobile phase B: 0.03% ammonium hydroxide in acetonitrile (v/v); Gradient: 20% to 100% B, or 5% to 100% B). See Table 1 for characterization data.

TABLE 1

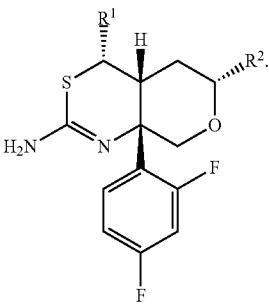

$R^1 = H$

| Example # | Structure $R^2$ | Calc'd Exact Mol. Wt. | Mass. Spec. m/z (M + H$^+$) | HPLC Retention Time (min) |
|---|---|---|---|---|
| 1 | 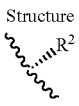 | 378.10 | 379.38 | 2.45[1] |
| 2 | 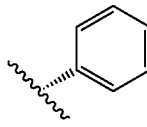 | 378.10 | 379.42 | 2.28[1] |
| 3 | 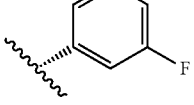 | 378.10 | 379.44 | 2.30[1] |
| 4 | 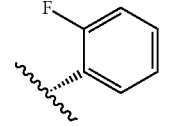 | 396.09 | 397.38 | 2.35[1] |
| 5 | 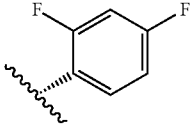 | 396.09 | 397.37 | 2.51[1] |
| 6 | 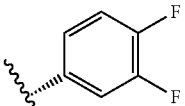 | 374.13 | 375.40 | 2.55[1] |
| 7 | 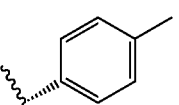 | 374.13 | 375.44 | 2.34[1] |
| 8 | 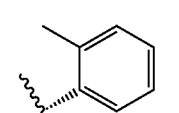 | 392.12 | 393.45 | 2.43[1] |
| 9 | 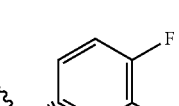 | 392.12 | 393.45 | 2.44[1] |

TABLE 1-continued
R¹ = H
| Example # | Structure R² | Calc'd Exact Mol. Wt. | Mass. Spec. m/z (M + H⁺) | HPLC Retention Time (min) |
|---|---|---|---|---|
| 10 |  | 392.12 | 393.45 | 2.45[1] |
| 11 | 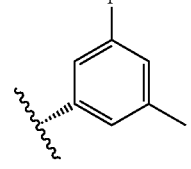 | 392.12 | 393.45 | 2.44[1] |
| 12 | 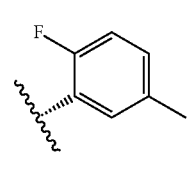 | 394.07 | 395.32 | 2.45[1] |
| 13 | 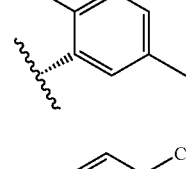 | 428.10 | 429.40 | 2.53[1] |
| 14 | 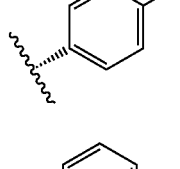 | 428.10 | 429.41 | 2.55[1] |
| 15 | 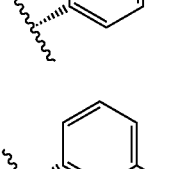 | 444.09 | 445.41 | 2.60[1] |
| 16 | 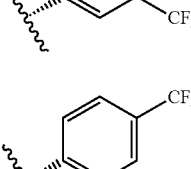 | 390.12 | 391.45 | 2.25[1] |
| 17 | 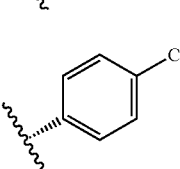 | 390.12 | 391.45 | 2.30[1] |
| 18 | 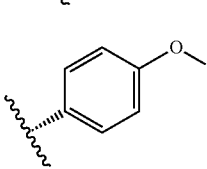 | 408.11 | 409.41 | 2.29[1] |
| 19 | 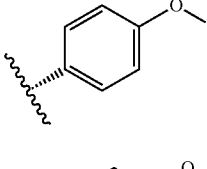 | 408.11 | 409.45 | 2.60[1] |
| 20 | 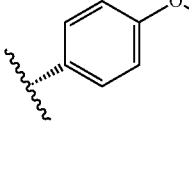 | 408.11 | 409.46 | 2.35[1] |
| 21 | 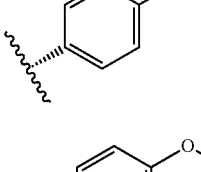 | 408.11 | 409.46 | 2.37[1] |
| 22 | 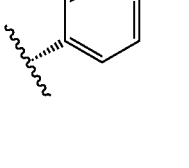 | 408.11 | 409.43 | 2.36[1] |
| 23 | 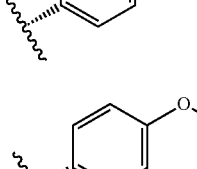 | 404.14 | 405.46 | 2.40[1] |

TABLE 1-continued

Structure (R¹ = H):
A pyrano-thiazine core with 2-amino, 8a-(2,4-difluorophenyl), and R² substituent.

| Example # | Structure (R²) | Calc'd Exact Mol. Wt. | Mass. Spec. m/z (M + H⁺) | HPLC Retention Time (min) |
|---|---|---|---|---|
| 24 | 3-(methoxymethyl)phenyl | 404.14 | 405.46 | 2.20[1] |
| 25 | 4-(methoxymethyl)phenyl | 404.14 | 405.46 | 2.19[1] |
| 26 | 2,3-dihydrobenzofuran-5-yl | 402.12 | 403.39 | 2.26[1] |
| 27 | benzo[1,3]dioxol-5-yl | 404.10 | 405.39 | 2.23[1] |
| 28 | 4-(1-methoxyethyl)phenyl | 418.15 | 419.47 | 2.30[1] |
| 29 | 3-cyanophenyl | 385.11 | 386.06 | 2.39[1] |
| 30 | 4-(difluoromethyl)phenyl | 410.11 | 411.33 | 2.37[1] |

1. HPLC conditions:
Waters Atlantis dC18, 4.6 × 50 mm, 5 μm;
Mobile phase A: 0.05% trifluoroacetic acid in water (v/v);
Mobile phase B: 0.05% trifluoroacetic acid in acetonitrile (v/v);
Gradient: 5% to 95% B, linear over 4.0 minutes;
Flow rate: 2 mL/min.

Example 31

4-[(4aR,6R,8aS)-2-Amino-8a-(2,4-difluorophenyl)-4,4a,5,6,8,8a-hexahydropyrano[3,4-d][1,3]thiazin-6-yl]benzonitrile (31)

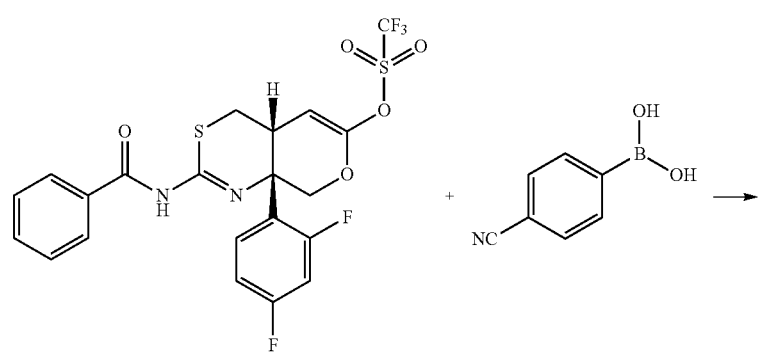

P4

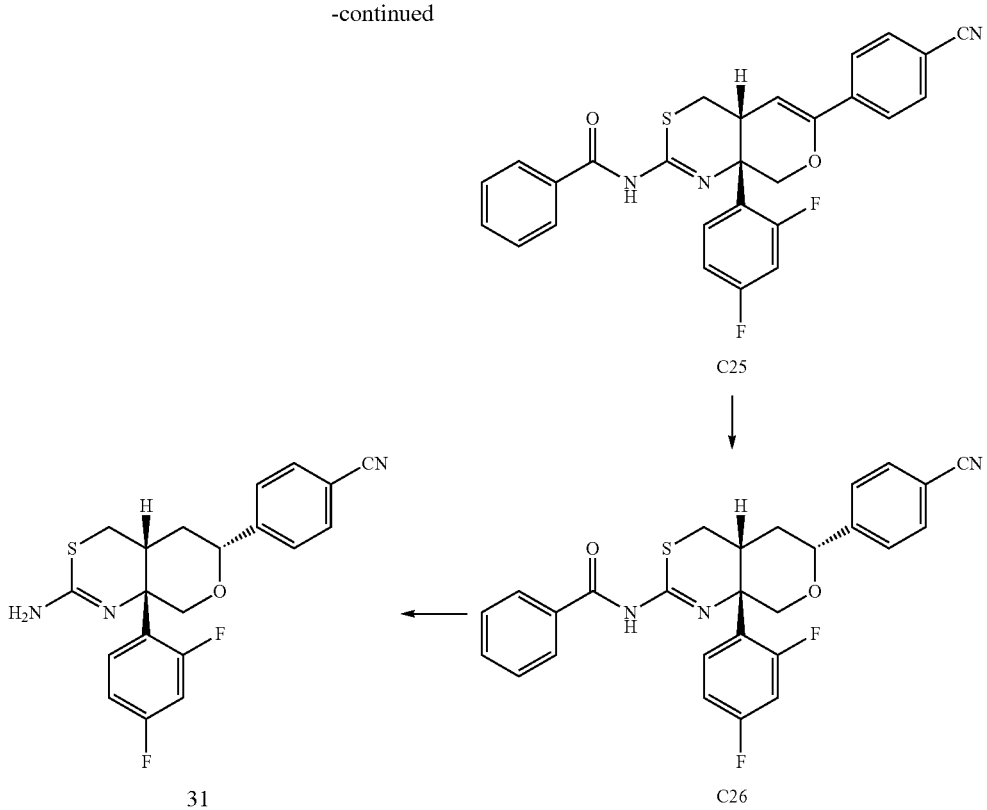

Step 1. Synthesis of N-[(4aR,8aS)-6-(4-cyanophenyl)-8a-(2,4-difluorophenyl)-4,4a,8,8a-tetrahydropyrano[3,4-d][1,3]thiazin-2-yl]benzamide (C25)

(4-Cyanophenyl)boronic acid (55 mg, 0.37 mmol, 2.0 equiv) was added to a solution of (4aR,8aS)-2-(benzoylamino)-8a-(2,4-difluorophenyl)-4,4a,8,8a-tetrahydropyrano[3,4-d][1,3]thiazin-6-yl trifluoromethanesulfonate (P4) (100 mg, 0.19 mmol, 1.0 equiv) in tetrahydrofuran (1.5 mL). An aqueous 2 M solution of cesium carbonate (0.47 mL, 0.935 mmol, 5.0 equiv) and dichlorobis(triphenylphosphine)palladium(II) (6.4 mg, 9 μmol, 0.05 equiv) were added. The reaction was de-gassed and stirred at 65° C. for 17 hours. The reaction mixture was partitioned between water (10 mL) and ethyl acetate (20 mL) and the organic layer separated. The extraction was repeated twice and the combined organics were washed with saturated aqueous sodium chloride solution (10 mL), dried over sodium sulfate, filtered and concentrated in vacuo. Chromatography on silica gel (Gradient: 0% to 50% ethyl acetate in heptane) afforded the product as a white solid. Yield: 64 mg, 70%. LCMS m/z 488.3 [M+H$^+$].

Step 2. Synthesis of N-[(4aR,6R,8aS)-6-(4-cyanophenyl)-8a-(2,4-difluorophenyl)-4,4a,5,6,8,8a-hexahydropyrano[3,4-d][1,3]thiazin-2-yl]benzamide (C26)

N-[(4aR,8aS)-6-(4-Cyanophenyl)-8a-(2,4-difluorophenyl)-4,4a,8,8a-tetrahydropyrano[3,4-d][1,3]thiazin-2-yl]benzamide (C25) (64 mg, 0.13 mmol, 1 equiv) was dissolved in 1,2-dichloroethane (2.0 mL) and cooled to 0° C. Triethylsilane (0.32 mL, 2.0 mmol, 15 equiv) and trifluoroacetic acid (0.5 mL) were added and reaction mixture was stirred at room temperature for 16 hours. The reaction mixture was neutralized by addition of a saturated solution of sodium bicarbonate (10 mL) and extracted with ethyl acetate (3×20 mL). The organics were combined, dried over sodium sulfate, filtered and concentrated in vacuo. Chromatography on silica gel (Gradient: 0% to 30% ethyl acetate in heptane) afforded the product as a white solid. Yield: 37 mg, 58%. LCMS m/z 490.3 [M+H$^+$]. $^1$H NMR (400 mhz, CDCl$_3$) δ 8.24 (d, J=7.0 Hz, 2H), 7.63-7.66 (m, 2H), 7.41-7.56 (m, 5H), 6.90-7.01 (m, 2H), 4.78 (dd, J=11.5, 2.3 Hz, 1H), 4.33 (dd, J=12.3, 1.6 Hz, 1H), 3.99 (d, J=12.3 Hz, 1H), 3.32-3.36 (m, 1H), 3.07 (dd, J=12.9, 4.1 Hz, 1H), 2.68 (dd, J=12.9, 2.7 Hz, 1H), 2.12-2.22 (m, 1H), 1.91-1.96 (m, 1H).

Step 3. Synthesis of 4-[(4aR,6R,8aS)-2-amino-8a-(2,4-difluorophenyl)-4,4a,5,6,8,8a-hexahydropyrano[3,4-d][1,3]thiazin-6-yl]benzonitrile (31)

N-[(4aR,6R,8aS)-6-(4-Cyanophenyl)-8a-(2,4-difluorophenyl)-4,4a,5,6,8,8a-hexahydropyrano[3,4-d][1,3]thiazin-2-yl]benzamide (C26) (37 mg, 76 μmol, 1 equiv.) was dissolved in methanol (1.9 mL) and 1,8-diazabicyclo[5.4.0]undec-7-ene (0.01 mL, 0.06 mmol, 0.8 equiv) was added. The reaction was stirred at 80° C. for 16 hours. The reaction mixture was diluted with a saturated solution of sodium bicarbonate (10 mL) and extracted with ethyl acetate (3×20 mL). The organics were combined, dried over sodium sulfate, filtered and concentrated in vacuo. Chromatography on silica gel (Gradient: 0% to 50% ethyl acetate in heptane) afforded the product as a white solid. Yield: 27 mg, 91%. LCMS m/z 386.2 [M+H]. $^1$H NMR (400 MHz, CDCl$_3$) δ 7.64-7.67 (m, 2H), 7.53-7.55 (m, 2H), 7.4 (td, J=9.0, 6.7 Hz, 1H), 6.82-6.95 (m, 2H), 4.73 (dd, J=11.4, 2.2 Hz, 1H), 4.25 (dd, J=11.4, 2.2 Hz, 1H), 4.00 (d, J=11.5 Hz, 1H), 3.11-3.17 (m, 1H), 3.04 (dd, J=12.5, 4.1 Hz, 1H), 2.66 (dd, J=12.5, 2.9 Hz, 1H), 1.95-2.05 (m, 1H), 1.78-1.83 (m, 1H).

Examples 32-34

(4R,4a R, 6R, 8aS)-8a-(2,4-Difluorophenyl)-6-phenyl-4-methyl-4,4a, 5,6,8,8a-hexahydropyrano[3,4-d][1,3]thiazin-2-amines (32-34)

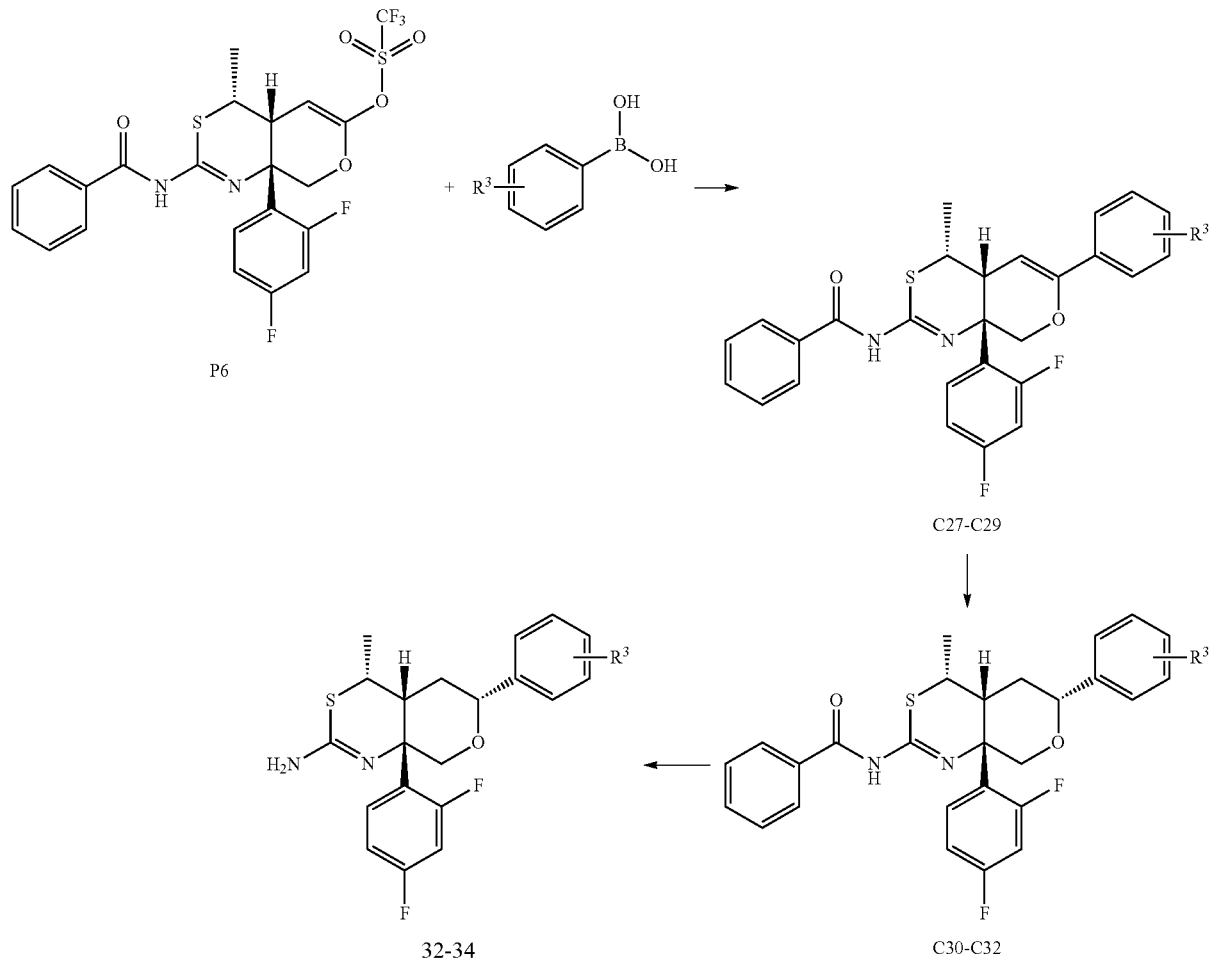

In the scheme above it is to be understood that the appropriately substituted boronic acid can have one $R^3$ group as depicted or up to three independently selected $R^3$ groups. The final compounds can then correspondingly have between one and three $R^3$ groups on the phenyl.

Step 1. Synthesis of N-[(4R,4aR,8aS)-8a-(2,4-difluorophenyl)-4-methyl-6-phenyl-4,4a,8,8a-tetrahydropyrano[3,4-d][1,3]thiazin-2-yl]benzamides (C27-C29)

(4R,4aR,8aS)-2-(Benzoylamino)-8a-(2,4-difluorophenyl)-4-methyl-4,4a,8,8a-tetrahydropyrano[3,4-d][1,3]thiazin-6-yl trifluoromethanesulfonate (P6) was converted to the products using the method described for synthesis of C25 as in Example 31.

Step 2. Synthesis of N-[(4R,4aR,6R,8aS)-8a-(2,4-difluorophenyl)-4-methyl-6-phenyl-4,4a,5,6,8,8a-hexahydropyrano[3,4-d][1,3]thiazin-2-yl]benzamides (C30-32)

N-[(4R,4aR,8aS)-8a-(2,4-difluorophenyl)-4-methyl-6-phenyl-4,4a, 8,8a-tetrahydropyrano[3,4-d][1,3]thiazin-2-yl]benzamides (C27-C29) were converted to the corresponding products using the method described for synthesis of N-[(4aR,6R,8aS)-6-(4-cyanophenyl)-8a-(2,4-difluorophenyl)-4,4a,5,6,8,8a-hexahydropyrano[3,4-d][1,3]thiazin-2-yl]benzamide (C26) as in Example 31.

Step 3. Synthesis of (4R,4aR,6R,8aS)-8a-(2,4-difluorophenyl)-6-phenyl-4-methyl-4,4a,5,6,8,8a-hexahydropyrano[3,4-d][1,3]thiazin-2-amines (32-34)

N-[(4R,4aR,6R,8aS)-8a-(2,4-Difluorophenyl)-4-methyl-6-phenyl-4,4a,5,6,8,8a-hexahydropyrano[3,4-d][1,3]thiazin-2-yl]benzamides (C30-C32) were converted to the corresponding products using the method described for synthesis of 4-[(4aR,6R,8aS)-2-amino-8a-(2,4-difluorophenyl)-4,4a, 5,6,8,8a-hexahydropyrano[3,4-d][1,3]thiazin-6-yl]benzonitrile (31) as in Example 31. See Table 1A for characterizing data for examples 32-34.

(4R,4aR,6R,8aS)-8a-(2,4-Difluorophenyl)-6-(4-fluorophenyl)-4-methyl-4,4a,5,6,8,8a-hexahydropyrano[3,4-d][1,3]thiazin-2-amine (32); Yield: 27 mg, 65%.

(4R,4aR,6R,8aS)-8a-(2,4-Difluorophenyl)-6-(4-cyanophenyl)-4-methyl-4,4a,5,6,8,8a-hexahydropyrano[3,4-d][1,3]thiazin-2-amine (33); Yield: 14 mg, 58%.

(4R,4aR,6R,8aS)-8a-(2,4-Difluorophenyl)-6-(3-cyanophenyl)-4-methyl-4,4a,5,6,8,8a-hexahydropyrano[3,4-d][1,3]thiazin-2-amine (34); Yield: 16 mg, 83%.

TABLE 1A

| Example # | Structure $\overset{R^2}{\underset{\xi}{\xi}}$ | $^1$H NMR (400 MHz, CD$_3$OD), δ (ppm); Mass spectrum, observed ion m/z [M + H$^+$] |
|---|---|---|
| 33 | 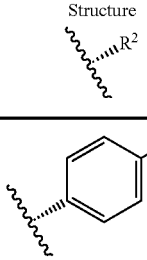 | 7.64-7.68 (m, 2H), 7.53-7.55 (m, 2H), 7.38 (td, J = 9.0, 6.7 Hz, 1H), 6.88-6.93 (m, 1H), 6.84 (ddd, J = 12.0, 8.6, 2.5 Hz, 1H), 4.7 (dd, J = 11.6, 2.4 Hz, 1H), 4.27 (dd, J = 11.2, 2.2 Hz, 1H), 4.01 (d, J = 11.5 Hz, 1H), 3.22 (qd, J = 7.0, 3.1 Hz, 1H), 2.90 (dt, J = 11.9, 3.8 Hz, 1H), 1.78-1.83 (m, 1H), 1.61-1.71 (m, 1H), 1.21 (d, J = 7.0 Hz, 3H); 400.2 |
| 34 | 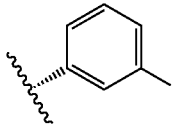 | 7.75 (t, J = 1.7 Hz, 1H), 7.67 (dt, J = 7.8, 1.6 Hz, 1H), 7.58 (dt, J = 7.8, 1.4 Hz, 1H), 7.46 (t, J = 7.7 Hz, 1H), 7.39 (td, J = 9.0, 6.7 Hz, 1H), 6.81-6.92 (m, 2H), 4.68 (dd, J = 11.5, 2.5 Hz, 1H), 4.27 (dd, J = 11.2, 2.3 Hz, 1H), 4.00 (d, J = 11.3 Hz, 1H), 3.21 (qd, J = 7.0, 3.3 Hz, 1H), 2.88 (dt, J = 11.9, 3.8 Hz, 1H), 1.78-1.83 (m, 1H), 1.63-1.73 (m, 1H), 1.21 (d, J = 7.0 Hz, 3H); 400.3 |

BIOLOGICAL ASSAYS

BACE1 Cell-Free Assay:

Beta-secretase (BACE) is one of the enzymes involved in the generation of the amyloid beta peptide found in the amyloid plaques of Alzheimer's Disease patients. This assay measures the inhibition of the beta-secretase enzyme as it cleaves a non-native peptide.

A synthetic APP substrate that can be cleaved by beta-secretase having N-terminal biotin and made fluorescent by the covalent attachment of Oregon Green at the Cys residue is used to assay beta-secretase activity in the presence or absence of the inhibitory compounds. The substrate is Biotin-GLTNIKTEEISEISY^EVEFR-C[Oregon Green]KK-OH. The BACE1 enzyme is affinity purified material from conditioned media of CHO-K1 cells that have been transfected with a soluble BACE construct (BACE1deltaTM96His). Compounds are incubated in a log dose response curve from a top concentration of 100 μM with BACE1 enzyme and the biotinylated fluorescent peptide in 384-well black plates (Thermo Scientific #4318). BACE1 is at a final concentration of 0.1 nM with a final concentration of peptide substrate of 150 nM in a reaction volume of 30 μL assay buffer [100 mM sodium acetate, pH 4.5 (brought to pH with acetic acid), and 0.001% Tween-20]. Plates are covered and incubated for 3 hours at 37° C. The reaction is stopped with the addition of 30 μL of 1.5 μM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of beta-secretase enzymatic cleavage of the synthetic APP substrate.

Whole Cell Assay (In Vitro sAPPpβ Assay):

H4 human neuroglioma cells over-expressing the wild-type human APP$_{695}$ are treated for 18 hours with compound in a final concentration 1% DMSO. sAPPβ levels are measured using TMB-ELISA with capture APP N-terminal antibody (Affinity BioReagents, OMA1-03132), wild-type sAPPβ specific reporter p192 (Elan), and tertiary anti rabbit-HRP (GE Healthcare).

BACE2 Assay:

This assay measures the inhibition of the BACE2 enzyme as it cleaves a non-native peptide. A synthetic substrate that can be cleaved by BACE2 having N-terminal biotin and made fluorescent by the covalent attachment of Oregon Green at the Cys residue is used to assay BACE2 activity in the presence or absence of the inhibitory compounds. The substrate is Biotin-KEISEISYEVEFR-C(Oregon green)-KK-OH. The BACE2 enzyme is available from Enzo Life Sciences (Cat #BML-SE550). Compounds are incubated in a log dose response curve from a top concentration of 100 μM with BACE2 enzyme and the biotinylated fluorescent peptide in 384-well black plates (Thermo Scientific #4318). BACE2 is at a final concentration of 2.5 nM with a final concentration of peptide substrate of 150 nM in a reaction volume of 30 μL assay buffer [100 mM sodium acetate, pH 4.5 (brought to pH with acetic acid), and 0.001% Tween-20]. Plates are covered and incubated for 3 hours at 37° C. The reaction is stopped with the addition of 30 μL of 1.5 μM Streptavidin (Pierce, #21125). After a 10 minute incubation at room temperature, plates are read on a PerkinElmer EnVision for fluorescence polarization (Ex485 nm/Em530 nm). The activity of the beta-secretase enzyme is detected by changes in the fluorescence polarization that occur when the substrate is cleaved by the enzyme. Incubation in the presence of compound inhibitor demonstrates specific inhibition of BACE2 enzymatic cleavage of the synthetic substrate.

The biological assay data for Examples 1-34 are found below in Table 2:

TABLE 2

| Example # | IUPAC name | BACE1 Cell-free Assay IC$_{50}$ (μM)$^a$ | sAPPβ Whole-Cell Assay IC$_{50}$ (nM)$^a$ |
|---|---|---|---|
| 1 | (4aR,6R,8aS)-8a-(2,4-difluorophenyl)-6-(4-fluorophenyl)-4,4a,5,6,8,8a-hexahydropyrano[3,4-d][1,3]thiazin-2-amine | 0.014 | 0.006 |
| 2 | (4aR,6R,8aS)-8a-(2,4-difluorophenyl)-6-(3-fluorophenyl)-4,4a,5,6,8,8a-hexahydropyrano[3,4-d][1,3]thiazin-2-amine | 0.022 | 0.009 |
| 3 | (4aR,6R,8aS)-8a-(2,4-difluorophenyl)-6-(2-fluorophenyl)-4,4a,5,6,8,8a-hexahydropyrano[3,4-d][1,3]thiazin-2-amine | 0.086 | 0.055 |
| 4 | (4aR,6R,8aS)-6,8a-bis(2,4-difluorophenyl)-4,4a,5,6,8,8a-hexahydropyrano[3,4-d][1,3]thiazin-2-amine | 0.039 | 0.025 |
| 5 | (4aR,6R,8aS)-8a-(2,4-difluorophenyl)-6-(3,4-difluorophenyl)-4,4a,5,6,8,8a-hexahydropyrano[3,4-d][1,3]thiazin-2-amine | 0.010 | 0.007 |
| 6 | (4aR,6R,8aS)-8a-(2,4-difluorophenyl)-6-(4-methylphenyl)-4,4a,5,6,8,8a-hexahydropyrano[3,4-d][1,3]thiazin-2-amine | 0.024 | 0.005 |
| 7 | (4aR,6R,8aS)-8a-(2,4-difluorophenyl)-6-(2-methylphenyl)-4,4a,5,6,8,8a-hexahydropyrano[3,4-d][1,3]thiazin-2-amine | 0.970 | 0.665 |

TABLE 2-continued

| Example # | IUPAC name | BACE1 Cell-free Assay IC$_{50}$ (μM)[a] | sAPPβ Whole-Cell Assay IC$_{50}$ (nM)[a] |
|---|---|---|---|
| 8 | (4aR,6R,8aS)-8a-(2,4-difluorophenyl)-6-(4-fluoro-3-methylphenyl)-4,4a,5,6,8,8a-hexahydropyrano[3,4-d][1,3]thiazin-2-amine | 0.006 | 0.008 |
| 9 | (4aR,6R,8aS)-8a-(2,4-difluorophenyl)-6-(3-fluoro-4-methylphenyl)-4,4a,5,6,8,8a-hexahydropyrano[3,4-d][1,3]thiazin-2-amine | 0.013 | 0.012 |
| 10 | (4aR,6R,8aS)-8a-(2,4-difluorophenyl)-6-(3-fluoro-5-methylphenyl)-4,4a,5,6,8,8a-hexahydropyrano[3,4-4[1,3]thiazin-2-amine | 0.016 | 0.038 |
| 11 | (4aR,6R,8aS)-8a-(2,4-difluorophenyl)-6-(2-fluoro-5-methylphenyl)-4,4a,5,6,8,8a-hexahydropyrano[3,4-4[1,3]thiazin-2-amine | 0.021 | 0.017 |
| 12 | (4aR,6R,8aS)-6-(4-chlorophenyl)-8a-(2,4-difluorophenyl)-4,4a,5,6,8,8a-hexahydropyrano[3,4-4[1,3]thiazin-2-amine | 0.015 | 0.016 |
| 13 | (4aR,6R,8aS)-8a-(2,4-difluorophenyl)-643-(trifluoromethyl)phenyl]-4,4a,5,6,8,8a-hexahydropyrano[3,4-4[1,3]thiazin-2-amine | 0.097 | 0.222 |
| 14 | (4aR,6R,8aS)-8a-(2,4-difluorophenyl)-644-(trifluoromethyl)phenyl]-4,4a,5,6,8,8a-hexahydropyrano[3,4-4[1,3]thiazin-2-amine | n.d.[c] | 0.176 |
| 15 | (4aR,6R,8aS)-8a-(2,4-difluorophenyl)-644-(trifluoromethoxy)phenyl]-4,4a,5,6,8,8a-hexahydropyrano[3,4-d][1,3]thiazin-2-amine | 0.021 | 0.142 |
| 16 | (4aR,6R,8aS)-8a-(2,4-difluorophenyl)-6-(4-methoxyphenyl)-4,4a,5,6,8,8a-hexahydropyrano[3,4-d][1,3]thiazin-2-amine | 0.029 | 0.018 |
| 17 | (4aR,6R,8aS)-8a-(2,4-difluorophenyl)-6-(2-methoxyphenyl)-4,4a,5,6,8,8a-hexahydropyrano[3,4-d][1,3]thiazin-2-amine | 2.212 | 0.691 |
| 18 | (4aR,6R,8aS)-8a-(2,4-difluorophenyl)-6-(4-fluoro-3-methoxyphenyl)-4,4a,5,6,8,8a-hexahydropyrano[3,4-d][1,3]thiazin-2-amine | 0.214 | 0.095 |
| 19 | (4aR,6R,8aS)-8a-(2,4-difluorophenyl)-6-(3-fluoro-4-methoxyphenyl)-4,4a,5,6,8,8a-hexahydropyrano[3,4-d][1,3]thiazin-2-amine | 0.044 | 0.023 |
| 20 | (4aR,6R,8aS)-8a-(2,4-difluorophenyl)-6-(2-fluoro-4-methoxyphenyl)-4,4a,5,6,8,8a-hexahydropyrano[3,4-d][1,3]thiazin-2-amine | 0.083 | 0.039 |
| 21 | (4aR,6R,8aS)-8a-(2,4-difluorophenyl)-6-(3-fluoro-5-methoxyphenyl)-4,4a,5,6,8,8a-hexahydropyrano[3,4-d][1,3]thiazin-2-amine | 0.335 | 0.216 |
| 22 | (4aR,6R,8aS)-8a-(2,4-difluorophenyl)-6-(2-fluoro-5-methoxyphenyl)-4,4a,5,6,8,8a-hexahydropyrano[3,4-d][1,3]thiazin-2-amine | 0.397 | 0.248 |
| 23 | (4aR,6R,8aS)-8a-(2,4-difluorophenyl)-6-(4-ethoxyphenyl)-4,4a,5,6,8,8a-hexahydropyrano[3,4-d][1,3]thiazin-2-amine | 0.011 | 0.021 |
| 24 | (4aR,6R,8aS)-8a-(2,4-difluorophenyl)-643-(methoxymethyl)phenyl]-4,4a,5,6,8,8a-hexahydropyrano[3,4-4[1,3]thiazin-2-amine | 0.161 | 0.071 |
| 25 | (4aR,6R,8aS)-8a-(2,4-difluorophenyl)-644-(methoxymethyl)phenyl]-4,4a,5,6,8,8a-hexahydropyrano[3,4-4[1,3]thiazin-2-amine | 0.022 | 0.010 |
| 26 | (4aR,6R,8aS)-8a-(2,4-difluorophenyl)-6-(2,3-dihydro-1-benzofuran-5-yI)-4,4a,5,6,8,8a-hexahydropyrano[3,4-d][1,3]thiazin-2-amine | 0.006 | 0.005 |
| 27 | (4aR,6R,8aS)-6-(1,3-benzodioxo1-5-yI)-8a-(2,4-difluorophenyl)-4,4a,5,6,8,8a-hexahydropyrano[3,4-d][1,3]thiazin-2-amine | 0.019 | 0.008 |
| 28 | (4aR,6R,8aS)-8a-(2,4-difluorophenyl)-644-(1-methoxyethyl)phenyl]-4,4a,5,6,8,8a-hexahydropyrano[3,4-d][1,3]thiazin-2-amine | 0.210 | 0.055 |
| 29 | 3-[(4aR,6R,8aS)-2-amino-8a-(2,4-difluorophenyl)-4,4a,5,6,8,8a-hexahydropyrano[3,4-d][1,3]thiazin-6-ypenzonitrile | 0.099 | 0.012 |
| 30 | 4-[(4aR,6R,8aS)-2-amino-8a-(2,4-difluorophenyl)-4,4a,5,6,8,8a-hexahydropyrano[3,4-d][1,3]thiazin-6-ypenzonitrile | 0.042 | 0.022 |
| 31 | (4aR,6R,8aS)-8a-(2,4-difluorophenyl)-644-(difluoromethyl)phenyl]-4,4a,5,6,8,8a-hexahydropyrano[3,4-d][1,3]thiazin-2-amine | 0.028 | 0.004 |
| 32 | (4R,4aR,6R,8aS)-8a-(2,4-difluorophenyl)-6-(4-fluorophenyl)-4-methyl-4,4a,5,6,8,8a-hexahydropyrano[3,4-d][1,3]thiazin-2-amine | 0.015[b] | 0.004[b] |
| 33 | (4R,4aR,6R,8aS)-8a-(2,4-difluorophenyl)-6-(4-cyanophenyl)-4-methyl-4,4a,5,6,8,8a-hexahydropyrano[3,4-d][1,3]thiazin-2-amine | 0.011[b] | 0.006[b] |
| 34 | (4R,4aR,6R,8aS)-8a-(2,4-difluorophenyl)-6-(3-cyanophenyl)-4-methyl-4,4a,5,6,8,8a-hexahydropyrano[3,4-d][1,3]thiazin-2-amine | 0.014[b] | 0.004[b] |

[a] Reported IC$_{50}$ values are the geometric mean of 2-3 determinations.
[b] Reported IC$_{50}$ values on a single determination.
[c] Not determined

We claim:
1. A compound of Formula I

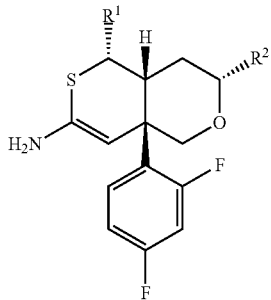

wherein
R¹ is hydrogen or methyl, wherein said methyl is optionally substituted with one to three fluoro;
R² is phenyl substituted with one to five R³;
R³ at each occurrence is independently selected from the group consisting of halogen, hydroxy, cyano, $C_{1-6}$alkyl, $C_{1-6}$alkoxy, $C_{1-6}$alkoxy-$C_{1-6}$alkyl, $C_{3-6}$cycloalkoxy, $C_{3-6}$cycloalkyl-$(CR^{4a}R^{4b})_m$—, $C_{3-6}$cycloalkoxy-$(CR^{4a}R^{4b})_m$—, $C_{3-6}$Cycloalkyl-$(CR^{4a}R^{4b})_m$—O— or (4- to 6-membered heterocycloalkyl)-$(CR^{4a}R^{4b})_m$—; wherein said $C_{1-6}$alkyl, $C_{1-6}$alkoxy or $C_{1-6}$alkoxy-$C_{1-6}$alkyl are each optionally substituted with one to three fluoro and wherein said $C_{3-6}$cycloalkyl, $C_{3-6}$cycloalkoxy and (4- to 6-membered heterocycloalkyl) moieties are optionally substituted with one to three substituents independently selected from the group consisting of fluoro, methyl, fluoromethyl, difluoromethyl or trifluoromethyl; or two R³, when attached to adjacent carbons on the phenyl and taken together, can be —(CH₂)ₙ—O—, —O—(CH₂)ₒ—O— or —(CH₂)ₚ—;
$R^{4a}$ and $R^{4b}$ are independently hydrogen, methyl, fluoromethyl, difluoromethyl, trifluoromethyl or methoxy;
m at each occurrence is independently 0, 1 or 2;
n is 2 or 3;
is 1 or 2; and
p is 3 or 4;
or a tautomer thereof or a pharmaceutically acceptable salt of said compound or tautomer.
2. The compound according to claim 1 wherein
R² is

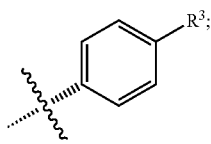

R³ is selected from the group consisting of chloro, fluoro, cyano, methyl, difluoromethyl, trifluoromethyl, methoxy, ethoxy, methoxymethyl, and 1-methoxyethyl;
or a tautomer thereof or a pharmaceutically acceptable salt of said compound or tautomer.
3. The compound according to claim 2 wherein R¹ is hydrogen; or a tautomer thereof or a pharmaceutically acceptable salt of said compound or tautomer.

4. The compound according to claim 2 wherein R¹ is methyl; or a tautomer thereof or a pharmaceutically acceptable salt of said compound or tautomer.
5. The compound according to claim 3 selected from the group consisting of:
(4aR,6R,8aS)-8a-(2,4-difluorophenyl)-6-(4-fluorophenyl)-4,4a,5,6,8,8a-hexahydropyrano[3,4-d][1,3]thiazin-2-amine;
(4aR,6R,8aS)-6-(4-chlorophenyl)-8a-(2,4-difluorophenyl)-4,4a,5,6,8,8a-hexahydropyrano[3,4-d][1,3]thiazin-2-amine;
(4aR,6R,8aS)-8a-(2,4-difluorophenyl)-6-[4-(trifluoromethyl)phenyl]-4,4a,5,6,8,8a-hexahydropyrano[3,4-d][1,3]thiazin-2-amine;
(4aR,6R,8aS)-8a-(2,4-difluorophenyl)-6-[4-(trifluoromethoxy)phenyl]-4,4a,5,6,8,8a-hexahydropyrano[3,4-d][1,3]thiazin-2-amine;
(4aR,6R,8aS)-8a-(2,4-difluorophenyl)-6-(4-methoxyphenyl)-4,4a,5,6,8,8a-hexahydropyrano[3,4-d][1,3]thiazin-2-amine;
(4aR,6R,8aS)-8a-(2,4-difluorophenyl)-6-(4-ethoxyphenyl)-4,4a,5,6,8,8a-hexahydropyrano[3,4-d][1,3]thiazin-2-amine;
(4aR,6R,8aS)-8a-(2,4-difluorophenyl)-6-[4-(methoxymethyl)phenyl]-4,4a,5,6,8,8a-hexahydropyrano[3,4-d][1,3]thiazin-2-amine;
(4aR,6R,8aS)-8a-(2,4-difluorophenyl)-6-[4-(1-methoxyethyl)phenyl]-4,4a,5,6,8,8a-hexahydropyrano[3,4-d][1,3]thiazin-2-amine;
4-[(4aR,6R,8aS)-2-amino-8a-(2,4-difluorophenyl)-4,4a,5,6,8,8a-hexahydropyrano[3,4-d][1,3]thiazin-6-yl]benzonitrile; and
(4aR,6R,8aS)-8a-(2,4-difluorophenyl)-6-[4-(difluoromethyl)phenyl]-4,4a,5,6,8,8a-hexahydropyrano[3,4-d][1,3]thiazin-2-amine;
or a tautomer thereof or a pharmaceutically acceptable salt of said compound or tautomer.
6. The compound according to claim 4 selected from the group consisting of
(4R,4aR,6R,8aS)-8a-(2,4-difluorophenyl)-6-(4-fluorophenyl)-4-methyl-4,4a,5,6,8,8a-hexahydropyrano[3,4-d][1,3]thiazin-2-amine; and
(4R,4aR,6R,8aS)-8a-(2,4-difluorophenyl)-6-(4-cyanophenyl)-4-methyl-4,4a,5,6,8,8a-hexahydropyrano[3,4-d][1,3]thiazin-2-amine;
or a tautomer thereof or a pharmaceutically acceptable salt of said compound or tautomer.
7. The compound according to claim 1 wherein
R¹ is hydrogen or methyl;
R² is

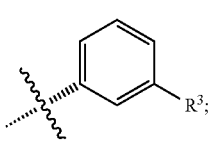

R³ is selected from fluoro, cyano, trifluoromethyl or methoxymethyl;
or a tautomer thereof or a pharmaceutically acceptable salt of said compound or tautomer.
8. The compound according to claim 7 selected from the group consisting of (4aR,6R,8aS)-8a-(2,4-difluorophenyl)-6-(3-fluorophenyl)-4,4a,5,6,8,8a-hexahydropyrano[3,4-d][1,3]thiazin-2-amine;

(4aR,6R,8aS)-8a-(2,4-difluorophenyl)-6-[3-(trifluoromethyl)phenyl]-4,4a,5,6,8,8a-hexahydropyrano[3,4-d][1,3]thiazin-2-amine;

(4aR,6R,8aS)-8a-(2,4-difluorophenyl)-6-[3-(methoxymethyl)phenyl]-4,4a,5,6,8,8a-hexahydropyrano[3,4-d][1,3]thiazin-2-amine;

3-[(4aR,6R,8aS)-2-amino-8a-(2,4-difluorophenyl)-4,4a,5,6,8,8a-hexahydropyrano[3,4-d][1,3]thiazin-6-yl]benzonitrile; and (4R,4aR,6R,8aS)-8a-(2,4-difluorophenyl)-6-(3-cyanophenyl)-4-methyl-4,4a,5,6,8,8a-hexahydropyrano[3,4-d][1,3]thiazin-2-amine;

or a tautomer thereof or a pharmaceutically acceptable salt of said compound or tautomer.

9. The compound according to claim 1 wherein
R$^1$ is hydrogen; and
R$^2$ is

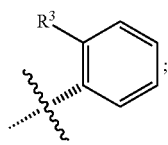

or a tautomer thereof or a pharmaceutically acceptable salt of said compound or tautomer.

10. The compound of claim 9 selected from
(4aR,6R,8aS)-8a-(2,4-difluorophenyl)-6-(2-fluorophenyl)-4,4a,5,6,8,8a-hexahydropyrano[3,4-d][1,3]thiazin-2-amine; and (4aR,6R,8aS)-8a-(2,4-difluorophenyl)-6-(2-methoxyphenyl)-4,4a,5,6,8,8a-hexahydropyrano[3,4-d][1,3]thiazin-2-amine;

or a tautomer thereof or a pharmaceutically acceptable salt of said compound or tautomer.

11. The compound of claim 1 wherein
R$^1$ is hydrogen; and
R$^2$ is

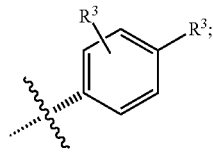

or a tautomer thereof or a pharmaceutically acceptable salt of said compound or tautomer.

12. The compound of claim 11 wherein
R$^3$ at each occurrence is independently selected from fluoro, methyl or methoxy; or the two R$^3$, when attached to adjacent carbons on the phenyl and taken together, can be —(CH$_2$)$_n$—O— or —O—(CH$_2$)$_o$—O—;
n is 2; and
o is 1;

or a tautomer thereof or a pharmaceutically acceptable salt of said compound or tautomer.

13. The compound of claim 12 selected from the group consisting of
(4aR,6R,8aS)-6,8a-bis(2,4-difluorophenyl)-4,4a,5,6,8,8a-hexahydropyrano[3,4-d][1,3]thiazin-2-amine;

(4aR,6R,8aS)-8a-(2,4-difluorophenyl)-6-(3,4-difluorophenyl)-4,4a,5,6,8,8a-hexahydropyrano[3,4-d][1,3]thiazin-2-amine;

(4aR,6R,8aS)-8a-(2,4-difluorophenyl)-6-(4-fluoro-3-methylphenyl)-4,4a,5,6,8,8a-hexahydropyrano[3,4-d][1,3]thiazin-2-amine;

(4aR,6R,8aS)-8a-(2,4-difluorophenyl)-6-(3-fluoro-4-methylphenyl)-4,4a,5,6,8,8a-hexahydropyrano[3,4-d][1,3]thiazin-2-amine;

(4aR,6R,8aS)-8a-(2,4-difluorophenyl)-6-(4-fluoro-3-methoxyphenyl)-4,4a,5,6,8,8a-hexahydropyrano[3,4-d][1,3]thiazin-2-amine;

(4aR,6R,8aS)-8a-(2,4-difluorophenyl)-6-(3-fluoro-4-methoxyphenyl)-4,4a,5,6,8,8a-hexahydropyrano[3,4-d][1,3]thiazin-2-amine;

(4aR,6R,8aS)-8a-(2,4-difluorophenyl)-6-(2-fluoro-4-methoxyphenyl)-4,4a,5,6,8,8a-hexahydropyrano[3,4-d][1,3]thiazin-2-amine;

(4aR,6R,8aS)-8a-(2,4-difluorophenyl)-6-(2,3-dihydro-1-benzofuran-5-yl)-4,4a,5,6,8,8a-hexahydropyrano[3,4-d][1,3]thiazin-2-amine; and (4aR,6R,8aS)-6-(1,3-benzodioxol-5-yl)-8a-(2,4-difluorophenyl)-4,4a,5,6,8,8a-hexahydropyrano[3,4-d][1,3]thiazin-2-amine;

or a tautomer thereof or a pharmaceutically acceptable salt of said compound or tautomer.

14. The compound of claim 1 wherein
R$^1$ is hydrogen;
R$^2$ is

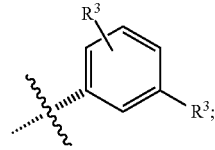

R$^3$ at each occurrence is independently selected from fluoro, methyl and methoxy;
or a tautomer thereof or a pharmaceutically acceptable salt of said compound or tautomer.

15. The compound according to claim 14 selected from the group consisting of
(4aR,6R,8aS)-8a-(2,4-difluorophenyl)-6-(3-fluoro-5-methylphenyl)-4,4a,5,6,8,8a-hexahydropyrano[3,4-d][1,3]thiazin-2-amine;

(4aR,6R,8aS)-8a-(2,4-difluorophenyl)-6-(2-fluoro-5-methylphenyl)-4,4a,5,6,8,8a-hexahydropyrano[3,4-d][1,3]thiazin-2-amine; and (4aR,6R,8aS)-8a-(2,4-difluorophenyl)-6-(3-fluoro-5-methoxyphenyl)-4,4a,5,6,8,8a-hexahydropyrano[3,4-d][1,3]thiazin-2-amine;

or a tautomer thereof or a pharmaceutically acceptable salt of said compound or tautomer.

16. A pharmaceutical composition comprising a therapeutically effective amount of a compound of claim 1, or a tautomer thereof or a pharmaceutically acceptable salt of said compound or tautomer, and a pharmaceutically acceptable vehicle, diluent or carrier.

17. A method of treating Alzheimer's disease in a patient, the method comprising administering a therapeutically effective amount of a compound according to claim 1, or a tautomer thereof or a pharmaceutically acceptable salt of said compound or tautomer to the patient in need of treatment thereof.

* * * * *